(12) United States Patent
Howe et al.

(10) Patent No.: US 7,851,218 B2
(45) Date of Patent: Dec. 14, 2010

(54) CELL LINES FOR PRODUCTION OF REPLICATION-DEFECTIVE ADENOVIRUS

(75) Inventors: John A. Howe, Greenbrook, NJ (US); Ken N. Wills, Carlsbad, CA (US); Robert Orville Ralston, II, Union, NJ (US); Scott Joseph Sherrill, Chesterfield, MO (US)

(73) Assignee: Schering Corporation, Kenilworth, NJ (US)

( * ) Notice: Subject to any disclaimer, the term of this patent is extended or adjusted under 35 U.S.C. 154(b) by 687 days.

(21) Appl. No.: 11/301,309

(22) Filed: Dec. 12, 2005

(65) Prior Publication Data

US 2006/0270041 A1 Nov. 30, 2006

Related U.S. Application Data

(60) Provisional application No. 60/635,561, filed on Dec. 13, 2004, provisional application No. 60/674,488, filed on Apr. 25, 2005.

(51) Int. Cl.
C12N 15/00 (2006.01)
C12N 15/09 (2006.01)
C12N 15/33 (2006.01)
C12N 5/07 (2006.01)
C12N 5/10 (2006.01)

(52) U.S. Cl. .................. 435/455; 435/325; 435/366; 536/23.1; 536/23.72

(58) Field of Classification Search .................. None
See application file for complete search history.

(56) References Cited

U.S. PATENT DOCUMENTS

| | | | |
|---|---|---|---|
| 5,837,520 A | 11/1998 | Shabram et al. | |
| 5,891,690 A | 4/1999 | Massie | |
| 5,932,210 A | 8/1999 | Gregory et al. | |
| 5,994,134 A | 11/1999 | Giroux et al. | |
| 6,146,891 A | 11/2000 | Condon et al. | |
| 6,165,779 A | 12/2000 | Engler et al. | |
| 6,210,939 B1 | 4/2001 | Gregory et al. | |
| 6,248,514 B1 | 6/2001 | Hutchins et al. | |
| 6,261,823 B1 | 7/2001 | Tang et al. | |
| 6,312,681 B1 | 11/2001 | Engler et al. | |
| 6,392,069 B2 | 5/2002 | Engler et al. | |
| 6,395,519 B1 | 5/2002 | Fallaux et al. | |
| 6,430,595 B1 | 8/2002 | Ferguson et al. | |
| 6,544,769 B1 | 4/2003 | Frei et al. | |
| 6,649,158 B1* | 11/2003 | LaFace ................ | 424/93.2 |
| 6,783,983 B1 | 8/2004 | Condon et al. | |
| 6,835,557 B1 | 12/2004 | Weissmann et al. | |
| 7,001,770 B1 | 2/2006 | Atencio et al. | |
| 7,074,618 B2* | 7/2006 | Li et al. ................ | 435/455 |
| 2002/0064860 A1 | 5/2002 | Cannon-Carlson et al. | |
| 2002/0150557 A1* | 10/2002 | Ramachandra et al. ...... | 424/93.2 |
| 2005/0074885 A1* | 4/2005 | Vogels et al. ............. | 435/456 |
| 2006/0270041 A1 | 11/2006 | Howe et al. | |

FOREIGN PATENT DOCUMENTS

| | | |
|---|---|---|
| WO | WO 96/27677 A2 | 9/1996 |
| WO | WO 1999/41416 | 8/1999 |
| WO | WO 2004/108088 | 12/2004 |
| WO | WO 2005/058368 | 6/2005 |
| WO | WO 2006/065827 | 6/2006 |
| WO | WO 2007/090392 | 6/2007 |

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
ATCC search results pp. 1-2, SL0003, downloaded Aug. 11, 2009.*
ATCC search results pp. 1-2, SL0006, downloaded Aug. 11, 2009.*
ATCC search results pp. 1-2, PTA-6231, downloaded Aug. 11, 2009.*
ATCC search results pp. 1-2, PTA-6663, downloaded Aug. 11, 2009.*
Babiss et al., "Adenovirus E1B Proteins Are Required for Accumulation of Late Viral mRNA and for Effects on Cellular mRNA Translation and Transport", *Molecular and Cellular Biology*, 5(10):2552-2558 (Oct. 1985).
Bayley et al., "Adenovirus E1A proteins and transformation (Review)", *International Journal of Oncology*, 5:425-444 (1994).
Branton et al., "Transformation By Human Adenoviruses", *Biochimca et Biophysica Acta*, 780:67-94 (1985).
Condon et al., "Development of a Chinese Hamster Ovary Cell Line for Recombinant Adenovirus-Mediated Gene Expression", *Biotechnol. Prog.*, 19:137-143 (2003).
Demers et al., "Pharmacologic Indicators of Antitumor Efficacy for Oncolytic Virotherapy", *Cancer Research*, 63:4003-4008 (Jul. 15, 2003).
Doronin et al., "Tumor-specific, Replication-Competent Adenovirus Vectors Overexpressing the Adenovirus Death Protein", *J. Virol.*, 74(13):6147-6155 (Jul. 2000).
Fallaux et al., "New Helper Cells and Matched Early Region 1-Deleted Adenovirus Vectors Prevent Generation of Replication-Competent Adenoviruses", *Human Gene Therapy*, 9:1909-1917 (Sep. 1, 1998).

(Continued)

*Primary Examiner*—Maria B Marvich

(57) ABSTRACT

The present invention provides cell lines for the production of E1-deleted adenovirus (rAd) vectors that complement E1A and E1B functions. The present invention also provides cell lines for the production of E1- and E2-deleted adenovirus vectors that complement E1A, E1B and E2B polymerase functions. The invention provides particular cell lines that complement E1A function by insertion of an E1A sequence containing mutations in the 243R and 289R proteins and an E1B sequence comprising the E1B-55K gene. Production yields in the resulting producer cell lines, designated SL0003 and SL0006, were similar to those obtained from 293 cells without generation of detectable recombinant replication competent adenovirus ("RCA").

2 Claims, 20 Drawing Sheets

OTHER PUBLICATIONS

Frisch et al., "Adenovirus-5 E1A: Paradox and Paradigm", *Nature Reviews Molecular Cell Biology*, 3:441-452 (Jun. 2002).

Frisch, "Antioncogenic effect of adenovirus E1A in human tumor cells", *Proc. Natl. Acad. Sci. USA*, 88:9077-9081 (Oct. 1991).

Graham et al., "Characteristics of a Human Cell Line Transformed by DNA from Human Adenovirus Type 5", *J. Gen Virol.*, 36:59-74 (1977).

Harada et al., "p53-Independent and -Dependent Requirements for E1B-55K in Adenovirus Type 5 Replication", *Journal of Virology*, 73(7):5333-5344 (Jul. 1999).

Howe et al., "Retinoblastoma Growth Suppressor and a 300-kDa Protein Appear to Regulate Cellular DNA Synthesis", *Proc. Natl. Acad. Sci. USA*, 87(15):5883-87 (Aug. 1990).

Howe et al., "Evaluation of E1-Mutant Adenoviruses as Conditionally Replicating Agents for Cancer Therapy", *Mol. Ther.*, 2(5):485-495 (Nov. 2000).

Howe et al., "Matching Complementing Functions of Transformed Cells with Stable Expression of Selected Viral Genes for Production of E1-Deleted Adenovirus Vectors", *Virology*, 345(1):220-230 (2006).

Huyghe et al., "Purification of a Type 5 Recombinant Adenovirus Encoding Human p53 by Column Chromatography", *Human Gene Therapy*, 6:1403-1416 (Nov. 1995).

Imler et al., "Novel complementation cell lines derived from human lung carcinoma A549 cells support the growth of E-1 deleted adenovirus vectors", *Gene Therapy*, 3:75-84 (1996).

Lochmuller et al., "Emergence of Early Region 1-Containing Replication-Competent Adenovirus in Stocks of Replication-Defective Adenovirus Recombinants (ΔE1+ΔE3) During Multiple Passages in 293 Cells", *Human Gene Therapy*, 5:1485-1491 (Dec. 1994).

Louis et al., "Cloning and Sequencing of the Cellular—Viral Junctions from the Human Adenovirus Type 5 Transformed 293 Cell Line", *Virology*, 233:423-429 (1997).

Murakami et al., "A Single Short Stretch of Homology Between Adenoviral Vector and Packaging Cell Line Can Give Rise to Cytopathic Effect-Inducing, Helper-Dependent E1-Positive Particles", *Human Gene Therapy*, 13:909-920. (May 20, 2002).

Mymryk et al., "Induction of apoptosis by adenovirus type 5 E1A in rat cells requires a proliferation block", *Oncogene*, 9:1187-1193 (1994).

Querido et al., "Regulation of p53 Levels by the E1B 55-Kilodalton Protein and E4orf6 in Adenovirus-Infected Cells", *Journal of Virology*, 71(5):3788-3798 (May 1997).

Rao et al., "The adenovirus E1A proteins induce apoptosis, which is inhibited by the E1B 19-kDa and Bcl-2 proteins", *Proc. Natl. Acad. Sci. USA*, 89:7742-7746 (Aug. 1992).

Shabram et al., "Analytical Anion-Exchange HPLC of Recombinant Type-5 Adenoviral Particles", *Human Gene Therapy*, 8:453-465 (Mar. 1, 1997).

Shenk, "Adenoviridae: The Viruses and Their Replication", *Fields Virology*, Third Edition, Chapter 67, 2:2111-2148 (1996).

White et al., "Adenovirus E1B 19-Kilodalton Protein Overcomes the Cytotoxicity of E1A Proteins", *Journal of Virology*, 65(6): 2968-2978 (Jun. 1991).

Zhu et al., "Characterization of Replication-Competent Adenovirus Isolates from Large-Scale Production of a Recombinant Adenoviral Vector", *Human Gene Therapy*, 10:113-121 (Jan. 1, 1999).

Amalfitano et al, "Production and Characterization of Improved Adenovirus Vectors with the E1, E2b, and E3 Genes Deleted", Journal of Virology, vol. 72, No. 2, pp. 926-933 (1998).

Appleby et al, "A Novel Combination of Promoter and Enhancers Increases Transgene Expression in Vascular Smooth Muscle Cells In Vitro and Coronary Arteries In Vivo After Adenovirus-Mediated Gene Transfer", Gene Therapy, vol. 10, pp. 1616-1622 (2003).

Aurisicchio et al, "Liver-Specific Alpha 2 Interferon Gene Expression Results in Protection from Induced Hepatitis", Journal of Virology, vol. 74, No. 10, pp. 4816-4823 (2000).

Bell et al, "The Protein CTCF Is Required for the Enhancer Blocking Activity of Vertebrate Insulators", Cell, vol. 98, pp. 387-396 (1999).

Bell et al, "Insulators and Boundaries: Versatile Regulatory Elements in the Eukaryotic Genome", Science, vol. 291, pp. 447-450 (2001).

Benedict et al, "Intravesical Ad-IFN-a Causes Marked Regression of Human Bladder Cancer Growing Orthotopically in Nude Mice and Overcomes Resistance to IFN-a Protein", Molecular Therapy, vol. 10, No. 3, pp. 525-532 (2004).

Benoist et al, "In Vivo Sequence Requirements of the SV40 Early Promoter Region", Nature, vol. 290, pp. 304-310 (1981).

Berkner et al, "Expression of Dihydrofolate Reductase, and of the Adjacent E1b Region, in an Ad5-Ihydrofolat Reductase Recombinant Virus", Nucleic Acids Research, vol. 12, No. 4, pp. 1925-1941 (1984).

Berkner et al, "Generation of Adenovirus by Transfection of Plasmids", Nucleic Acids Research, vol. 11, No. 17, pp. 6003-6020 (1983).

Boschetti, "Advanced Sorbents for Preparative Protein Separation Purposes", Journal of Chromatography A, vol. 658, pp. 207-236 (1994).

Brasset et al, "Insulators are Fundamental Components of the Eukaryotic Genomes", Heredity, vol. 94, pp. 571-576 (2005).

Breckpot et al, "Lentivirally Transduced Dendritic Cells as a Tool for Cancer Immunotherapy", The Journal of Gene Medicine, vol. 5, pp. 654-667 (2003).

Brinster et al, "Regulation of Metallothionein-Thymidine Kinase Fusion Plasmids Injected into Mouse Eggs", Nature, vol. 296, pp. 39-42 (1982).

Brough et al, "Construction, Characterization, and Utilization of Cell Lines Which Inducibly Express the Adenovirus DNA-Binding Protein" Virology, vol. 190, pp. 624-634 (1992).

Brun et al, "Optimization of Transgene Expression at the Posttranscriptional Level in Neural Cells: Implications for Gene Therapy", Molecular Therapy, vol. 7, No. 6, pp. 782-789 (2003).

Buchwald et al, "Long-Term, Continuous Intravenous Heparin Administration by an Implantable Infusion Pump in Ambulatory Patients with Recurrent Venous Thrombosis", Surgery, vol. 88, pp. 507-516 (1980).

Carbone et al, "Multistep and Multifactorial Carcinogenesis: When Does a Contributing Factor Become a Carcinogen?", Seminars in Cancer Biology, vol. 14, pp. 399-405 (2004).

Cheng et al, "A Novel TARP-Promoter-Based Adenovirus against Hormone-Dependent and Hormone-Refractory Prostate Cancer", Molecular Therapy, vol. 10, No. 2, pp. 355-364 (2004).

Choi et al, "A Generic Intron Increases Gene Expression in Transgenic Mice", Molecular and Cellular Biology, vol. 11, No. 6, pp. 3070-3074 (1991).

Connor et al, "Sustained Intravesical Interferon Protein Exposure Is Achieved Using An Adenoviral-Mediated Gene Delivery System: a Study in Rats Evaluating Dosing Regimens", Urology, vol. 66, No. 1, pp. 224-229 (2005).

Davison et al, "Genetic Content and Evolution of Adenoviruses", Journal of General Virology, vol. 84, pp. 2895-2908 (2003).

Demers et al, "Tumor Growth Inhibition by Interferon-α using PEGylated Protein or Adenovirus Gene Transfer with Constitutive or Regulated Expression", Molecular Therapy, vol. 6, No. 1 pp. 50-56 (2002).

Demers et al, "Interferon-α2b Secretion by Adenovirus-Mediated Gene delivery in Rat, Rabbit, and Chimpanzee Results in Similar Pharmacokinetic Profiles", Toxicology and Applied Pharmacology, vol. 180, pp. 36-42 (2002).

Di Simone et al, "The Sear Urchin sns Insulator Blocks CMV Enhancer following Integration in Human Cells", Biochemical and Biophysical Research Communications, vol. 284, pp. 987992 (2001).

Donello et al, "Woodchuck Hepatitis Virus Contains a Tripartite Posttranscriptional Regulatory Element", Journal of Virology, vol. 72, No. 6, pp. 5085-5092 (1998).

Dunn et al, "The Many Roles of the Transcriptional Regulatory CTCF", Biochem. Cell Biology, vol. 81, pp. 161-167 (2003).

Dunn et al, "The Insulator Binding Protein CTCF Associates with the Nuclear Matrixx", Experimental Cell Research, fol. 288, pp. 218-223 (2003).

During et al, "Controlled Release of Dopamine from a Polymeric Brain Implant: in Vivo Characterization", Annals of Neurology, vol. 25, No. 4, pp. 351-356 (1989).

Eck et al, "Gene-Based Therapy", Goodman & Gilman's the Pharmacological Basis of Therapeutics, McGraw-Hill, New York, NY, pp. 77-101 (1996).

Emery et al, "Development of Virus Vectors for Gene Therapy of β Chain Hemoglobinopathies: Flanking with a Chromatin Insulator Reduces y-Globin Gene Silencing in Vivo", Blood, vol. 100, No. 6, pp. 2012-2019 (2002).

Farrell et al, "Conserved CTCF Insulator Elements Flank the Mouse and Human β-Globin Loci", Molecular and Cellular Biology, vol. 22, No. 11, pp. 3820-3831 (2002).

Glover et al, "Adenoviral-Mediated, High-Level, Cell-Specific Transgene Expression: A SYN1-WPRE Cassette Mediates Increased Transgene Expression with No Loss of Neuron Specificity", Molecular Therapy, vol. 5, No. 5, pp. 509-516 (2002).

Glover et al, "Long-Term Transgene Expression Can be Mediated in the Brain by Adenoviral Vectors When Powerful Neuron-Specific Promoters are Used", the Journal of Gene Medicine, vol. 5, pp. 554-559 (2003).

Graham et al, "Transformation of Rat Cells by CAN of Human Adenovirus 5", Virology, vol. 54, pp. 536-539 (1973).

Gropp et al, "Stable Genetic Modification of Human Embryonic Stem Cells by Lentiviral Vectors", Molecular Therapy, vol. 7, No. 2, pp. 281-287 (2003).

Gura et al, "Systems for Identifying New Drugs", Science, vol. 278, pp. 1041-1042 (1997).

Hardy et al, "Construction of Adenovirus Vectors through Cre-lox Recombination", Journal of Virology, vol. 71, No. 3, pp. 1842-1849 (1997).

Haruna et al, "Separation of Adenovirus by Chromatography on DEAE-Cellulose", Virology, vol. 13, No. 2, pp. 264-267 (1961).

Hermening et al, "Increased Protein Expression from Adenoviral Shuttle Plasmids and Vectors by Insertion of a Small Chimeric Intron Sequence", Journal of Virological Methods, vol. 122, pp. 73-77 (2004).

Howard et al, "Intracerebral Drug Delivery in Rats with Lesion-Induced Memory Deficits", J. Neurosurgery, vol. 71, pp. 105-112 (1989).

Huang et al, "Hepatitis B Virus Rna Element That Facilitates Accumulation of Surface Gene Transcripts in the Cytoplasm", Journal of Virology, vol. 68, No. 5, pp. 3193-3199 (1994).

Iqbal Ahmed et al, "Interferon α2b Gene Delivery Using Adenoviral Vector Causes Inhibition of Tumor Growth in Xenograft Models from a Variety of Cancers", Cancer Gene Therapy, vol. 8, No. 10, pp. 788-795 (2001).

Jakobsson et al, "Dynamics of Transgene Expression in a Neural Stem Cell Line Transduced with Lentiviral Vectors Incorporating the cHS4 Insulator", Experimental Cell Research, vol. 298, pp. 611-623 (2004).

Jerne et al, "Towards a Network Theory of the Immune System", Ann. Immunol., vol. 125C, pp. 373-389 (1974).

Jerne et al, "Recurrent Idiotypes and Internal Images", The EMBO Journal, vol. 1, No. 2, pp. 243-247 (1982).

Kanduri et al, "Multiple Nucleosome Positioning Sites Regulate the CTCF-Mediated Insulator Function of the H19 Imprinting Control Region", Molecular and Cellular Biology, vol. 22, No. 10, pp. 3339-3344 (2002).

Kelland et al, "'Of Mice and Men': Values and Liabilities of the Athymic Nude Mouse Model in Anticancer Drug Development", European Journal of Cancer, vol. 40, pp. 827-836 (2004).

Kerbel, "Human Tumor Xenografts as Predictive Preclinical Models for Anticancer Drug Activity in Humans", Cancer Biology & Therapy, vol. 2, Supp. 1, pp. S134-139 (2003).

Klemperer et al, "Study of Adenovirus Antigens Fractionated by Chromatography on DEAE-Celllulose", Virology, vol. 9, pp. 536-545 (1959).

Kochanek et al, "A New Adenoviral vector: Replacement of all Viral Coding Sequences with 28 kb of DNA Independently Expressing Both Full-Length Dystrophin and β-galactosidase", Proceedings of the National Academy of Sciences USA, vol. 93, pp. 5731-5736 (1996).

Kumar-Singh et al, "Encapsidaed Adenovirus Minichromosomes Allow Delivery and Expression of a 14 kb Dystrophin cDNA to Muscle Cells", Human Molecular Genetics, vol. 5, No. 7, pp. 913-921 (1996).

Langer, "New Methods of Drug Delivery", Science, vol. 249, pp. 1527-1533 (1990).

Langer, "Chemical and Physical Structure of Polymers as Carriers for Controlled Release of Bioactive Agents: A Review", J. Macromol. Sci Rev Macromol. Chem.. Phys., vol. C23, No. 1, pp. 61-126 (1983).

Langer, "Implantable Controlled Release Systems", Pharmacol. Ther., vol. 21, pp. 35-51 (1983).

Lee et al, "Comparison of Various Expression Plasmids for the Induction of Immune Response by DNA Immunization", Mol. Cells, vol. 7, No. 4, pp. 495-501 (1997).

Levy, "Inhibition of Calcification of Bioprosthetic Heart Valves by Local Controlled-Release Diphosphonate", Science, vol. 228, pp. 190-192 (1985).

Lewis et al, "Geonomic Imprinting: CTCF Protects the Boundaries", Current Biology, vol. 14, pp. R284-R286 (2004).

Liu et al, "HnRNP L Binds a Cis-Acting RNA Sequence Element that Enables Intron-Independent Independent Gene Expression", Genes & Development, vol. 9, pp. 1766-1780 (1995).

Lu et al, "Delivery of Adenoviaral Vectors to the Prostate for Gene Therapy", Cancer Gene Therapy, vol. 6, No. 1, pp. 64-72 (1999).

Lutz et al, "Transcriptional Repression by the Insulator Protein CTCF Involves Histone Deacetylases", Nucleic Acids Research, vol. 28, No. 8, pp. 1707-1713 (2000).

Mangeot et al, "High Levels of Transduction of Human Dendritic Cells with Optimized SIV Vectors", Molecular Therapy, vol. 5, No. 3, pp. 283-290 (2002).

Martin-Duque et al, "Direct Comparison of the Insulating Properties of Two genetic Elements in an Adenoviral Vector Containing Two Different Expression Cassettes", Human Gene Therapy, vol. 15, pp. 995-1002 (2004).

McCutchan et al, "Enhancement of the Infectivity of Simian Virus 40 Deoxyribonucleic Acid with Diethyl-Aminoethyl-Dextran", Journal of the National Cancer Institute, vol. 41, pp. 351357 (1968).

Mitani et al, "Rescue, Propagation, and Partial Purificastion of a Heler Virus-Dependent Adenovirus Vector", Proceedings of the National Academy of Sciences USA, vol. 92, pp. 3854-3858(1995).

Mukhopadhyay et al, "The Binding Sites for the Chromatin Insulator Protein CTCF Map to DNA Methylation-Free Domains Genome-Wide", Genome Research, vol. 14, pp. 1594-1602 (2004).

Pannell et al, "Silencing of Gene Expression: Implications for Design of Retrovirus Vectors", Rev. Med. Virol., vol. 11, pp. 205-217 (2001).

Parks et al, "A Helper-Dependent Adenovirus Vector System: Removal of Helper Virus by Cre-Mediated Excision of the Viral Packaging Signal", Proceedings of the National Academy of Sciences USA, vol. 93, pp. 13565-13570 (1996).

Philipson, "Separation on DEAE Cellulose of Components Associated with Adenovirus Reproduction", Virology, vol. 10, pp. 459-465 (1960).

Pluta et al, "Tight Control of Transgene Expression by Lentivirus Vectors Containing Second-Generation Tetracycline-Responsive Promoters", The Journal of Gene Medicine, vol. 7, pp. 803-817 (2005).

Puthenveetil et al, "Successful Correction of the Human β-thalassemia Major Phenotype Using a Lentiviral Vector", Blood, vol. 104, No. 12, pp. 3445-3453 (2004).

Qu et al, "Homogeneity and Long-Term Stability of Tetracycline-Regulated Gene Expression with Low Basal Activity by Using the rtTA2S-M2 Transactivator and Insulator-Ranked Reporter Vectors", Gene, vol. 327, pp. 61-73 (2004).

Recillas-Targa et al, "Position-Effect Protection and Enhancer Blocking by the Chicken βGlobin Insulator are Separable Activities", Proceedings of the National Academy of Sciences USA, vol. 99, No. 10, pp. 6883-6888 (2002).

Rincón-Arano et al, "Sustained Heterologous Transgene Expression in Mammalian and Avian Cell Lines", Methods in Molecular Biology, vol. 267, pp. 435-450 (2004).

Robert et al, "A Sin Lentiviral Vector Containing Pega cDNA Allows Long-Term Phenotypic Correction of CD34+ -Derived Cells from Patients with Paroxysmal Nocturnal Hemoglobinuria", Molecular Therapy, vol. 7, No. 3, pp. 304-316 (2003).

Rodrigues, "Permeable Packings and Perfusion Chromatography in Protein Separation", Journal of Chromatography B, vol. 699, pp. 47-61 (1997).

Rubanyi, "The Future of Human Gene Therapy", Molecular Aspects of Medicine, vol. 22, pp. 113-142 (2001).

Saitoh et al, "Structural and Functional Conversation at the Boundaries of the Chicken β-Globin Domain", The EMBO Journal, vol. 19, No. 10, pp. 2315-2322 (2000).

Saudek et al, "A Preliminary Trial of the Programmable Implantable Medication System for Insulin Delivery", The New England Journal of Medicine, vol. 321, No. 9, pp. 574-579 (1989).

Schwenter et al, "Optimization of Human Erythropoietin Secretion from MLV-Infected Human Primary Fibroblasts Used for Encapsulatd Cell Therapy", The Journal of Gene Medicine, vol. 5, pp. 246-257 (2003).

Sefton, "Implantable Pumps", Critical Reviews in Biomedical Engineering, vol. 14, No. 3, pp. 201-240 (1987).

Simon et al, "Adenovirus-Mediated Transfer of the CFTR Gene to Lung of Nonhuman Primates: Toxicity Study", Human Gene Therapy, vol. 4, pp. 771-780 (1993).

Steinwaerder et al, "Insulation from Viral Transcriptional Regulatory Elements Improves Inducible Transgene Expression From Adenovirus Vectors in Vitro and in Vivo", Gene Therapy, vol. 7, pp. 556-567 (2000).

Szabo et al, "The Chicken β-globin Insulator Element Conveys Chromatin Boundary Activity but not Imprinting at the Mouse Igf2/H19 Domain", Development, vol. 129, pp. 897-904 (2002).

Takada et al, "Evaluation of Heterologous Insulator Function with Regard to Chromosomal Position Effect in the Mouse blastocyst and Fetus", Molecular Reproduction and Development, vol. 57, pp. 232-237 (2000).

Thorvaldsen et al, "Analysis of Sequence Upstream of the Endogenous H19 Gene Reveals Elements Both Essential and Dispensable for Imprinting", Molecular and Cellular Biology, vol. 22, No. 8, pp. 2450-2462 (2002).

Valadez-Graham et al, "CTCF-Dependent Enhancer Blockers at the Upstream Region of the Chicken α-globin Gene Domain", Nucleic Acids Research, vol. 32, No. 4, pp. 1354-1362 (2004).

Vassaux et al, "Insulation of a Conditionally Expressed Transgene in an Adenoviral Vector", Gene Therapy, vol. 6, pp. 1192-1197 (1999).

Vile et al, "Cancer Gene Therapy: Hard Lessons and New Courses", Gene Therapy, vol. 7, pp. 2-8 (2000).

Wagner et al, "The Human β-globin Gene and a Functional Viral Thymidine Kinase Gene in Developing Mice", Proceedings of the National Academy of Sciences USA, vol. 78, No. 8, pp. 5016-5020 (1981).

Werner et al, "B-Cell-Specific Transgene Expression Using a Self-Inactivating Retroviral Vector with Human CD19 Promoter and Viral Post-Transcriptional Regulatory Element", Gene Therapy, vol. 11, pp. 992-1000 (2004).

Xu et al, "Woodchuck Hepatitis Virus Post-Transcriptional Regulation Element Enhances Transgene Expression from Adenovirus Vectors", Biochimica et Biophysica Acta, vol. 1621, pp. 266-271 (2003).

Xu et al, "Strength Evaluation of Transcriptional Regulatory Elements for Transgene Expression by Adenovirus Vector", Journal of Controlled Release, vol. 81, pp. 155-163 (2002).

Yam et al, "Design of HIV Vectors for Efficient Gene Delivery into Human Hematopoietic Cells", Molecular Therapy, vol. 5, No. 4, pp. 479-484 (2002).

Yamamoto et al., "Identification of a Functional Promoter in the Long Terminal Repeat of Rous Sarcoma Virus", Cell, vol. 22, pp. 787-797 (1980).

Yannaki et al, "Topological Constraints Governing the Use of the Chicken HS4 Chromatin Insulastor in Oncoretrovirus Vectors", Molecular Therapy, vol. 5, No. 5, pp. 589-598 (2002).

Yao et al, "Retrovirus Silencer Blocking by the cHS4 Insulator is CTCF Independent", Nucleic Acids Research, vol. 31, No. 18, pp. 5317-5323 (2003).

Ye et al, "Insulation from Viral Transcriptional Regulatory Elements Enables Improvement to Hepatoma-Specific Gene Expression from Adenovirus Vectors", Biochemical and Biophysical Research Communications, vol. 307, pp. 759-764 (2003).

Youil et al, "Comparative Analysis of the Effects of Packaging Signal, Transgene Orientation, Promoters, Polyadenylation Signals, and E3 Region on Growth Properties of First-Generation Adenoviruses", Human Gene Therapy, vol. 14, pp. 1017-1034 (2003).

Yusufzai et al, "CTCF Tethers an Insulator to Subnuclear Sites, Suggesting Shared Insulator Mechanisms Across Species", Molecular Cell, vol. 13, pp. 291-298 (2004).

Yusufzai et al, "The 5'-HS4 Chicken β-globin Insulator is a CTCF-Dependent Nuclear Matrix-Associated Element", Proceedings of the National Academy of Sciences USA, vol. 101, No. 23, pp. 8620-8624 (2004).

Zhang et al, "Dynamic Association of the Mammalian Insulator Protein CTCF with Centrosomes and the Midbody", Experimental Cell Research, vol. 294, pp. 86-93 (2004).

Zhao et al, "An Insulator Blocks Spreading of Histone Acetylation and Interferes with RNA Polymerase II Transfer Between an Enhancer and Gene", Nucleic Acids Research, vol. 32, No. 16, pp. 4903-4914 (2004).

Zufferey et al, "Woodchuck Hepatitis Vrius Posttranscriptional Regulatory element Enhances Expression of Transgenes Delivered by Retroviral Vectors", Journal of Virology, vol. 73, No. 4, pp. 2886-2892 (1999).

GenBank Accession No. AC000008 (Human Adenovirus C Serotype 5) dated Oct. 31, 1996 (Replaced by AC003656).

GenBank Database Accession No. AY339865 (Human adenovirus C serotype 5) dated Aug. 13, 2007.

* cited by examiner

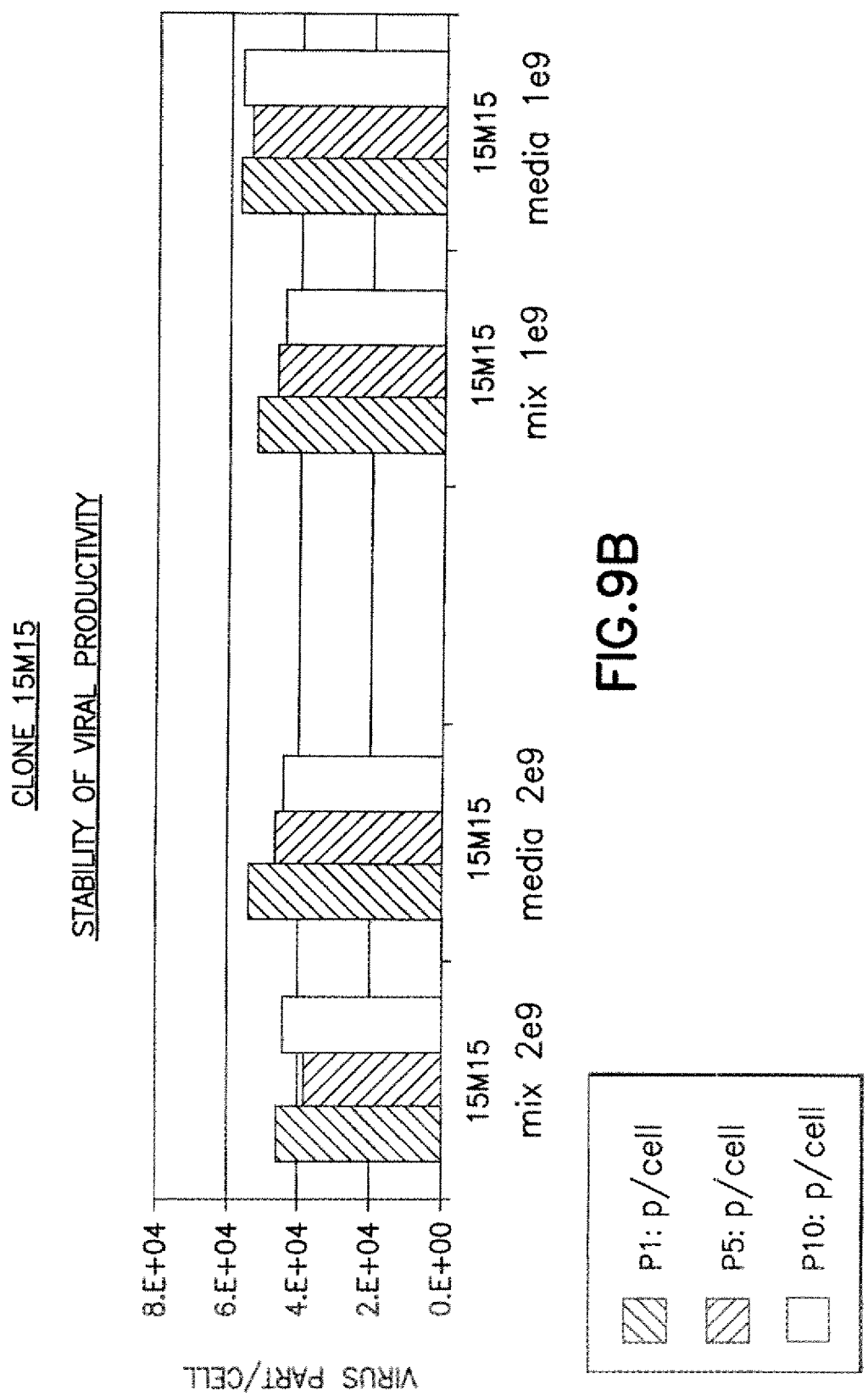

CELL LINES FOR PRODUCTION OF REPLICATION-DEFECTIVE ADENOVIRUS

CROSS-REFERENCE TO RELATED APPLICATIONS

This application claims benefit of priority under 35 USC §119(e) of U.S. provisional patent application Ser. No. 60/635,561, filed Dec. 13, 2004 and U.S. provisional patent application Ser. No. 60/674,488 filed, Apr. 25, 2005, the disclosures of which are herein incorporated by reference in their entirety.

FIELD OF THE INVENTION

The present invention relates to cell lines useful for the efficient production of replication-defective adenoviruses. The invention also describes methods of use of such cell lines to produce replication-defective adenoviruses.

BACKGROUND OF THE INVENTION

Recombinant adenovirus (rAd) vectors have desirable features for gene delivery, including wide tissue and cell tropism, the capacity to accommodate large expression cassettes and high transduction efficiency. In addition, adenovirus is well suited for pharmaceutical development as the virus grows to high specific titers and scalable manufacturing processes have been established (Huyghe et al., (1995) Hum. Gene Ther. 6:1403-1416; Shabram et al., (1997) Hum. Gene Ther. 8:453-465). Production of rAd vectors requires engineered cell lines that can complement functions removed from the viral genome. For pharmaceutical development and commercial manufacture of viral vectors, the vector-cell line combination also must be amenable to scale-up and provide material of sufficient quality and purity.

Replication defective rAd vectors for gene therapy use are generally deleted for the viral early region 1 (E1). E1 contains two transcription units, E1A and E1B, which encode a number of proteins that have critical roles in the early and late phases of the lytic cycle. Production of rAd vectors requires complementation of these E1 activities. E1A and E1B gene functions have been extensively characterized. A review of E1A and E1B functions is provided in Bayley, et al. (1994) International J. of Oncology 5:425-444 and Shenk, et al. (1996) in Adenoviridae: The Viruses and Their Replication, Fields Virology (K. D. M. Fields B. N., and Howley, P. M., Ed.), 2 Lippincott-Raven, Philadelphia, Pa. The first E1-complementing line, 293, was generated by transfection of primary embryonic kidney cells using physically sheared adenovirus 5 DNA (Graham et al., (1977) J Gen. Virol. 36:59-74). Genomic analysis subsequently demonstrated that 293 cells carry an integrated fragment of the left-hand end of adenovirus genome (bases 1-4344), containing the E1 region and additional flanking sequences (Louis et al., (1997) Virology 233:423-429).

Although 293 cells produce E1-deficient rAd vectors at acceptable levels, an undesirable contaminant called replication competent adenovirus ("RCA") is sometimes generated by homologous recombination between the rAd vector and the adenovirus sequences present in the 293 genome (Lochmuller et al, (1994) Hum. Gene Ther. 5:1485-1491; Zhu et al., (1999) Hum. Gene Ther. 10:113-121). To reduce the risk of generation of RCA by homologous recombination, Fallaux et al., (Hum. Gene Ther. 9:1909-1917 (1998)) transfected human embryonic retinoblasts with a recombinant plasmid containing E1 genes, in which the E1A promoter and E1B polyadenylation sequences were replaced by heterologous control elements. Deletion of the adenovirus flanking sequences in the E1 plasmid yielded a cell line, PER.C6, which does not generate RCA through homologous recombination when cell line-matched rAd vectors are employed (Fallaux et al., (1998) Hum. Gene Ther. 9:1909-1917). However, recent studies have shown that an atypical form of RCA, called helper-dependent E1-positive particles, can be formed when non-matched adenoviral vectors are propagated in PER.C6 cells (Murakami et al., (2002) Hum. Gene Ther. 13:1909-1920).

The E1 region used for complementation of E1-deleted adenoviruses in 293 cells and PER.C6 cells includes the entire E1B transcription unit, which encodes two major proteins: E1B-19K and E1B-55K. In adenovirus replication, the E1B-19K and E1B-55K proteins function in the early lytic cycle to limit E1A-induced apoptosis (Querido et al., (1997) J. Virol. 71:3788-3798; Rao et al., (1992) Proc. Natl. Acad. Sci. USA 89:7742-7746; White et al., (1991) J. Virol. 65:2968-2978). In addition, E1B-55K functions in the late phase to stimulate the accumulation and translational of viral late mRNAs (Babiss et al., (1985) Mol. Cell Biol. 5:2552-2558; Harada and Berk, (1999) J. Virol. 73:5333-5344). E1B has also has been shown to collaborate with E1A in transforming primary cells (Branton et al., (1985) Biochim. Biophys. Acta 780:67-94), and specifically protects against E1A sensitization to apoptosis (White et al., (1991) J. Virol. 65:2968-2978).

The construction of stable human cell lines that effectively and efficiently complement replication deficient adenoviral vectors can be difficult. A barrier for developing E1-complementing cell lines is the toxicity associated with high levels of E1A gene product expression. For example, constitutive expression of the E1 proteins, especially E1A, has proven difficult in established cell lines (Imler et al, (1996) Gene Ther. 3:75-84). E1A has been shown to suppress cell growth and induce anoikis (Frisch, (1991) Proc Natl Acad Sci USA 88:9077-9081; Frisch and Mymryk, (2002) Nat Rev Mol Cell Biol 3:441-452; Mymryk et al., (1994) Oncogene 9: 1187-1193; Rao et al., (1992) Proc Natl Acad Sci USA 89:7742-7746). Thus, complementation cell lines, such as those known in the art, that constitutively express E1A proteins may be associated with poor survival rates prior to and/or during adenoviral vector production.

Others have previously used human tumor cell lines, such as the A549 cell line, to develop E1-complementing cell lines. For example, Massie (U.S. Pat. No. 5,891,690) transformed A549 cells with an E1 region expression cassette in which the adenovirus E1A promoter was replaced with the human alpha-actin promoter. However, the yield of an adenovirus gene therapy vector expressing the bacterial beta-galactosidase gene was shown to be lower than from 293 cells. Imler, et al. used regulated induction of E1 as a strategy to avoid toxicity associated with constitutive expression of E1A, allowing generation of rAd producer cell lines based on A549 cells (Imler, et al., (1996) Gene Ther. 3:75-84). Production yields of rAd vectors from these Gal4-inducible producer cell lines were reported to be 5-10 fold lower than from 293 cells (Imler, et al., supra).

Accordingly, there is a need for more efficient recombinant cell lines to produce replication-defective adenoviruses (i.e., adenoviruses containing a deletion of the E1A and E1B coding regions of the adenoviral genome) which have low RCA and with production levels on the order of wild-type adenovirus production from the 293 cell line.

SUMMARY OF THE INVENTION

The present invention addresses the foregoing needs by providing new cell lines for the production of recombinant adenovirus based on combining selected viral and host functions required for adenovirus replication.

The present invention provides helper adenovirus nucleic acid sequences for use in the generation of host cells that complement the recombinant adenovirus vectors and recombinant adenoviruses described herein. The helper adenovirus nucleic acid sequences of the present invention: (i) provide viral functions for the replication of a recombinant adenovirus vector and/or its packaging into infectious virions; and (ii) are not replicated or assembled into viral particles to a measurable degree. The helper adenovirus nucleic acid sequences can be obtained and/or derived from any adenoviridae or a combination of adenoviridae. In a preferred embodiment, the helper adenovirus nucleic acid sequences are obtained and/or derived from a human adenoviridae.

In one embodiment, the helper adenovirus nucleic acid sequences include: (i) a nucleic acid molecule comprising a nucleotide sequence encoding adenoviral E1A proteins deficient in binding to p300 protein family members and pRb protein family members; and (ii) a nucleic acid molecule(s) comprising a nucleotide sequence(s) encoding an adenoviral E1B protein(s), such as E1B-55K and/or E1B-19K. In accordance with this embodiment, the helper adenovirus nucleic acid sequences may also include one, two or more of the following: (i) a nucleic acid molecule(s) comprising a nucleotide sequence(s) encoding an adenoviral E2 protein(s); (ii) a nucleic acid molecule(s) comprising a nucleotide sequence(s) encoding an adenoviral E4 protein(s); and/or (iii) a nucleic acid molecule comprising a nucleotide sequence encoding an adenoviral L4 100K protein. Non-limiting examples of adenoviral E2 proteins include E2A binding protein, E2B polymerase, E2B pre-terminal protein, and E2B IVa2 protein. Non-limiting examples of adenoviral E4 proteins include those encoded by open reading frame (ORF)-6, ORF3, and ORF6/7. Table 1 below provides examples of the nucleotide and amino acid sequences of human adenovirus serotype 5 E1A proteins, E1B-55K protein, E1B-19K protein and E2B polymerase protein.

TABLE 1

Sequences of the invention.

| Sequence | Sequence Identifier |
|---|---|
| plasmid pRcRSV-E1Adl01/07 | SEQ ID NO: 1 |
| plasmid pcDNA3.1(+)E1B 55K Hygro | SEQ ID NO: 2 |
| nucleotide sequence encoding human adenovirus type 5, 289R E1A, wild type | SEQ ID NO: 3 |
| amino acid sequence of human adenovirus type 5, 289R E1A, wild type, protein | SEQ ID NO: 4 |
| nucleotide sequence of human adenovirus type 5, 243R E1A, wild type | SEQ ID NO: 5 |
| amino acid sequence of human adenovirus type 5, 243R E1A, wild type, protein | SEQ ID NO: 6 |
| amino acid residues 4–25 of human adenovirus type 5, E1A 289R, wild type, protein | SEQ ID NO: 7 |
| amino acid residues 4–25 of human adenovirus type 5, E1A 243R, wild type, protein | SEQ ID NO: 8 |
| amino acid residues 36–49 of human adenovirus type 5, E1A 289R, wild type, protein | SEQ ID NO: 9 |
| amino acid residues 36–49 of human adenovirus type 5, E1A 243R, wild type, protein | SEQ ID NO: 10 |
| amino acid residues 111–123 of human adenovirus type 5, E1A 289R, wild type, protein | SEQ ID NO: 11 |
| amino acid residues 111–123 of human adenovirus type 5, E1A 243R, wild type, protein | SEQ ID NO: 12 |
| amino acid residues 124–127 of human adenovirus type 5, E1A 289R, wild type, protein | SEQ ID NO: 13 |
| amino acid residues 124–127 of human adenovirus type 5 E1A 243R, wild type, protein | SEQ ID NO: 14 |
| nucleotide sequence of human adenovirus type 5, E1B-55K, coding region | SEQ ID NO: 15 |
| amino acid sequence of human adenovirus type 5, E1B-55K, protein | SEQ ID NO: 16 |
| nucleotide sequence of human adenovirus type 5, E1A gene | SEQ ID NO: 17 |
| nucleotide sequence of human adenovirus type 5, E1B-55K and E1-19K, coding regions | SEQ ID NO: 18 |
| plasmid pVITRO21RESPuroE1b | SEQ ID NO: 19 |
| plasmid pMGCME2Bbpol | SEQ ID NO: 20 |
| nucleotide sequence of human adenovirus type 5, E1B-19K, coding region | SEQ ID NO: 21 |
| amino acid sequence of human adenovirus type 5, E1B-19K, protein | SEQ ID NO: 22 |
| nucleotide sequence of human adenovirus type 5, E2B, coding region | SEQ ID NO: 25 |
| nucleotide sequence of human adenovirus type 5, E2B polymerase, coding region | SEQ ID NO: 23 |
| amino acid sequence of human adenovirus type 5, E2B polymerase, protein | SEQ ID NO: 24 |
| nucleotide sequence of E1Adl01/07 | SEQ ID NO: 26 |
| Amino acid sequence of E1Adl01/07 | SEQ ID NO: 27 |

In a specific embodiment, the helper adenovirus nucleic acid sequences include: (i) a nucleic acid molecule comprising a nucleotide sequence encoding adenoviral E1A proteins deficient in binding to p300 protein family members and pRb protein family members; and (ii) a nucleic acid molecule comprising a nucleotide sequence encoding an adenoviral E1B protein, wherein the E1B protein comprises an E1B-55K protein but not an E1B-19K protein. In a preferred embodiment, the helper adenovirus nucleic acid sequences include: (i) a nucleic acid molecule comprising a nucleotide sequence encoding adenoviral E1A proteins deficient in binding to p300 protein family members and pRb protein family members; and (ii) a nucleic acid molecule comprising a nucleotide sequence encoding an adenoviral E2B polymerase; and (iii) a nucleic acid molecule comprising a nucleotide sequence encoding adenoviral E1B-55K and E1B-19K proteins.

To produce E1A proteins that are defective for binding to the cellular proteins p300/CBP and pRb, mutations in the E1A 289R and E1A 243R coding regions can be introduced. In a specific embodiment, the E1A proteins comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In a preferred embodiment, the E1A proteins comprise: (a) a first deletion corresponding to amino acid residues 4-25 of an E1A 289R protein (dl1101) and amino acid residues 4-25 of an E1A 243R protein (dl1101); and (b) a second deletion corresponding to amino acid residues 111-123 (dl1107) of an E1A 289R protein and amino acid residues 111-123 (dl1107) of an E1A 243R protein.

The present invention provides host cells transfected or transformed with the helper adenovirus nucleic acid sequences. Such cells are useful in the production of recombinant adenovirus, in particular replication-defective recombinant adenovirus. The host cells of the present invention complement functions missing from the recombinant adenovirus vector or recombinant adenovirus of interest (i.e., the adenoviral E1A, for example, SEQ ID NO: 17, and E1B, for example, SEQ ID NO: 18, coding regions). Preferably, the host cells contain complementing adenoviral genes that lack any homology to those in the recombinant adenoviral vector of interest, which reduces the possibility of the viral genome recombining with the cellular DNA to produce replication competent adenovirus. Host cells that complement the recombinant adenovirus vectors and recombinant adenoviruses described herein are sometimes referred to herein as "complementing cell lines", "rAd production cell lines", "rAd complementation cells" and "rAd complementation cell lines".

In a specific embodiment, the present invention provides an isolated host cell comprising: (a) first nucleic acid molecule comprising a nucleotide sequence encoding adenoviral E1A proteins deficient in binding to p300 protein family members and pRb protein family members; and (b) a second nucleic acid molecule comprising a nucleotide sequence encoding an adenoviral E1B-55K protein. In accordance with this embodiment, the second nucleic acid molecule, in certain embodiments, does not comprise a nucleotide sequence encoding an adenoviral E1B-19K protein. Further, in accordance with this embodiment, the host cell may further comprise additional nucleic acid molecules comprising nucleotide sequences encoding an adenoviral E2a DNA binding protein, an adenoviral E2b pre-terminal protein, an adenoviral E2b IVa2 protein, adenoviral E4 proteins (e.g., ORF 6, ORF 3 and ORF 6/7 of an adenoviral E4 gene), and/or an adenoviral protein encoded by L4 100K.

In a preferred embodiment, the present invention provides an isolated host cell comprising: (a) a first nucleic acid molecule comprising a nucleotide sequence encoding adenoviral E1A proteins deficient in binding to p300 protein family members and pRb protein family members; (b) a second nucleic acid molecule comprising a nucleotide sequence encoding an adenoviral E2B polymerase; and (c) a third nucleic acid molecule comprising a nucleotide sequence encoding adenoviral E1B-55K and E1B-19K proteins. In accordance with this embodiment, the host cell may further comprise additional nucleic acid molecules comprising nucleotide sequences encoding an adenoviral E2a DNA binding protein, an adenoviral E2b pre-terminal protein, an adenoviral E2b IVa2 protein, adenoviral E4 proteins (e.g., ORF 6, ORF 3 and ORF 6/7 of an adenoviral E4 gene), and/or an adenoviral protein encoded by L4 100K.

In a specific embodiment, the E1A proteins expressed by the host cells comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In a preferred embodiment, the E1A proteins expressed by the host cells comprise: (a) a first deletion corresponding to amino acid residues 4-25 of an E1A 289R protein (dl1101) and amino acid residues 4-25 of an E1A 243R protein (dl1101); and (b) a second deletion corresponding to amino acid residues 111-123 (dl1107) of an E1A 289R protein and amino acid residues 111-123 (dl1107) of an E1A 243R protein.

Any type of cell may be used as a host cell. In a preferred embodiment, a cell that is permissible to adenovirus, preferably human adenovirus, infection is used. In a preferred embodiment, human cells (including primary cells and cell lines) are used as host cells. Human established cell lines such as those from human tumor cells or human tumor cell lines have the ability to replicate indefinitely in culture. In a specific embodiment, the host cell is a A549, HCT-15, IGROV-1, HeLa, U87, W162 or 293-D22 cell. In a preferred embodiment, the host cell is a A549 cell.

In one embodiment, the present invention provides a human cell comprising stably integrated nucleic acid sequences comprising: (a) a first expression cassette comprising a promoter active in said human cell operably linked to a nucleic acid sequence encoding adenoviral E1A proteins deficient in binding to p300 protein family members and pRb protein family members, wherein said proteins are expressed in said human cell; and (b) a second expression cassette comprising a promoter active in said human cell operably linked to a nucleic acid sequence encoding an adenoviral E1B protein, wherein said E1B protein comprises an E1B-55K protein but not an E1B-19K protein, wherein said E1B-55K protein is expressed in said human cell. In a particular embodiment, the E1A proteins expressed by the human cell comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In a preferred embodiment the E1A proteins expressed by the human cell comprise: (a) a first deletion corresponding to amino acid residues 4-25 of said E1A 289R protein (dl1101) and amino acid residues 4-25 of said E1A 243R protein (dl1101); and (b) a second deletion corresponding to amino acid residues 111-123 (dl1107) of said E1A 289R protein and amino acid residues 111-123 (dl1107) of said E1A 243R protein.

The present invention provides the above human cells, wherein the first expression cassette comprises the nucleic acid sequence set forth in SEQ ID NO: 26 and/or the second expression cassette comprises the nucleic acid sequence set forth in SEQ ID NO: 15. In a specific embodiment, the first expression cassette comprises the nucleic acid sequence set forth in SEQ ID NO: 1 and/or the second expression cassette comprises the nucleic acid sequence set forth in SEQ ID NO: 2. The present invention also provides the above human cell, wherein the cell is designated SL0003, deposited with the American Type Culture Collection (ATCC) under accession number PTA-6231. In a specific embodiment of the invention, the recombinant adenovirus production cell line, is the cell line designated SL0003, deposited with the American Type Culture Collection (ATCC) under accession number PTA-6231.

In one embodiment, the present invention provides a human cell comprising stably integrated nucleic acid sequences comprising: (a) a first expression cassette comprising a promoter active in said human cell operably linked to a nucleic acid sequence encoding adenoviral E1A proteins deficient in binding to p300 protein family members and pRb protein family members, wherein said proteins are expressed in said human cell; (b) a second expression cassette comprising a promoter active in said human cell operably linked to a nucleic acid sequence encoding an adenoviral E2B polymerase protein, wherein said protein is expressed in said human cell; and (c) a third expression cassette comprising a promoter active in said human cell operably linked to a nucleic acid sequence encoding adenoviral E1B-55K and E1B-19K proteins, wherein said proteins are expressed in said human cell. In a particular embodiment, the E1A proteins expressed by the human cell comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In a preferred embodiment the E1A proteins expressed by the human cell comprise: (a) a first deletion corresponding to amino acid residues 4-25 of said E1A 289R protein (dl1101) and amino acid residues 4-25 of said E1A 243R protein (dl1101); and (b) a second deletion corresponding to amino acid residues 111-123 (dl1107) of said E1A 289R protein and amino acid residues 111-123 (dl1107) of said E1A 243R protein.

The present invention provides the above human cells, wherein the first expression cassette comprises the nucleic acid sequence set forth in SEQ ID NO: 26, the second expression cassette comprises the nucleic acid set forth in SEQ ID NO: 23 and/or the third expression cassette comprises the nucleic acid sequence set forth in SEQ ID NO: 18. In a specific embodiment, the first expression cassette comprises the nucleic acid sequence set forth in SEQ ID NO: 1, the second expression cassette comprises the nucleic acid set forth in SEQ ID NO: 20 and/or the third expression cassette comprises the nucleic acid sequence set forth in SEQ ID NO: 19. The present invention also provides the above human cell, wherein the cell is designated SL0006, deposited with the American Type Culture Collection (ATCC) under accession number PTA-6663. In a preferred embodiment of the invention, the recombinant adenovirus production cell line, is the cell line designated SL0006, deposited with the American Type Culture Collection (ATCC) under accession number PTA-6663.

Host cells may be transiently or stably transfected with helper adenovirus nucleic acid sequences utilizing techniques known in the art and/or described herein. Preferably, the helper adenovirus nucleic acid sequences are stably integrated into the nuclear genome of the host cells.

The present invention provides methods for producing a host cell for the production of replication-defective adenovirus comprising transforming or transfecting a cell (preferably, a human cell) with a first nucleic acid molecule and a second nucleic acid molecule, wherein the first nucleic acid molecule comprising a nucleotide sequence encoding adenoviral E1A proteins deficient in binding to p300 protein family members and pRb protein family members (examples of such adenoviral proteins are described below), and the second nucleic acid molecule comprises a nucleotide sequence encoding an adenoviral E1B-55K protein (and preferably, does not comprise a nucleotide sequence encoding an adenoviral E1B-19K protein). The cell may be transformed or transfected with the first and second nucleic acid molecules simultaneously or sequentially in any order. In a specific embodiment, the cell is transformed or transfected with the first nucleic acid molecule and then the second nucleic acid molecule.

The present invention provides methods for producing a cell for the production of replication-defective adenovirus comprising transforming or transfecting a cell (preferably, a human cell) with a first nucleic acid molecule, a second nucleic acid molecule and a third nucleic acid molecule, wherein the first nucleic acid molecule comprises a nucleotide sequence encoding adenoviral E1A proteins deficient in binding to p300 protein family members and pRb protein family members (examples of such adenoviral proteins are described below), the second nucleic acid molecule comprises a nucleotide sequence encoding an adenoviral E2b polymerase, and the third nucleic acid molecule comprises a nucleotide sequence encoding an adenoviral E1B-55K protein and preferably, a nucleotide sequence encoding an adenoviral E1B-55K protein and E1B-19K protein. The cell may be transformed or transfected with the first, second and third nucleic acid molecules simultaneously or sequentially in any order. In a specific embodiment, the cell is transformed or transfected with the first nucleic acid molecule, the second nucleic acid molecule, and then the third nucleic acid molecule.

In one embodiment, the invention provides a method for producing a human cell for the production of replication-defective adenovirus comprising: (a) transforming a human cell with a first expression cassette, wherein said first expression cassette comprises a promoter active in said human cell operably linked to a nucleic acid sequence encoding adenoviral E1A proteins deficient in binding to p300 protein family members and pRb protein family members, wherein said proteins are expressed in said human cell; and (b) transforming said human cell with a second expression cassette comprising a promoter active in said human cell operably linked to a nucleic acid sequence encoding an adenoviral E1B protein, wherein said E1B protein comprises an E1B-55K protein but not an E1B-19K protein, wherein said E1B-55K protein is expressed in said human cell. In a particular embodiment, the E1A proteins encoded by the first expression cassette comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In another embodiment, the E1A proteins encoded by the first expression cassette comprise: (a) said first deletion corresponding to amino acid residues 4-25 of said E1A 289R protein (dl1101) and amino acid residues 4-25 of said E1A 243R protein (dl1101); and (b) said second deletion corresponding to amino acid residues 111-123 (dl1107) of said E1A 289R protein and amino acid residues 111-123 (dl1107) of said E1A 243R protein.

The present invention provides the above methods, wherein the cell is derived from an established cell line, a tumor cell line, an A549 cell line, and a HeLa cell line. Also provided are the above methods, wherein the first expression cassette comprises the nucleic acid sequence set forth in SEQ ID NO: 26 and/or the second expression cassette comprises the nucleic acid sequence set forth in SEQ ID NO: 15. In a specific embodiment, the first expression cassette comprises the nucleic acid sequence set forth in SEQ ID NO: 1 and/or the second expression cassette comprises the nucleic acid sequence set forth in SEQ ID NO: 2.

In one embodiment, the invention provides a method for producing a human cell for the production of replication-defective adenovirus comprising: (a) transforming a human cell with a first expression cassette, wherein said first expression cassette comprises a promoter active in said human cell operably linked to a nucleic acid sequence encoding adenoviral E1A proteins deficient in binding to p300 protein family members and pRb protein family members, wherein said proteins are expressed in said human cell; (b) transforming said human cell with a second expression cassette comprising a promoter active in said human cell operably linked to a nucleic acid sequence encoding an adenoviral E2B polymerase protein, wherein said protein is expressed in said human cell; and (c) transforming said human cell with a third expression cassette comprising a promoter active in said human cell operably linked to a nucleic acid sequence encoding adenoviral E1B-55K and E1B-19K proteins, wherein said protein is expressed in said human cell. In a particular embodiment, the E1A proteins encoded by the first expression cassette comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In another embodiment, the E1A proteins encoded by the first expression cassette comprise: (a) said first deletion corresponding to amino acid residues 4-25 of said E1A 289R protein (dl1101) and amino acid residues 4-25 of said E1A 243R protein (dl1101); and (b) said second deletion corresponding to amino acid residues 111-123 (dl1107) of said E1A 289R protein and amino acid residues 111-123 (dl1107) of said E1A 243R protein.

The present invention provides the above methods, wherein the cell is derived from an established cell line, a tumor cell line, an A549 cell line, and a HeLa cell line. Also provided are the above methods, wherein the first expression cassette comprises the nucleic acid sequence set forth in SEQ ID NO: 26, the second expression cassette comprises the nucleic acid sequence set forth in SEQ ID NO: 23 and/or the third expression cassette comprises the nucleic acid sequence set forth in SEQ ID NO: 18. In a specific embodiment, the first expression cassette comprises the nucleic acid sequence set forth in SEQ ID NO: 1, the second expression cassette comprises the nucleic acid sequence set forth in SEQ ID NO: 20 and/or the third expression cassette comprises the nucleic acid sequence set forth in SEQ ID NO: 19.

In accordance with the invention, recombinant adenovirus (preferably, recombinant replication-defective adenovirus) may be produced by transfecting a rAd production cell line with a rAd vector to produce of recombinant adenovirus (preferably, recombinant replication-defective adenovirus). In a specific embodiment, the present invention provides a method for producing recombinant adenovirus comprising culturing a rAd complementing cell line transfected with recombinant adenovirus vector under conditions so as to permit replication of the viral genome in the cell line, wherein the cell line comprises: (a) a first nucleic acid molecule comprising a nucleotide sequence encoding adenoviral E1A proteins deficient in binding to p300 protein family members and pRb protein family members (see the description above regarding such E1A proteins); and (b) a second nucleic acid molecule comprising a nucleotide sequence encoding an adenoviral E1B-55K protein (and preferably, does not comprise a nucleotide sequence encoding an adenoviral E1B-19K protein). In a preferred embodiment, the present invention provides a method for producing recombinant adenovirus comprising culturing a rAd complementing cell line transfected with recombinant adenovirus vector under conditions so as to permit replication of the viral genome in the cell line, wherein the cell line comprises: (a) a first nucleic acid molecule comprising a nucleotide sequence encoding adenoviral E1A proteins deficient in binding to p300 protein family members and pRb protein family members (see the description above regarding such E1A proteins); (b) a second nucleic acid molecule comprising a nucleotide sequence encoding an adenoviral E2B polymerase; and (c) a third nucleic acid molecule comprising a nucleotide sequence encoding an adenoviral E1B-55K protein, and preferably, an adenoviral E1B-19K protein.

The recombinant adenovirus vectors transfected into rAd production cell lines comprise adenoviral nucleotide sequences and optionally, one or more heterologous nucleotide sequences. In a preferred embodiment, the recombinant adenovirus vectors comprise adenoviral nucleotide sequences that lack any homology to the helper adenovirus nucleic acid sequences. The lack of homology between the adenoviral helper nucleic acid sequences and recombinant adenovirus vectors reduces the possibility of the viral genome recombining to produce replication competent adenovirus. In a preferred embodiment, the recombinant adenovirus vector encodes a replication-defective adenovirus. In accordance with this embodiment, the recombinant adenovirus vector may be engineered to comprise a mutated adenovirus genome by, e.g., introducing one or more mutations in an adenovirus genome (e.g., introducing deletions in one or more coding regions for adenoviral proteins). Preferably, the mutations in the adenovirus genome result in lower levels of expression of adenoviral proteins than wild-type adenovirus. The reduction in adenoviral protein expression reduces the immune response to the adenoviral proteins in a subject.

In a specific embodiment, the recombinant adenovirus vector encodes a replication-defective adenovirus and comprises a mutated genome with a partial or complete (preferably, a complete) deletion of the E1A coding region (e.g., SEQ ID NO: 17) and E1B coding region (e.g., SEQ ID NO: 18), and may include one or more heterologous nucleotide sequences. In another embodiment, the recombinant adenovirus vector encodes a replication-defective adenovirus and comprises a mutated genome with a partial or complete (preferably, a complete) deletion of the E1A coding region (e.g., SEQ ID NO: 17), E1B coding region (e.g., SEQ ID NO: 18), and E2B polymerase coding region (for example, SEQ ID NO: 23), and includes one or more heterologous nucleotide sequences. The heterologous nucleotide sequences can be introduced into any region of the genome (e.g., the amino or carboxy-termini). In a specific embodiment, a heterologous nucleotide sequence is introduced into one of the deleted adenoviral coding regions, such as the E1A or E2B coding region, of the mutated adenoviral genome. In a preferred embodiment, the recombinant adenovirus vector encodes a replication-defective adenovirus and comprises a mutated genome with a partial or complete (preferably, a complete) deletion of the E1A coding region (e.g., SEQ ID NO: 17), E1B coding region (e.g., SEQ ID NO:18), E2B polymerase coding region (e.g., SEQ ID NO: 23), and E3 coding region, and includes a heterologous nucleotide sequence in the deleted E3 coding region.

In accordance with the invention, the recombinant adenovirus (rAd) vectors comprise an adenoviral genome or a portion thereof obtained and/or derived from any adenoviridae or a combination of adenoviridae. In a preferred embodiment, the recombinant adenovirus vectors comprise an adenoviral genome or portion thereof obtained and/or derived from a human adenoviridae. In another preferred embodiment, the recombinant adenovirus vectors comprise an adenoviral genome or portion thereof obtained and/or derived from the human adenovirus serotype 2 or 5.

In accordance with the invention, any recombinant adenovirus may be produced and/or propagated utilizing the rAd production cell lines described herein. In the preferred embodiment of the invention, the recombinant adenoviruses are derived from the human adenoviridae. In another preferred embodiment of the invention, the recombinant adenovirus is derived from the human adenovirus serotype 2 or 5. In a specific embodiment, the recombinant adenovirus is a replication-defective adenovirus and comprises a mutated genome with a partial or complete (preferably, a complete) deletion of the E1A coding region (e.g., SEQ ID NO: 17) and E1B coding region (e.g., SEQ ID NO: 18), and may include one or more additional heterologous genes. In a preferred practice of the invention, the recombinant adenovirus is a replication-defective adenovirus and comprises a mutated genome with a partial or complete (preferably, a complete) deletion of the E1A coding region (e.g., SEQ ID NO: 17), E1B coding region (e.g., SEQ ID NO: 18), and E2B polymerase coding region (for example, SEQ ID NO: 23), and includes one or more heterologous nucleotide sequences. The preferred recombinant adenoviruses of the present invention comprise viral DNA sequences that lack any homology with the adenoviral DNA sequences in the rAd production cell line, which reduces the possibility of the viral genome recombining with the cellular DNA to produce RCAs.

In one embodiment, the present invention provides a method for producing and/or propagating recombinant adenoviruses comprising: (a) infecting human cells, said human cells comprising stably integrated nucleic sequences comprising: (i) a first expression cassette comprising a promoter active in said human cell operably linked to a nucleic acid sequence encoding adenoviral E1A proteins deficient in binding to p300 protein family members and pRb protein family members, wherein said proteins are expressed in said human cell; and (ii) a second expression cassette comprising a promoter active in said human cell operably linked to a nucleic acid sequence encoding an adenoviral E1B protein, wherein said E1B protein comprises an E1B-55K protein but not an E1B-19K protein, wherein said E1B-55K protein is expressed in said human cell; (b) culturing said infected cells under conditions so as to permit replication of the viral genome in the cells; (c) harvesting said cells; and (d) recovering said recombinant adenovirus, wherein steps (c) and (d) are optional.

Also provided is the above method, wherein said E1A proteins comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. Also provided is the above method, wherein said E1A proteins comprise: (a) said first deletion corresponding to amino acid residues 4-25 of said E1A 289R protein (dl1101) and amino acid residues 4-25 of said E1A 243R protein (dl1101); and (b) said second deletion corresponding to amino acid residues 111-123 (dl1107) of said E1A 289R protein and amino acid residues 111-123 (dl1107) of said E1A 243R protein.

Also provided are the above methods, wherein said cell is derived from the group consisting of an established cell line, a tumor cell line, an A549 cell line, and a HeLa cell line. Also provided are the above methods, wherein said cells are designated SL0003, deposited with the ATCC under accession number PTA-6231.

Also provided are the above methods, wherein the first expression cassette comprises the nucleic acid sequence set forth in SEQ ID NO: 27; and, the above methods, wherein the second expression cassette comprises the nucleic acid sequence set forth in SEQ ID NO: 15. In specific embodiment, the first expression cassette comprises the nucleic acid sequence set forth in SEQ ID NO: 1; and, the above methods, wherein the second expression cassette comprises the nucleic acid sequence set forth in SEQ ID NO: 2. Also provided are the above methods, wherein the recombinant adenovirus comprises deletions of the E1A and E1B coding regions. Also provided are the above methods, wherein the recombinant adenovirus is replication-defective. Also provided are the above methods, wherein the recombinant adenovirus further comprises a heterologous gene.

In one embodiment, the present invention provides a method for producing and/or propagating recombinant adenoviruses comprising: (a) infecting human cells, said human cells comprising stably integrated nucleic sequences comprising: (i) a first expression cassette comprising a promoter active in said human cell operably linked to a nucleic acid sequence encoding adenoviral E1A proteins deficient in binding to p300 protein family members and pRb protein family members, wherein said proteins are expressed in said human cell; (ii) a second expression cassette comprising a promoter active in said human cell operably linked to a nucleic acid sequence encoding an adenoviral E2B polymerase protein, wherein said E2B polymerase protein is expressed in said human cell; and (iii) a third expression cassette comprising a promoter active in said human cell operably linked to a nucleic acid sequence encoding adenoviral E1B-55K and E1B-19K proteins, wherein said proteins are expressed in said human cell; (b) culturing said infected cells under conditions so as to permit replication of the viral genome in the cells; (c) harvesting said cells; and (d) recovering said recombinant adenovirus, wherein steps (c) and (d) are optional.

Also provided is the above method, wherein said E1A proteins comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. Also provided is the above method, wherein said E1A proteins comprise: (a) said first deletion corresponding to amino acid residues 4-25 of said E1A 289R protein (dl1101) and amino acid residues 4-25 of said E1A 243R protein (dl1101); and (b) said second deletion corresponding to amino acid residues 111-123 (dl1107) of said E1A 289R protein and amino acid residues 111-123 (dl1107) of said E1A 243R protein.

Also provided are the above methods, wherein said cell is derived from the group consisting of an established cell line, a tumor cell line, an A549 cell line, and a HeLa cell line. Also provided are the above methods, wherein said cells are designated SL0006, deposited with the ATCC under accession number PTA-6663.

Also provided are the above methods, wherein the first expression cassette comprises the nucleic acid sequence set forth in SEQ ID NO: 27, the second expression cassette comprises the nucleic acid sequence set forth in SEQ ID NO: 23 and/or the second expression cassette comprises the nucleic acid sequence set forth in SEQ ID NO: 18. In a specific embodiment, the first expression cassette comprises the nucleic acid sequence set forth in SEQ ID NO: 1, the second expression cassette comprises the nucleic acid sequence set forth in SEQ ID NO: 20 and/or the second expression cassette comprises the nucleic acid sequence set forth in SEQ ID NO: 19. Also provided are the above methods, wherein the recombinant adenovirus comprises deletions of the E1A, E2b polymerase, and E1B coding regions. Also provided are the above methods, wherein the recombinant adenovirus is replication-defective. Also provided are the above methods, wherein the recombinant adenovirus further comprises a heterologous gene.

The recombinant adenoviruses of the invention can be used in vitro to express proteins, polypeptides and peptides of interest. The recombinant adenoviruses of the invention can also be used in gene therapy. Further, the recombinant adenovirus of the present invention may be used to immunize a subject. The antibodies generated against an antigen by immunization with a recombinant adenovirus may used in diagnostic immunoassays, passive immunotherapy, and the generation of anti-idiotypic antibodies.

The present invention also provides a plasmid system for producing a rAd production cell for the production and/or propagation of recombinant adenovirus. In one embodiment, the invention provides a plasmid system for producing and/or propagating a human cell for the production and/or propagation of recombinant adenovirus comprising in separate containers: (a) a first expression cassette comprising a promoter active in said human cell operably linked to a nucleic sequence encoding adenoviral E1A proteins deficient in binding to p300 protein family members and pRb protein family members; and (b) a second expression cassette comprising a promoter active in said human cell operably linked to a nucleic acid sequence encoding an adenoviral E1B protein, wherein said E1B protein comprises an E1B-55K protein but not an E1B-19K protein. Also provided is the above plasmid system wherein said E1A proteins comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. Further provided is the above plasmid system, wherein said E1A proteins comprise: (a) said first deletion corresponding to amino acid residues 4-25 of said E1A 289R protein (dl1101) and amino acid residues 4-25 of said E1A 243R protein (dl1101); and (b) said second deletion corresponding to amino acid residues 111-123 (dl1107) of said E1A 289R protein and amino acid residues 111-123 (dl1107) of said E1A 243R protein. Also provided are the above plasmid systems, wherein said cell is derived from the group consisting of an established cell line, a tumor cell line, an A549 cell line, and a HeLa cell line. Also provided are the above plasmid systems, wherein the first expression cassette comprises the nucleic acid sequence set forth in SEQ ID NO: 26. In a specific embodiment, the first expression cassette comprises the nucleic acid sequence set forth in SEQ ID NO: 1. Also provided are the above plasmid systems, wherein the second expression cassette comprises the nucleic acid sequence set forth in SEQ ID NO: 15. In a specific embodiment, the second expression cassette comprises the nucleic acid sequence set forth in SEQ ID NO: 2.

The present invention further provides a plasmid system for producing a human cell for the production and/or propagation of recombinant adenovirus comprising in separate containers: (a) a first expression cassette comprising a promoter active in said human cell operably linked to a nucleic sequence encoding adenoviral E1A proteins deficient in binding to p300 protein family members and pRb protein family members; (b) a second expression cassette comprising a promoter active in said human cell operably linked to a nucleic acid sequence encoding an adenoviral E2B polymerase protein; and (c) a third expression cassette comprising a promoter active in said human cell operably linked to a nucleic acid sequence encoding adenoviral E1B-55K and E1B-19K proteins. Also provided is the above plasmid system wherein said E1A proteins comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. Further provided is the above plasmid system, wherein said E1A proteins comprise: (a) said first deletion corresponding to amino acid residues 4-25 of said E1A 289R protein (dl1101) and amino acid residues 4-25 of said E1A 243R protein (dl1101); and (b) said second deletion corresponding to amino acid residues 111-123 (dl1107) of said E1A 289R protein and amino acid residues 111-123 (dl1107) of said E1A 243R protein. Also provided are the above plasmid systems, wherein said cell is derived from the group consisting of an established cell line, a tumor cell line, an A549 cell line, and a HeLa cell line. Also provided are the above plasmid systems, wherein the first expression cassette comprises the nucleic acid sequence set forth in SEQ ID NO: 26. In a specific embodiment, the first expression cassette comprises the nucleic acid sequence set forth in SEQ ID NO: 1. Also provided are the above plasmid systems, wherein the second expression cassette comprises the nucleic acid sequence set forth in SEQ ID NO: 23. In a specific embodiment, the second expression cassette comprises the nucleic acid sequence set forth in SEQ ID NO: 20. Also provided are the above plasmid systems, wherein the third expression cassette comprises the nucleic acid sequence set forth in SEQ ID NO: 25. In a specific embodiment, the third expression cassette comprises the nucleic acid sequence set forth in SEQ ID NO: 19.

3.1 Terminology

As used herein, the term "A549" refers to a human lung carcinoma cell line which is commonly known in the art. In one embodiment, the A549 parental cell line used to produce the E1-complementing cell line is ATCC strain CCL-185.

As used herein, the term "adenovirus" refers to viruses of the genus adenoviridiae. The term "recombinant adenovirus" refer to viruses of the genus adenoviridiae capable of infecting a cell whose viral genomes have been modified through conventional recombinant DNA techniques. The term recombinant adenovirus also includes chimeric (or even multimeric) vectors, i.e. vectors constructed using complementary coding sequences from more than one viral subtype.

As used herein, the term "adenoviridae" refers collectively to animal adenoviruses of the genus mastadenovirus including but not limited to human, bovine, ovine, equine, canine, porcine, murine and simian adenovirus subgenera. In particular, human adenoviruses includes the A-F subgenera as well as the individual serotypes thereof. A-F subgenera including but not limited to human adenovirus types 1, 2, 3, 4, 4a, 5, 6, 7, 7a, 7d, 8, 9, 10, 11 (Ad11A and Ad11P), 12, 13, 14, 15, 16, 17, 18, 19, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91.

As used herein, the term "culturing under conditions to permit replication of the viral genome" means maintaining the conditions for the rAd complementation cell line infected with recombinant adenovirus and/or transfected with rAd vector so as to permit the virus to propagate in the cell. It is desirable to control conditions so as to maximize the number of viral particles produced by each cell. Consequently it will be necessary to monitor and control reaction conditions such as temperature, dissolved oxygen, pH, etc. Commercially available bioreactors such as the CelliGen Plus Bioreactor (commercially available from New Brunswick Scientific, Inc. 44 Talmadge Road, Edison, N.J.) have provisions for monitoring and maintaining such parameters. Optimization of infection, transfection and culture conditions will vary somewhat, however, conditions for the efficient replication and production of virus may be achieved by those of skill in the art taking into consideration, for example, the known properties of the producer cell line, properties of the virus and the type of bioreactor.

As used herein, the terms "a deficiency in a gene" or "a deficiency in a gene function" is a type of mutation which serves to impair or eliminate the function of the gene whose nucleic acid sequences was mutated in whole or in part.

As used herein, the term "deficient in binding" refers to a gene product forming a complex with less than 50% of the thermodynamic stability of the complex of the wild type gene product to its substrate under physiological conditions. For example, a 13S gene product which contains a deletion in the p300 binding domain would bind to p300 protein with less than 50% of the thermodynamic stability of the wild-type 13S protein. The thermodynamic stability of binding can readily be determined by conventional assay techniques to determine equilibrium binding constants under physiological conditions.

As used herein, the term "E1A gene" refers to the immediate early gene of the adenovirus genome first transcribed following infection. This genomic sequence represents at least the transcription of five mRNAs encoding the 9S, 10S, 11S, 12S and 13S proteins. The 12S and 13S proteins are expressed in the early phase following infection while the 9S, 10S and 11S proteins are expressed later in the adenovirus cycle. The 12S and 13S proteins have 243 and 289 amino acids, respectively. The 12S and 13S proteins are also known as 243R and 289R proteins, respectively. There are three conserved regions in the E1A genomic sequence referred to as conserved region ("CR")-1, CR2 and CR3. CR1 represents amino acids 41-80 of the 12S and 13S proteins. CR2 represents amino acids 121-139 of the 12S and 13S sequence.

GenBank® deposits of the complete human adenovirus type 5 genome are available, see for example, AY339865 and AC 000008. The human adenovirus type 5, 289R, wild type, amino acid sequence is defined by SEQ ID NO: 4. The human adenovirus type 5, 243R, wild type, amino acid sequence is defined by SEQ ID NO: 6. GenBank® deposits of the human adenovirus type 5, 289R, wild type, amino acid sequence are also available, see, for example, AP 000197, AY339865 and AC 00008. GenBank® deposits of the human adenovirus type 5, 243R, wild type, amino acid sequence are also available, see, for example, AY339865.

As used herein, the term "expression cassette" is used herein to define a nucleotide sequence capable of directing the transcription and translation of a heterologous coding sequence and the heterologous coding sequence to be expressed. An expression cassette comprises a regulatory element operably linked to a heterologous coding sequence so as to achieve expression of the protein product encoded by said heterologous coding sequence in the cell.

As used herein, the term "helper adenovirus nucleic acid sequence(s)" refers to a nucleic acid sequence(s) that: (i) provides viral functions for the replication of a recombinant adenovirus vector and/or its packaging into infectious virions; and (ii) is (are) not replicated or assembled into viral particles to a measurable degree.

As used herein, the term "heterologous" in the context of nucleic acid sequences, amino acid sequences and antigens refers to nucleic acid sequences, amino acid sequences and antigens that are foreign and are not naturally found associated with a particular adenovirus.

As used herein, the term "infecting" means exposing the recombinant adenovirus to the rAd production cell line under conditions so as to facilitate the infection of the producer cell with the recombinant adenovirus. In cells which have been infected by multiple copies of a given virus, the activities necessary for viral replication and virion packaging are cooperative. Thus, it is preferred that conditions be adjusted such that there is a significant probability that the cells are multiply infected with the virus. An example of a condition which enhances the production of virus in the cell is an increased virus concentration in the infection phase. However, it is possible that the total number of viral infections per cell can be overdone, resulting in toxic effects to the cell. Consequently, one should strive to maintain the infections in the virus concentration in the range of $10^6$ to $10^{10}$, preferably about $10^9$, virions per ml. Chemical agents may also be employed to increase the infectivity of the cell line. For example, the present invention provides a method to increase the infectivity of cell lines for viral infectivity by the inclusion of a calpain inhibitor. Examples of calpain inhibitors useful in the practice of the present invention include calpain inhibitor 1 (also known as N-acetyl-leucyl-leucyl-norleucinal, commercially available from Boehringer Mannheim). Calpain inhibitor 1 has been observed to increase the infectivity of cell lines to recombinant adenovirus.

As used herein, the term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic sequences may be of variable lengths, some polynucleotide elements may be operably linked but not directly flanked and may even function in trans from a different allele or chromosome.

As used herein, the term "p300 protein family members" refers the proteins which associate with the amino terminus of E1A including p300 and CBP. In particular p300 co-activates the activity of the transactivating genes, Myb and C/EBP (Mink, et al. (1997) Molecular and Cellular Biology 17:6609-6617). The human p300 protein is known in the art and is publicly available from the Swiss-Prot database under accession number Q09472, its corresponding mRNA is available from GenBank under accession number U01877 deposited Jun. 6, 1994 and is described in Eckner, et al. (1994) Genes Dev. 8:869-884.

As used herein, the term "regulatory element" refers to promoters, enhancers, transcription terminators, insulator regions, silencing region, polyadenylation sites, and the like. The term "promoter" is used in its conventional sense to refer to a nucleotide sequence at which the initiation and rate of transcription of a coding sequence is controlled. The promoter contains the site at which RNA polymerase binds and also contains sites for the binding of regulatory factors (such as repressors or transcription factors). Promoters may be naturally occurring or synthetic. When the vector to be employed is a viral vector, the promoters may be endogenous to the virus or derived from other sources. The regulatory elements may be arranged so as to allow, enhance or facilitate expression of the transgene only in a particular cell type. For example, the expression cassette may be designed so that the transgene is under control of a promoter which is constitutively active, or temporally controlled (temporal promoters), activated in response to external stimuli (inducible), active in particular cell type or cell state (selective) constitutive promoters, temporal viral promoters or regulatable promoters.

As used herein, the term "recombinant adenovirus vector(s)" refers to a vector construct comprising adenoviral nucleotide sequences and optionally, one or more heterologous nucleotide sequences. In a preferred embodiment, the recombinant adenovirus vectors comprise adenoviral nucleotide sequences that lack any homology to the helper adenovirus nucleic acid sequences. In another preferred embodiment, the recombinant adenovirus vector encodes a replication-defective adenovirus. In accordance with this embodiment, the recombinant adenovirus vector may be engineered to comprise a mutated adenovirus genome by, e.g., introducing one or more mutations in an adenovirus genome (e.g., introducing deletions in one or more coding regions for adenoviral proteins).

As used herein, the terms, "rAd production cell line", "rAd complementation cells", and "rAd complementation cell lines" are synonyms and mean a cell able to propagate recombinant adenoviruses by providing viral functions for replication of a recombinant adenovirus and/or its packaging into infectious virions.

As used herein, the term "Rb protein family members" refers to the retinoblastoma gene product (pb105), p107 and p130. The retinoblastoma gene is well characterized in the art. The amino acid sequence of human Rb is available from GenBank under accession Number 190959 deposited Jul. 12, 1995 and the mRNA sequence is available from GenBank under accession number M15400 and is described in Lee, et al. (1988) PNAS (USA) 85:6017-6021.

As used herein, the term "stably integrated" means, with respect to an exogenous nucleic acid sequence, that such sequence is integrated into the genome of the cell such that successive generations of the cell retains the exogenous nucleic acid sequence.

As used herein, the term "transfection" or "transformation" means the introduction of a nucleic acid into a cell. A host cell that receives the introduced DNA or RNA has been "transformed" and is a "transformant" or a "clone." Examples of transformation methods which are very well known in the art include liposome delivery, electroporation, $CaPO_4$ transformation, DEAE-Dextran transformation, microinjection and viral infection.

As used herein, the term "transformation" may also refer to, in the context of in vitro animal cell culture, a permanent alteration of the cell phenotype that is presumed to occur via an irreversible genetic change. A "transformed cell" usually is a cell that, among other potential phenotypic characteristics, has an infinite or a significantly (or greatly) extended lifespan when compared with the cells of the finite or primary cell line from which it arose. The context in which the term is used will govern the meaning.

SV40 poly A signal: Start:3551 End:3760
pUC19 sequence (448-2622): Start:3900 End:6074
Col E1 origin: Start:4083 End:4606
Ampicillin resistance gene: complement (5090.5950)
E1A 12S CDS N-term: Start:633 End:944
E1A proteins start (ATG): Start:633 End:635
E1A 13S CDS N-term: Start:633 End:1082
Splice donor for E1A 12s mRNA: Start:942 End:942
Splice donor for E1A 13s mRNA: Start: 1080 End:1080
E1A 12S/13S CDS C-term CDS: Start:1199 End:1513
Stop TAA for E1A 32k/27k: Start:1511 End:1513
dl1110 mutation (amino acids 4-25 of WT are deleted): Start:644 End:645
dl1107 mutation (amino acids 111-123 of WT are deleted): Start:896 End:897

Figure 3:
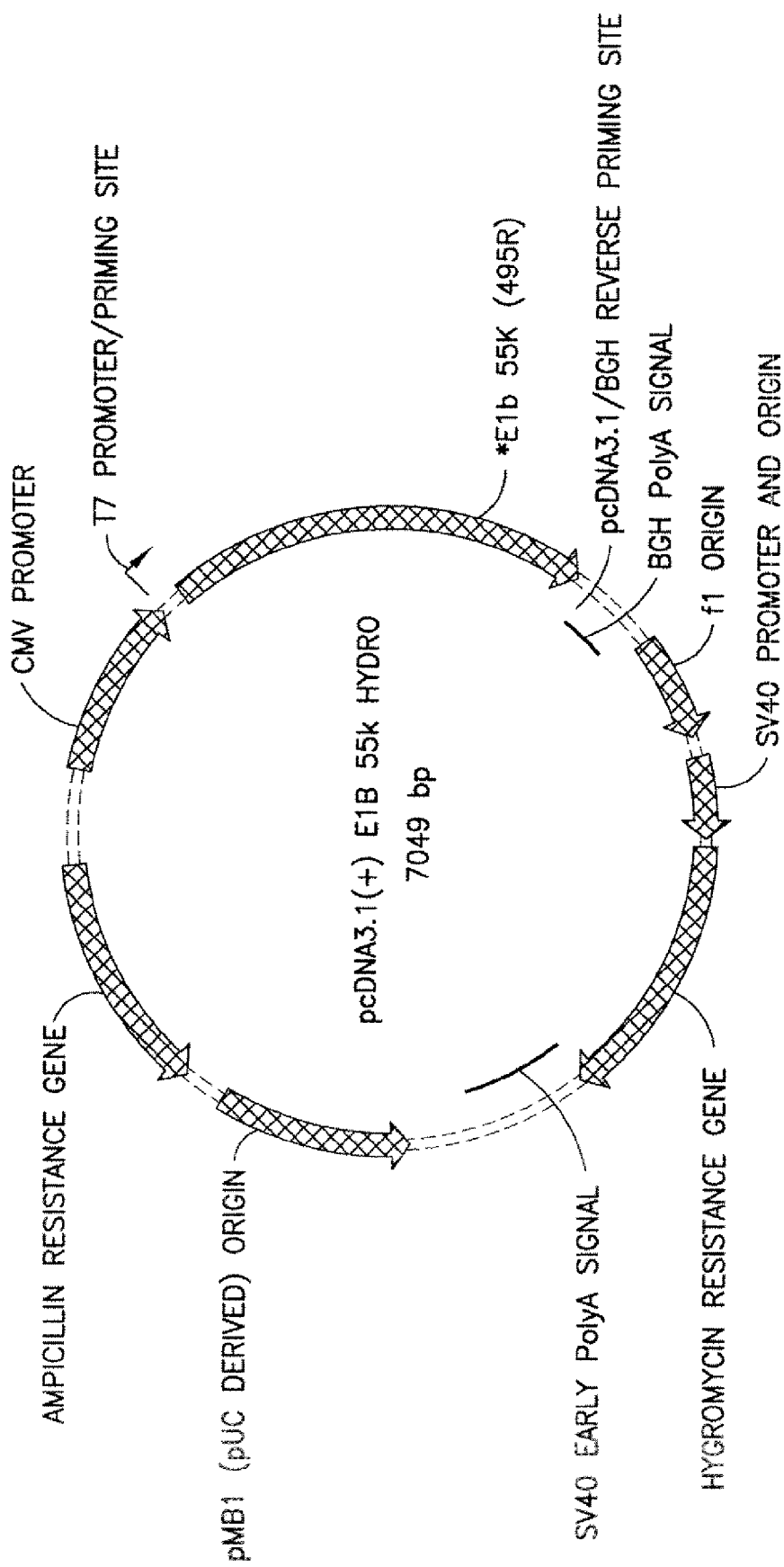

FIG. 3. Plasmid map of pcDNA3.1(+)E1B-55k Hygro.
CMV promoter: Start: 209 End: 863
T7 promoter/priming site: Start:863 End: 882
pcDNA3.1 BGH reverse priming site: Start:2470 End:2487
BGH poly A signal: Start:2469 End:2683
f1 origin: Start:2746 End:3159
SV40 promoter and origin: Start:3224 End:3548
Hygromycin resistance gene CDS: Start:3566 End:4589
SV40 early poly A signal: Start:4602 End:4974
PMB1 (pUC derived) origin: complement (5234 . . . 5904)
Ampicillin resistance gene: complement (6049 . . . 6909)
E1B 55K (495R) CDS: Start:942 End:2430

Figure 4:
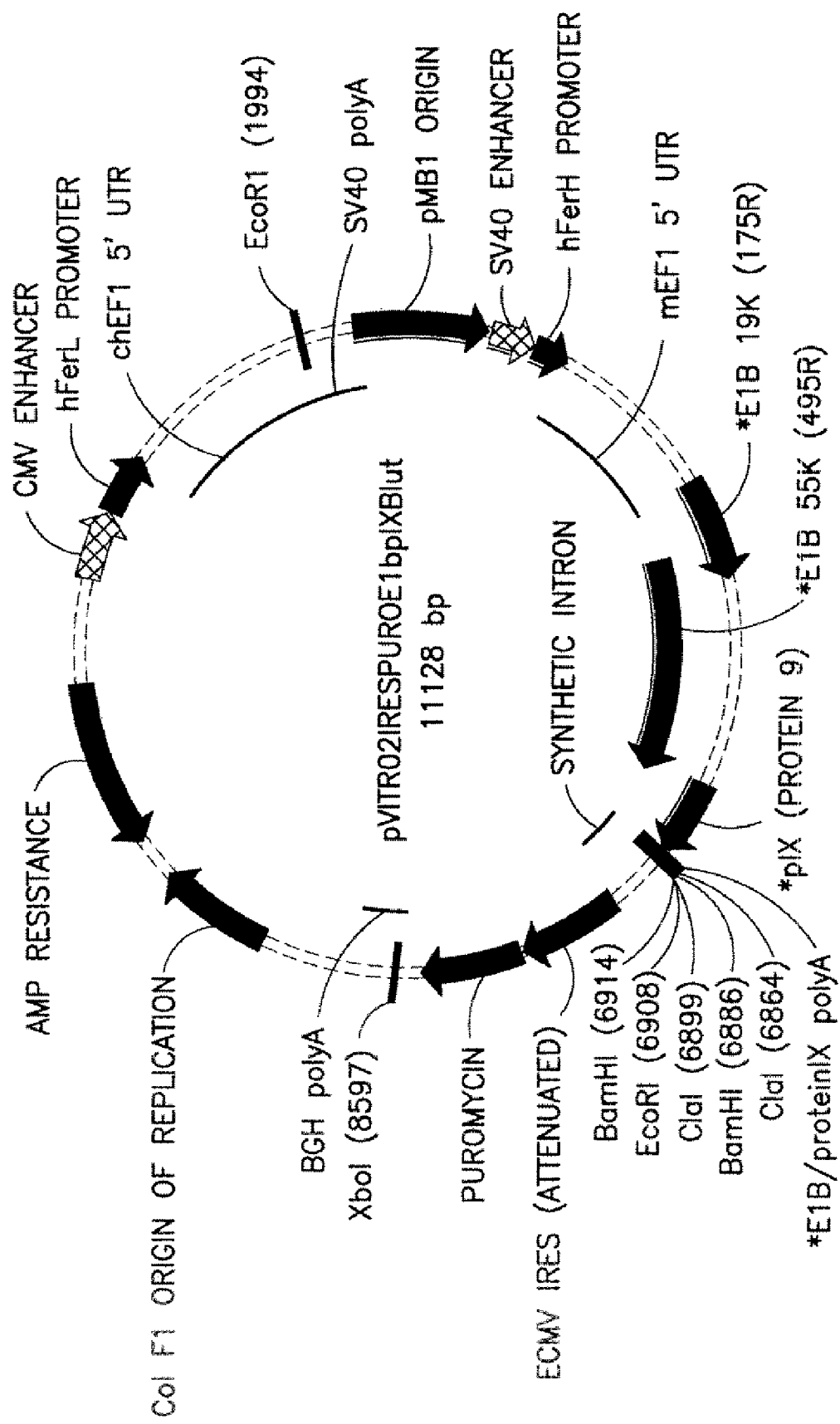

FIG. 4. Plasmid map of pVITRO21RESPuroE1b: Plasmid encoding the entire E1b and pIX coding sequence driven by the human ferritin heavy subunit promoter and SV40 enhancer with a puromycin resistance gene for cell selection following an IRES element downstream of the adenovirus sequence.

Figure 5:
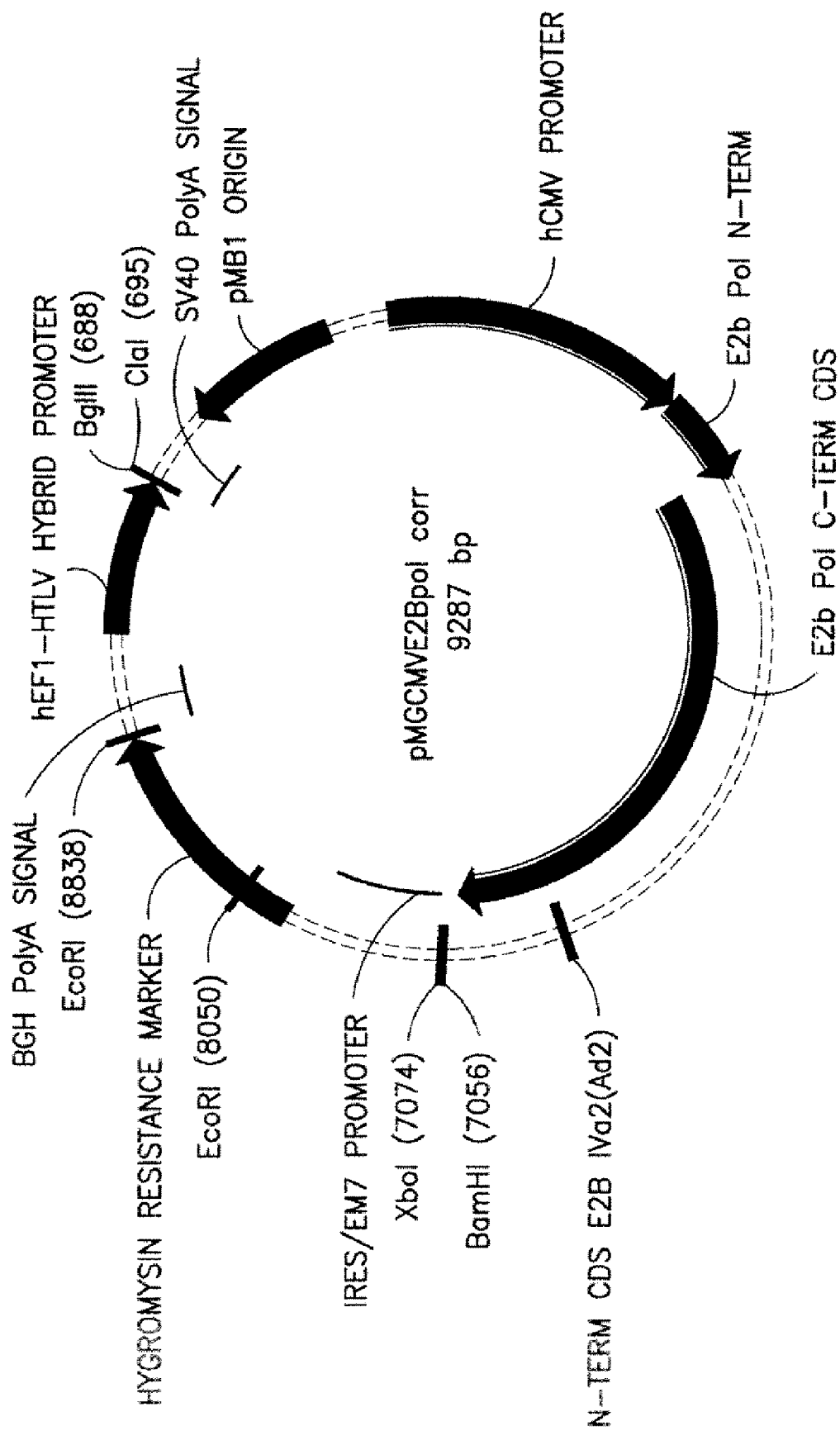

FIG. 5. Plasmid map of pMGCMVE2Bpol. Plasmid using a CMV promoter to drive expression of the full-length E2b polymerase coding sequence, followed by an IRES sequence and the hygromycin resistance gene which was used for selection.

Figure 6:
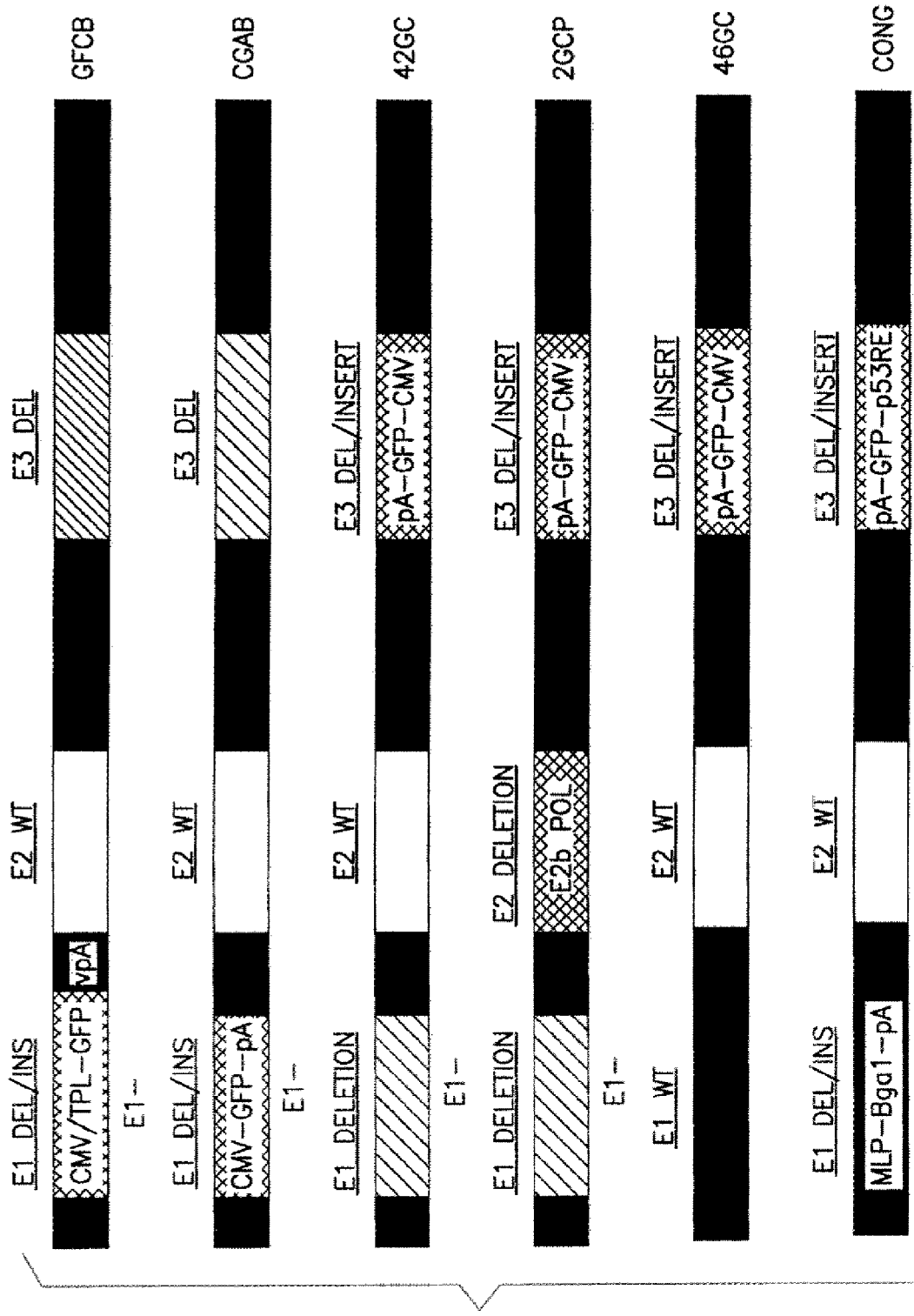

FIG. 6. Schematic representation of viral constructs. Similarities and differences between viral constructs in the E1, E2b, and E3 regions are indicated. CMV-GFP expression cassettes are inserted in the E1 region for GFCB and CGAB viruses, and as 5' to 3' orientation inserts in the E3 region for 42GC, 2GCP, and 46GC. CONG has expression cassettes in both the E1 and E3 regions as indicated. The 2GCP construct has a deletion in the E2b viral DNA polymerase region which prevents its expression. Further details can be found in Example 2.

FIG. 7. Expression of E2b polymerase in cells and effect on viral productivity of E2b polymerase deleted virus. Panel A) Western analysis of E2b polymerase protein from cellular lysates of isolated clones 3C4, 3C9 and 3D8 relative to non E2b polymerase complementing parental clone 4 and unmodified A549 cells. Lower portion of Western shows detection of β-actin protein, verifying equal total protein loading per lane. Panel B) Virus particles produced per cell infected with the E2b polymerase deleted 2GCP virus. Results plotted are from duplicate 10 cm plates of the indicated clones infected with $5 \times 10^8$ P/ml of purified 2GCP virus+/−standard deviation.

FIG. 8. E1b complementation and effects on viral productivity. Panel A) Pictures of GFP fluorescence from individual clones infected with either $5 \times 10^8$ P/ml of GFCB or CONG virus at 48 hours post-infection. Panel B) The ratio of GFP fluorescence as determined by Cytofluor analysis from CONG infected cells over the fluorescence from the same clone infected with GFCB virus is plotted. Panel C) Virus particles produced per cell from the indicated clones infected with $5 \times 10^8$ P/ml of purified 2GCP virus+/−standard deviation.

FIG. 9. Virus productivity in different cell lines and stability of clone 15M15. Panel A) Virus particles produced per cell from either parental clone 3D8 (no E1b complementation), selected clone 15M15 (with E1b complementation) or C7 cells (293 based, E2b polymerase complementing). Results plotted are from duplicate 10 cm plates of the indicated clones infected with $5 \times 10^8$ P/ml of purified 2GCP virus+/−standard deviation. Panel B) Viral productivity from clone 15M15. Cells were infected and harvested after 1, 5 or 10 passages of growth either in selection mix media containing hygromycin, puromycin and G418 or regular growth media without the selection drugs. Cells were infected with 2GCP virus at either $2 \times 10^9$ or $1 \times 10^9$ P/ml virus as indicated. Results are plotted from each sample as virus particles/cell. Panel C) E1a and E2b polymerase protein expression. Parallel infections as outlined in Panel B were harvested, and the levels of E1a and E2b polymerase protein from cellular lysates were analyzed by Western analysis. Samples were loaded at equal total protein concentration per well based on Bradford assay results.

Figure 10:
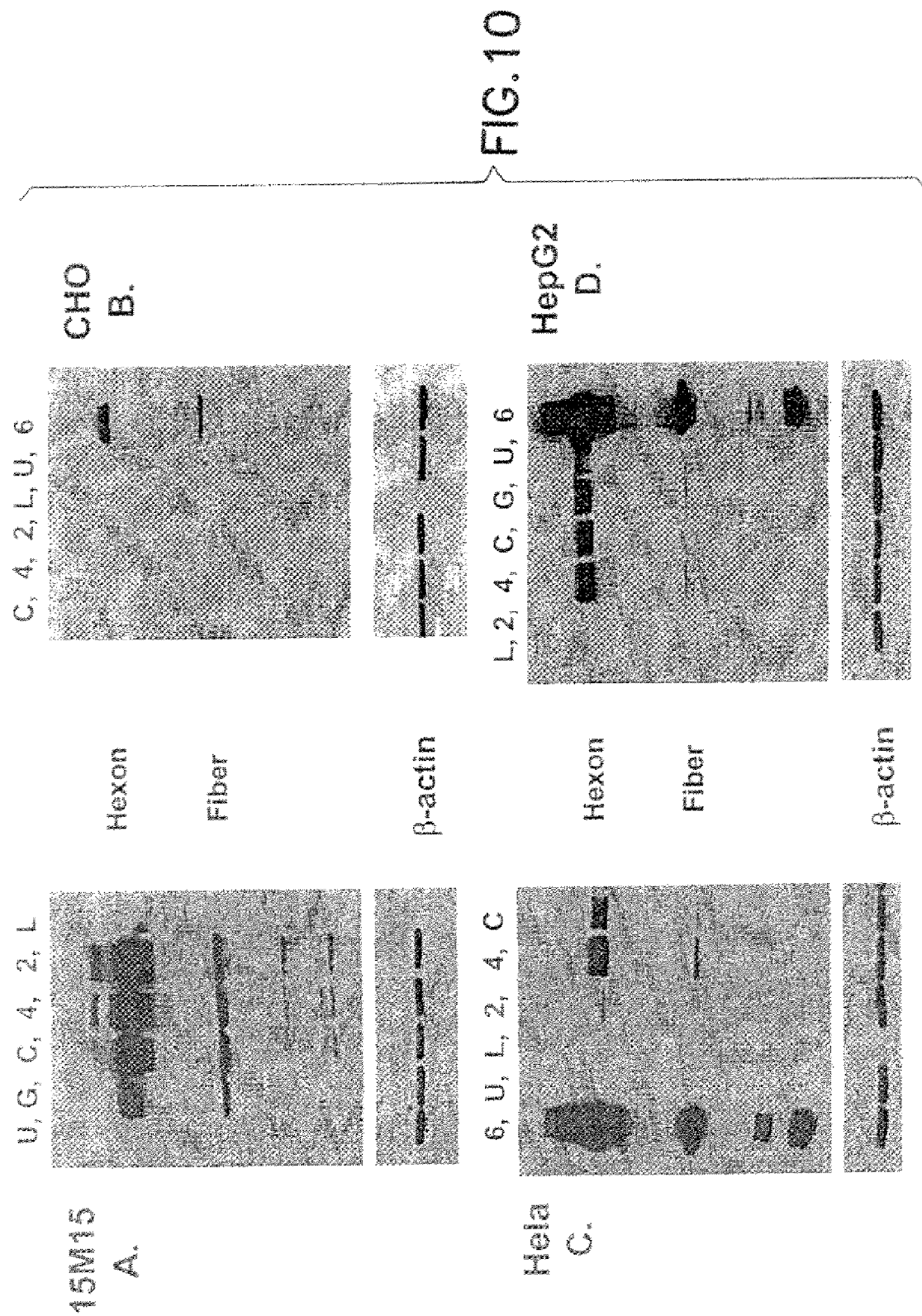
Figure 11A:
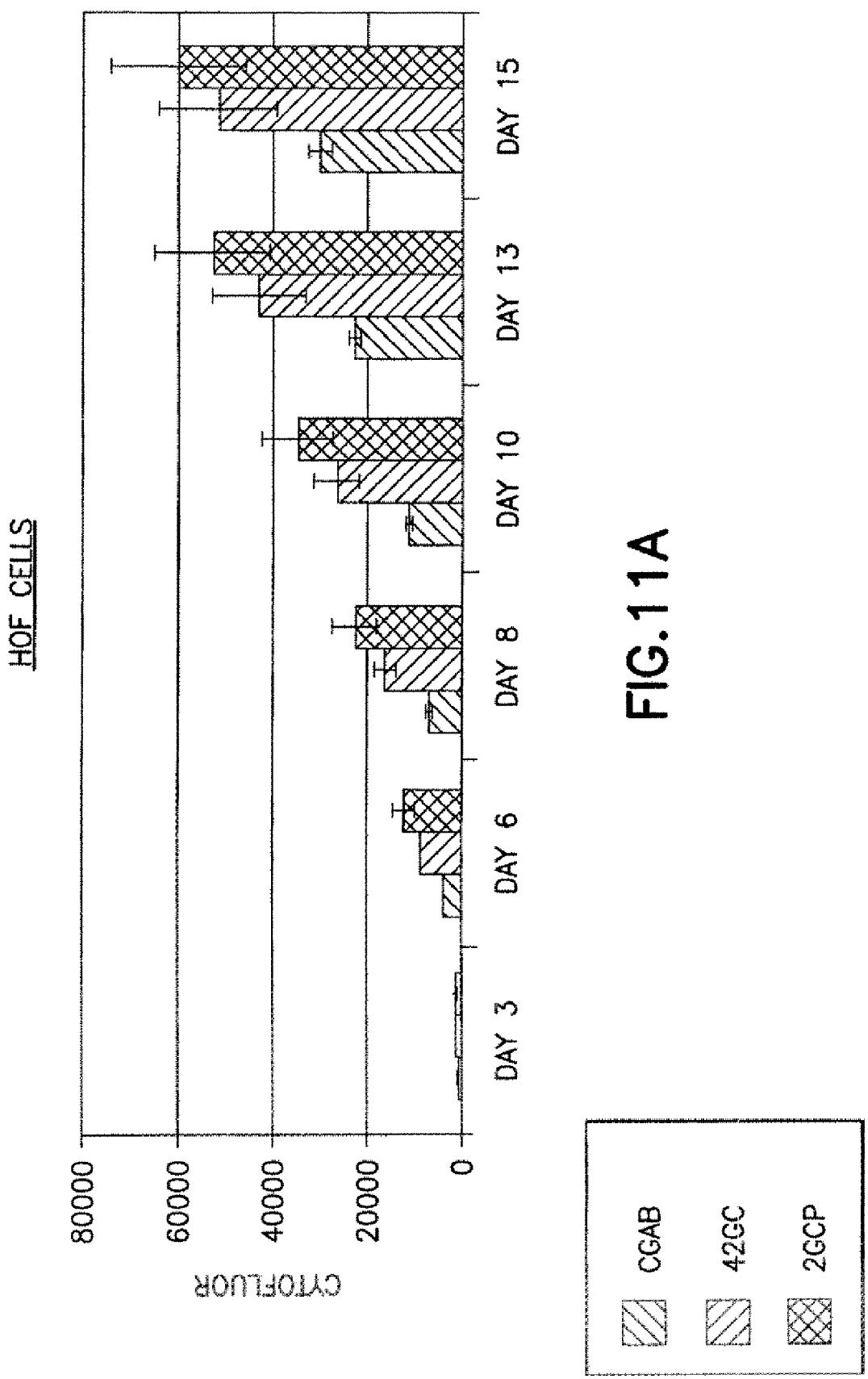
Figure 11B:
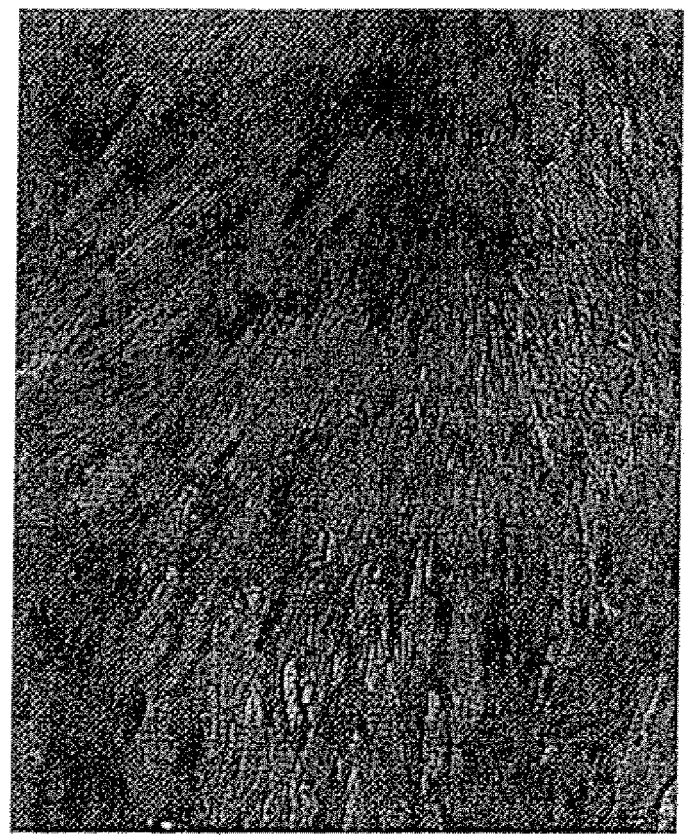
Figure 11B:
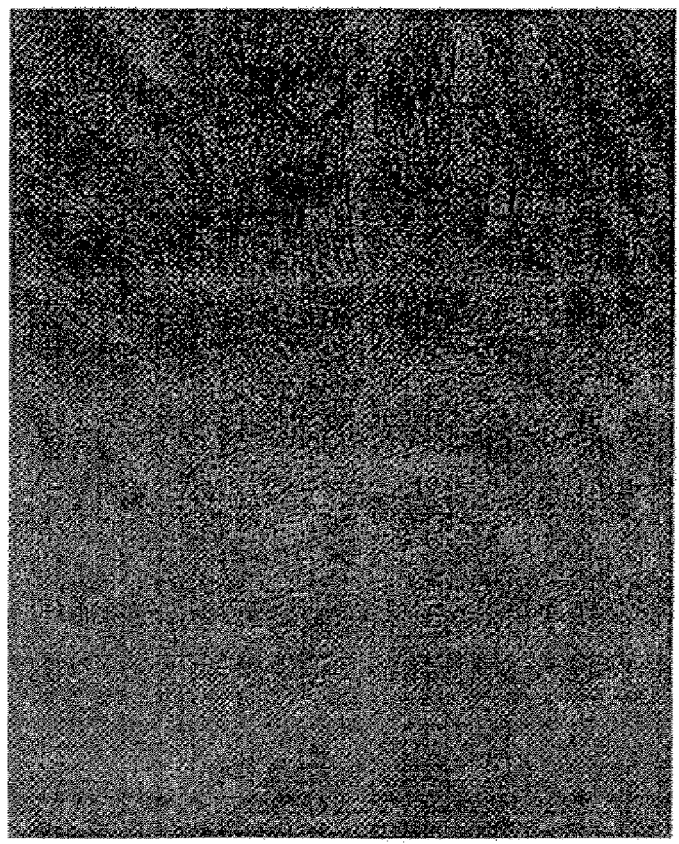
Figure 11C:
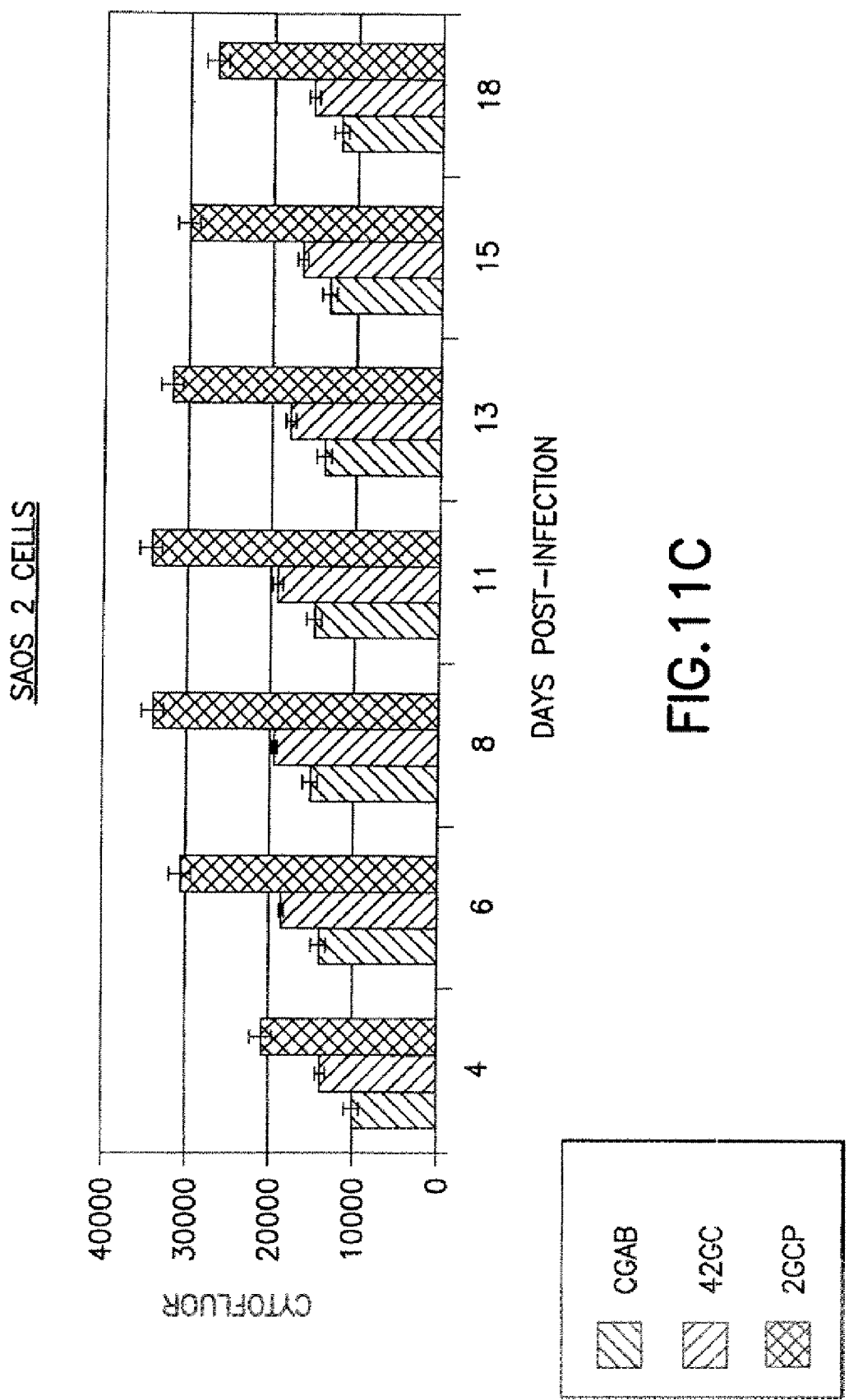
Figure 11D:
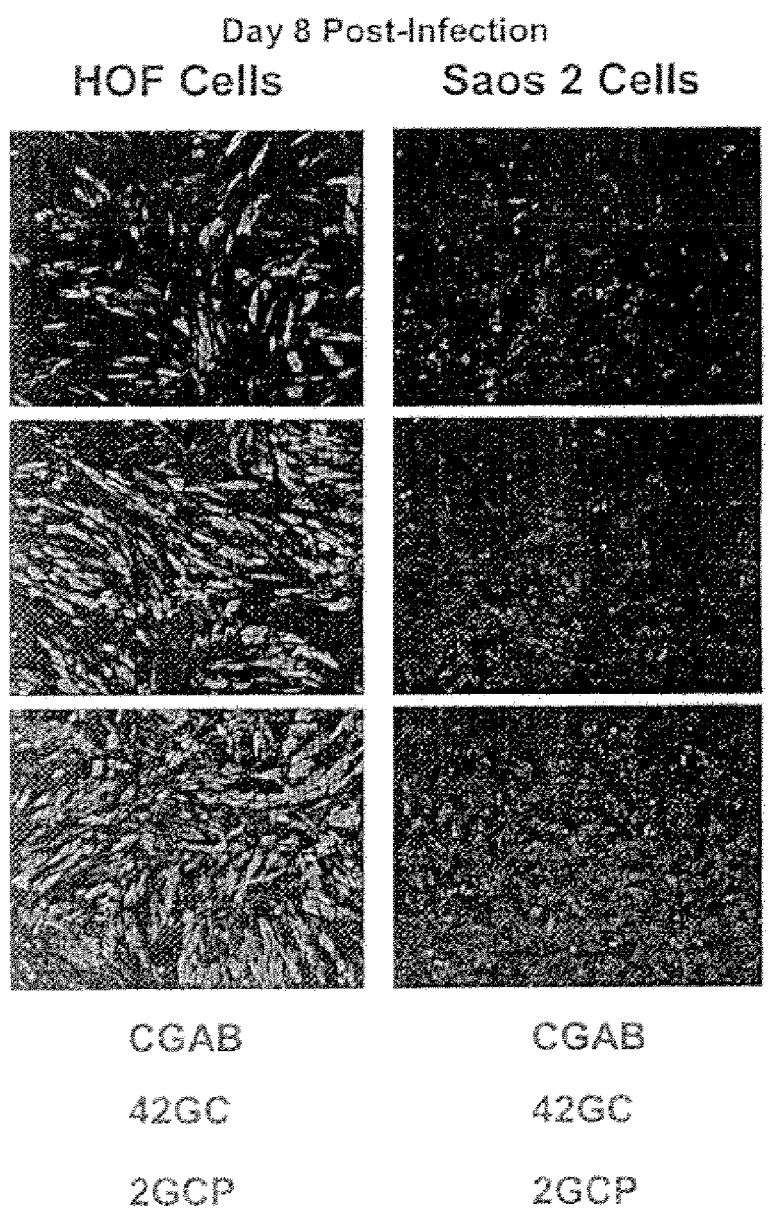
Figure 11E:
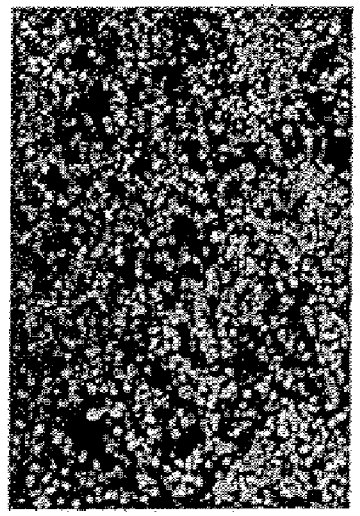
Figure 11E:
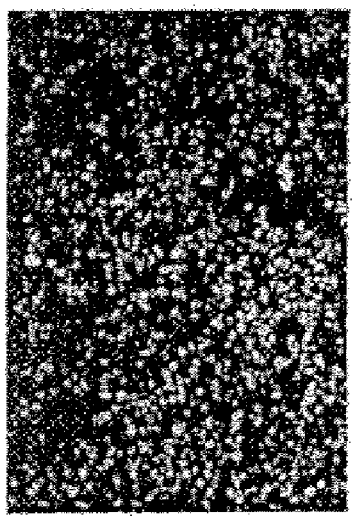
Figure 11E:
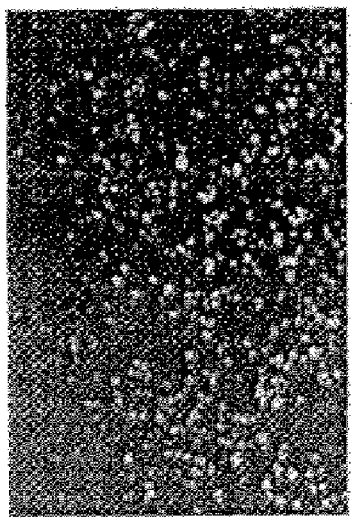
Figure 11F:
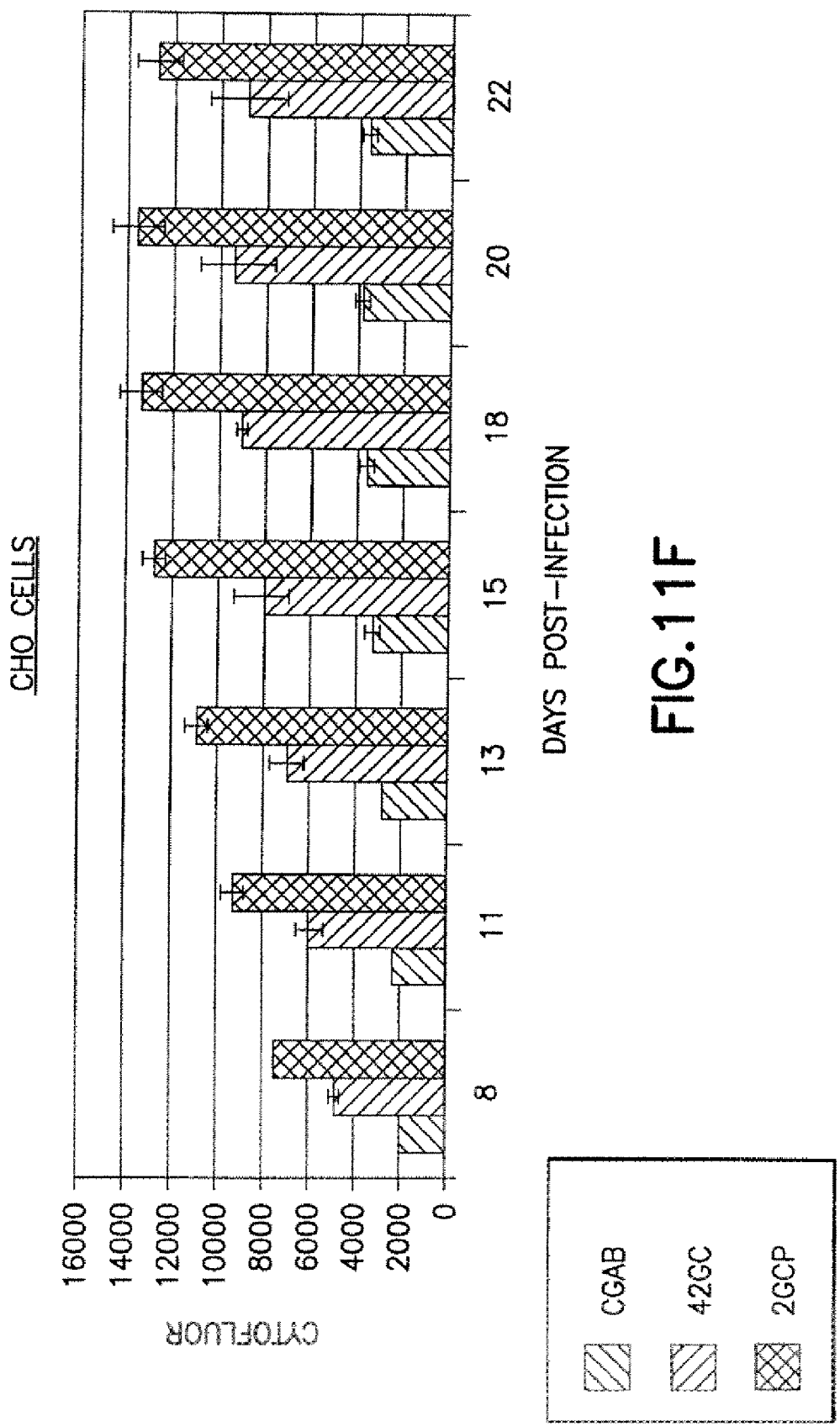

FIG. 10. Late Ad gene expression from infected cells. Panels A-D show the levels of hexon and fiber expressed from infected cells and detected by Western analysis. Panel A) Clone 15M15 production cell line. Panel B) Non-complementing CHO cell line. Panels C) and D) Partial E1a function complementing cell lines Hela and HepG2, respectively. Virus designation: G=GFCB, C=CGAB, 4=42GC, 2=2GCP, 6=6GCP, U=uninfected, L=ladder.

FIG. 11. In Vitro GFP Expression. Panels (A)-(D) GFP expression from HOF or Saos2 cells over time after infection with $5 \times 10^8$ Pml CGAB, 42GC, or 2GCP viruses. Graphs plot Cytofluor quantitation of GFP expression from duplicate infected wells +/− standard deviation, while photographs of infected cells 8 days post-infection are shown on the right. Panels (E)-(F) GFP expression from infected CHO cells as in Panels (A)-(D). Graphs plot Cytofluor quantitation of GFP expression from duplicate infected wells +/− standard deviation, while photographs above show infected cells 15 days post-infection.

DETAILED DESCRIPTION OF THE INVENTION

The present invention provides, inter alia, rAd production cell lines, methods for producing the rAd production cell lines, and methods for producing recombinant adenoviruses using the rAd production cell lines.

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

5.1 Helper Adenovirus Nucleic Acid Sequences

The helper adenovirus nucleic acid sequences of the present invention: (i) provide viral functions for the replication of a recombinant adenovirus construct and/or its packaging into infectious virions; and (ii) are not replicated or assembled into viral particles to a measurable degree. The helper adenovirus nucleic acid sequences can be obtained and/or derived from any adenoviridae or a combination of adenoviridae. In a preferred embodiment, the helper adenovirus nucleic acid sequences are obtained and/or derived from a human adenoviridae. In another preferred embodiment, the helper adenovirus nucleic acid sequences are obtained and/or derived from human adenovirus serotype 2 or 5. The nucleic acid sequences for adenovirus proteins can be obtained, e.g., from the GenBank database or a database like it, literature publications, or by routine cloning and sequencing.

In one embodiment, the helper adenovirus nucleic acid sequences include: (i) a nucleic acid molecule comprising a nucleotide sequence encoding adenoviral E1A proteins deficient in binding to p300 protein family members and pRb protein family members; and (ii) a nucleic acid molecule(s) comprising a nucleotide sequence(s) encoding an adenoviral E1B protein(s), such as E1B-55K and/or E1B-19K. In accordance with this embodiment, the helper adenovirus nucleic acid sequences may also include one, two or more of the following: (i) a nucleic acid molecule(s) comprising a nucleotide sequence(s) encoding an adenoviral E2 protein(s); (ii) a nucleic acid molecule(s) comprising a nucleotide sequence(s) encoding an adenoviral E4 protein(s); and/or (iii) a nucleic acid molecule comprising a nucleotide sequence encoding an adenoviral L4 100K protein. Non-limiting examples of adenoviral E2 proteins include E2A binding protein, E2B polymerase, E2B pre-terminal protein, and E2B IVa2 protein. Non-limiting examples of adenoviral E4 proteins include those encoded by open reading frame (ORF)-6, ORF3, and ORF6/7. Table 1 provides examples of the nucleotide and amino acid sequences of human adenovirus serotype 5 E1A proteins, E1B-55K protein, E1B-19K protein and E2B polymerase protein.

In certain embodiments, the helper adenovirus nucleic acid sequence includes a nucleic acid molecule comprising: (i) a nucleotide sequence encoding adenoviral E1A proteins deficient in binding to p300 protein family members and pRb protein family members; and (ii) a nucleotide sequence(s) encoding an adenoviral E1B protein(s), such as E1B-55K and/or E1B-19K. In accordance with these embodiments, the nucleic acid sequence may also include one, two or more of the following: (i) a nucleotide sequence(s) encoding an adenoviral E2 protein(s); (ii) a nucleotide sequence(s) encoding an adenoviral E4 protein(s); and/or (iii) a nucleotide sequence encoding an adenoviral L4 100K protein.

In certain embodiments, a helper adenovirus nucleic acid sequence encodes a fusion or chimeric protein product comprising an adenoviral protein joined via a peptide bond to a heterologous protein sequence. Such chimeric products can be made by ligating the appropriate nucleic acid sequences encoding the desired amino acids to each other by methods known in the art, in the proper coding frame, and expressing the chimeric products in a suitable host by methods commonly known in the art.

In a specific embodiment, the helper adenovirus nucleic acid sequences include: (i) a nucleic acid molecule comprising a nucleotide sequence encoding adenoviral E1A proteins deficient in binding to p300 protein family members and pRb protein family members; and (ii) a nucleic acid molecule comprising a nucleotide sequence encoding an adenoviral E1B protein, wherein the E1B protein comprises an E1B-55K protein but not an E1B-19K protein. In another preferred embodiment, the helper adenovirus nucleic acid sequences include: (i) a nucleic acid molecule comprising a nucleotide sequence encoding adenoviral E1A proteins deficient in binding to p300 protein family members and pRb protein family members; and (ii) a nucleic acid molecule comprising a nucleotide sequence encoding an adenoviral E2B polymerase; and (iii) a nucleic acid molecule comprising a nucleotide sequence encoding adenoviral E1B-55K and E1B-19K proteins.

The nucleotide sequence(s) encoding the adenovirus mutant E1A proteins, which is utilized as a helper adenovirus nucleic acid sequence in accordance with the present invention, provides only the required functions for producing high levels of E1-deleted adenovirus vectors. More specifically, the nucleotide sequence(s) encodes E1A proteins that are defective for binding to the cellular proteins p300/CBP and pRb but still carry the wild-type CR3 domain which transactivates early viral promoters required for the initial phase of lytic growth. The use of such a nucleotide sequence overcomes the toxicity associated with wild-type adenoviral E1A proteins in tumor cells.

The rationale for using nucleotide sequences encoding E1A proteins defective in p300 and pRb binding is based, in part, on mapping studies that have separated the E1A functions required for induction of cellular DNA synthesis and activation of the early adenovirus transcription units. The ability of the E1A adenoviral proteins to activate the early transcription units is required in all production cell lines for successful productive infection, but the ability of the E1A to induce the cell cycle may not be required in established cell lines that divide continuously. The nucleotide sequences encoding the mutated adenovirus E1A proteins described herein retain the ability to activate transcription, but are defective for induction of cellular DNA synthesis. The adenoviral E1A regions required for stimulation of cellular DNA synthesis may also be responsible for induction of apoptosis and this may hinder successful establishment of E1-complementing cell lines.

To produce E1A proteins that are defective for binding to the cellular proteins p300/CBP and pRb, mutations in the E1A 289R and E1A 243R coding regions can be introduced. In a specific embodiment, deletions in the E1A 289R and E1A 243 coding regions are introduced to achieve a reduction in the binding of p300 and pRb family members to E1A proteins. Preferably, the deletions in the E1A 289R and the E1A 243R coding sequences necessary to achieve reduction of p300 and pRb binding are as minimal as possible to prevent major disruption of the secondary and tertiary structure of the E1A 289R and the E1A 243R proteins.

In order to eliminate p300 binding it is preferred that a mutation be introduced in the nucleotide sequence encoding the p300 binding domains of E1A 289R and E1A 243R. The p300 binding domain of the E1A-12S and 13S proteins has been narrowed to the first 69 amino acids (Egan, et al. (1988) Mol. Cell Biol. 8:3955-3959). However, it has been shown that amino acids 26 to 35 are not necessary for p300 binding. There are two regions of p300 binding in the 12S and 13S molecules from approximately amino acid residues 4-25 and amino acid residues 36-49. Elimination of one or both is sufficient to disrupt p300 binding. Preferably, the elimination of amino acid residues 4-25 is employed to eliminate the p300 binding function. Deletions of less than about 30 amino acids in the C-terminal region to eliminate p300 binding are preferred, although smaller modifications are more preferred. In a specific embodiment, deletions in the C-terminal region to eliminate p300 binding are 25 amino acids or less, 20 amino acids or less, 15 amino acids or less, or 10 amino acids or less. The deletion of amino acid residues 4-25 of the 289R and the 243R proteins are sufficient to disrupt p300 binding without affecting transactivational functions of CR3. The "transactivating function of the CR3 domain" refers to the ability of the products of the E1A gene to activate transcription of promoters later in the viral cycle such as E1B and E3. The CR3 region is functionally present only in the 13S protein and represents amino acids 140 to 188. The transactivating function of the E1A gene product is contained in the CR3 region. Alternatively preferred are a deletion of amino acids from amino acid residue 30 to amino acid residue 49 (dl1103) and more particularly amino acid residue 36 to amino acid residue 49 to eliminate p300 binding.

Point mutations sufficient to disrupt binding p300 are particularly preferred. For example, a point mutation of the second amino acid from arginine to glycine (Arg2 to Gly2) in the 289R protein has been demonstrated to disrupt p300 binding (See e.g., pm563, Whyte, et al., (1989) Cell 56:67-75).

The Rb-105 binding domain of the E1A-12S and 13S proteins has been characterized as located within amino acids 111-127. Similarly, in regard to eliminating pRb105 binding, minimal modifications are preferred. In a specific embodiment, deletions in the pRb binding domain of less than 20 amino acids, 15 amino acids or less, 10 amino acids or less are introduced. Elimination of selective amino acids in the pRb105 binding domain such as amino acid 111-123 (dl1107) and amino acids 124-127 (dl1108) are preferred. In an embodiment, the mutation set forth by Moran et al. (pm928 (C124G)) is used to disrupt pRb105 binding ((1986) Mol Cell Biol. 6(10):3470-3480).

In a specific embodiment, a nucleic acid molecule comprising a nucleotide sequence encoding the adenoviral E1A mutant E1Adl01/07 protein is utilized as a helper adenovirus nucleic acid sequence. The E1Adl01/07 protein is defective for binding to the cellular proteins p300/CBP and pRb but still carries the wild-type CR3 domain which transactivates early viral promoters required for the initial phase of lytic growth. It has mutations affecting the ability of the adenoviral E1A protein to induce cellular DNA synthesis and apoptosis but still carries the wild-type CR3 domain which transactivates early viral promoters required for the initial phase of lytic growth (Winberg and Shenk, (1984) EMBO J. 3:1907-1912).

Helper adenovirus nucleic acid sequences may be propagated in microorganisms, for example, as part of a bacterial plasmid or bacteriophage. A nucleotide sequence encoding an adenoviral protein may be incorporated into a recombinant plasmid, bacteriophage, etc. by methods well known in the art.

In a specific embodiment, a nucleic acid molecule comprising a nucleotide sequence encoding an adenoviral protein is operably linked to a regulatory element. In a particular embodiment, the nucleotide sequence encoding an adenoviral protein is inserted into an appropriate expression vector, i.e., a vector that contains the necessary elements for the transcription and translation of the inserted protein coding sequence. The necessary transcriptional and translational signals can be supplied by the native promoter of the adenoviral protein and/or a heterologous promoter. Any method available in the art can be used for the insertion of a nucleotide sequence into a vector to construct expression vectors containing appropriate transcriptional/translational control signals and protein coding sequences.

In one embodiment, each nucleotide sequence encoding an adenoviral protein is inserted into an expression vector. In alternative embodiment, two or more nucleotide sequences encoding adenoviral proteins are inserted into one expression vector.

In a specific embodiment, a vector is used that comprises a promoter operably linked to a nucleotide sequence encoding an adenoviral protein, one or more origins of replication, and optionally, one or more selectable markers (e.g., an antibiotic resistance gene). In accordance with this embodiment, a promoter can be any promoter known to the skilled artisan. For example, the promoter can be a constitutive promoter, a tissue-specific promoter or an inducible promoter. Examples of promoters that may be used in accordance with the invention include: the SV40 early promoter (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42), the beta-actin promoter, the CMV promoter, the SR-alpha promoter, the hFer/SV40 promoter, the RSV promoter, the Elf-1 promoter, the Tet promoter, the Ecdyson promoter and a rapamycin promoter.

In a specific embodiment, a native promoter is utilized to regulate the expression of a nucleotide sequence encoding an adenoviral protein. In alternative embodiment, a promoter that is not native to the adenoviral gene encoding the protein being expressed (i.e., a heterologous promoter) is utilized to regulate the expression of the protein. In certain embodiments, the promoter is a constitutive promoter (e.g., a viral, cellular or hybrid constitutive promoter). In other embodiments, the promoter is an inducible promoter. In yet other embodiments, the promoter is a tissue-specific promoter.

In certain embodiments, it is desirable to use a constitutive promoter, such as a CMV promoter, beta-actin promoter, SR-alpha promoter or hFer/SV40 promoter, to regulate the expression of a nucleotide sequence encoding one or more of the following proteins: E1B proteins, E2A proteins and/or E2B proteins. In certain other embodiments, it is desirable to use a constitutive promoter, such as a RSV promoter, SV40 promoter or Elf-1 promoter, to regulate the expression of a nucleotide sequence encoding one or more of the following proteins: E1A proteins and/or E4 proteins. In yet other embodiments, it is desirable to use an inducible promoter, such as a Tet promoter or Ecdyson promoter, to regulate the expression of L4 100K.

Expression vectors containing the nucleotide sequences of interest can be identified by three general approaches: (1) nucleic acid hybridization, (2) presence or absence of "marker" gene function, and (3) expression of the inserted sequences. In the first approach, coding sequences can be detected by nucleic acid hybridization to probes comprising sequences homologous and complementary to the inserted sequences. In the second approach, the recombinant vector/host system can be identified and selected based upon the presence or absence of certain "marker" functions (e.g., resistance to antibiotics, occlusion body formation in baculovirus, etc.) caused by insertion of the sequences of interest in the vector. For example, if a nucleotide sequence encoding an adenoviral protein, or portion thereof, is inserted within the marker gene sequence of the vector, cells transfected with the encoded protein or portion will be identified by the absence of the marker gene function (e.g., loss of beta-galactosidase activity). In the third approach, expression vectors can be identified by assaying for the adenoviral protein expressed by the recombinant vector. Such assays can be based, for example, on the physical or functional properties of the interacting species in in vitro assay systems, e.g., binding to an antibody.

The helper adenovirus nucleic acids may be incorporated into a cell line, thus bypassing the need to cotransfect helper adenovirus nucleic acid sequences and recombinant adenovirus vector sequences. Instead, transfection of the helper adenovirus nucleic acid sequence-containing cell line with recombinant adenovirus vector would directly result in production of recombinant adenovirus. The present invention provides for such cell lines. See Section 5.3, infra.

5.2 Recombinant Adenovirus Constructs

The recombinant adenovirus vectors of the invention comprise adenoviral nucleotide sequences and optionally, one or more heterologous nucleotide sequences. In a preferred embodiment, the recombinant adenovirus vectors comprise adenoviral nucleotide sequences that lack of homology to the helper adenovirus nucleic acid sequences. The lack of homology between the adenoviral helper nucleic acid sequences and recombinant adenovirus vectors reduces the possibility of the viral genome recombining to produce replication competent adenovirus. In a preferred embodiment, the recombinant adenovirus vector encodes a replication-defective adenovirus. In accordance with this embodiment, the recombinant adenovirus vector may be engineered to comprise a mutated adenovirus genome by, e.g., introducing one or more mutations in an adenovirus genome (e.g., introducing deletions in one or more coding regions for adenoviral proteins). Preferably, the mutations in the adenovirus genome result in lower levels of expression of adenoviral proteins than wild-type adenovirus. The reduction in adenoviral protein expression reduces the immune response to the adenoviral proteins in a subject.

In a specific embodiment, the recombinant adenovirus vector encodes a replication-defective adenovirus and comprises a mutated genome with a partial or complete (preferably, a complete) deletion of the E1A coding region (e.g., SEQ ID NO: 17) and E1B coding region (e.g., SEQ ID NO: 18), and may include one or more heterologous nucleotide sequences. In another embodiment, the recombinant adenovirus vector encodes a replication-defective adenovirus and comprises a mutated genome with a partial or complete (preferably, a complete) deletion of the E1A coding region (e.g., SEQ ID NO: 17), E1B coding region (e.g., SEQ ID NO: 18), and E2B polymerase coding region (for example, SEQ ID NO: 23), and includes one or more heterologous nucleotide sequences. The heterologous nucleotide sequences can be introduced into any region of the genome (e.g., the amino or carboxy-termini). In a specific embodiment, a heterologous nucleotide sequence is introduced into one of the deleted adenoviral coding regions, such as the E1A or E2B coding region, of the mutated adenoviral genome. In a preferred embodiment, the recombinant adenovirus vector encodes a replication-defective adenovirus and comprises a mutated genome with a partial or complete (preferably, a complete) deletion of the E1A coding region (e.g., SEQ ID NO: 17), E1B coding region (e.g., SEQ ID NO: 18), E2B polymerase coding region (e.g., SEQ ID NO: 25), and E3 coding region, and includes a heterologous nucleotide sequence in the deleted E3 coding region.

In accordance with the invention, the recombinant adenovirus (rAd) vectors comprise an adenoviral genome or a portion thereof obtained and/or derived from any adenoviridae or a combination of adenoviridae. In a preferred embodiment, the recombinant adenovirus vectors comprise an adenoviral genome or portion thereof obtained and/or derived from a human adenoviridae. In another preferred embodiment, the recombinant adenovirus vectors comprise an adenoviral genome or portion thereof obtained and/or derived from the human adenovirus serotype 2 or 5.

The rAd vector of the present invention may incorporate any heterologous nucleotide sequence, including genes or portions of genes. It may be desirable to incorporate a gene with a readily detectable product (known in the art as a marker, recorder, or reporter gene) as part of the rAd vector although the invention is not limited to such constructs. Non-limiting examples of reporter genes include beta-galactosidase, neomycin phosphoro-transferase, chloramphenicol acetyltranferase, thymidine kinase, luciferase, beta-glucuronidase, and xanthine-guanine phosphoribosyl transferase, to name but a few.

In an embodiment of the invention, the heterologous nucleotide sequence is obtained and/or derived from a source other than the rAd vector. In certain embodiments, the heterologous nucleotide sequence encodes an antigenic protein, a polypeptide or peptide of a virus belonging to a different species, subgroup or variant of adenovirus other than the species, subgroup or variant from which the rAd vector is derived. In other embodiments, the heterologous nucleotide sequence is not viral in origin. In accordance with these embodiments, the heterologous nucleotide sequence may encode a moiety, peptide, polypeptide or protein possessing a desired biological property or activity. Such a heterologous nucleotide sequence may encode a tag or marker. Such a heterologous nucleotide sequence may encode a biological response modifier, examples of which include, interleukins, hormones and growth factors.

In certain embodiments, the heterologous nucleotide sequence encodes an antigenic protein, polypeptide or peptide obtained and/or derived from a virus other than an adenovirus. Non-limiting examples of such viruses from the following families: adenoviridae (e.g., arenavirus, lymphocytic choriomeningitis virus, Ippy virus, and lassa virus), arterivirus (e.g., equine arteritis virus), astroviridae (e.g., astrovirus), bunyaviridae (e.g., bunyavirus, bunyamwera virus, hantavirus, Crimean-congo hemorrhagic fever virus, phlebovirus, and Rift Valley fever complex), caliciviridae (e.g., calicivirus), Coronaviridae (e.g., coronavirus, torovirus and SARS), deltavirus, filoviridae (e.g., filovirus, Marburg virus and Ebola virus Zaire), flaviviridae (e.g., flavivirus, yellow fever virus, tick-borne encephalitis virus group, Japanese encephalitis Group, pestivirus and hepatitis C virus), hepadnaviridae (e.g., hepatitis B virus), herpesviridae (e.g., human herpesvirus 1, varicellovirus, human herpesvirus 3, cytomegalovirus, human herpesvirus 5, roseolovirus, human herpesvirus 6, and human herpesvirus 4), orthomyxoviridae (e.g., influenza virus A, B and C), papovaviridae (e.g., papillomavirus), paramyxoviridae (e.g., paramyxovirus, human parainfluenza virus 1, morbillivirus, measles virus, rubulavirus, mumps virus, pneumovirus and human respiratory syncytial virus), parvoviridae (e.g., parvovirus and adeno-associated virus (MV)), picornaviridae (e.g., enterovirus, human poliovirus 1, rhinovirus, hepatovirus, human hepatitis A virus, cardiovirus, encephalomyocarditis virus, aphthovirus and foot-and-mouth disease virus O), poxyiridae (e.g., vaccinia virus, fowipox virus and myxoma virus), reoviridae (e.g., reovirus, rotavirus, coltivirus, cypovirus, and fijivirus), retroviridae (e.g., murine leukemia virus, human T lymphocyte leukemia (HTLV)-1 and 2, and lentivirus such as human immunodeficiency virus 1, human immunodeficiency virus 2, and simian immunodeficiency virus), rhabdoviridae (e.g., vesiculovirus, lyssavirus and rabies virus), and togaviridae (e.g., Sindbis virus, Rubivirus and Rubella virus). See, e.g., Fields et al., (ed.), 1991, Fundamental Virology, Second Edition, Raven Press, New York, incorporated by reference herein in its entirety, for a description of viruses and viral antigens.

In certain embodiments, the heterologous nucleotide sequence encodes an antigenic protein, polypeptide or peptide of obtained and/or derived from a bacteria, fungi, and/or other pathogen or parasite. Examples of heterologous nucleotide sequences obtained and/or derived from bacteria include, but are not limited to, nucleotide sequences encoding antigens derived from species of the following genera: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae*, as well as bacterial species such as: *P. aeruginosa, E. coli, P. cepacia, S. epidermis, E. faecalis, S. pneumonias, S. aureus, N. meningitidis, S. pyogenes, Pasteurella multocida, Treponema pallidum*, and *P. mirabilis*.

Examples of heterologous nucleotide sequences derived from fungi, include, but are not limited to, nucleotide sequences encoding antigens obtained and/or derived from fungi such as *Cryptococcus neoformans, Blastomyces dermatitidis, Aiellomyces dermatitidis, Histoplasma capsulatum; Coccidioides immitis, Candida* species, including *C. albicans, C. tropicalis, C. parapsilosis, C. guilliermondii* and *C. krusei, Aspergillus* species, including *A. fumigatus, A. flavus* and *A. niger, Rhizopus* species, *Rhizomucor* species, *Cunninghammella* species, *Apophysomyces* species, including *A. saksenaea, A. mucorand A. absidia, Sporothrix schenckii, Paracoccidioides brasiliensis, Pseudallescheria boydii, Torulopsis glabrata; Trichophyton* species, *Microsporum* species and *Dermatophyres* species, as well as any other yeast or fungus now known or later identified to be pathogenic.

Finally, examples of heterologous nucleotide gene sequences obtained and/or derived from parasites include, but are not limited to, nucleotide sequences encoding antigens derived from members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkella, Haemoproteus, Leucocytozoon, Theileria, Perkinsus* and *Gregarina* spp.; *Pneumocystis carinii*, members of the *Microspora phylum* such as, for example, *Nosema, Enterocytozoon, Encephalitozoon, Septata, Mrazekia, Amblyospora, Ameson, Glugea, Pleistophora* and *Microsporidium* spp.; and members of the *Ascetospora phylum* such as, for example, *Haplosporidium* spp., as well as species including *Plasmodium falciparum, P. vivax, P. ovale, P. malaria; Toxoplasma gondi, Leishmania mexicana, L. tropica, L. major, L. aethiopica, L. donovani, Trypanosoma cruzi, Tbrucei, Schistosoma mansoni, S. haematobium, S. japonium, Trichinella spiralis, Wuchereria bancrofti, Brugia malayli, Entamoeba histolytica; Enterobius vermiculoarus, Taenia sollum, T. saginata, Trichomonas vaginatis, T. hominis, T. tenax, Giardia lamblia, Cryptosporidium parvum; Pneumocytis carini, Babesia bovis, B. divergens, B. microti, Isospora belli, L. hominis, Dientamoeba fragilis, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latumr, Echinococcus granulosus, E. multilocularis, Paragonimus westermani, P. caliensis, Chlonorchis sinensis, Opisthorchis felineas, G. Viverini, Fasciola hepatica, Sarcoptes scabiei, Pediculus humanus, Phthirlus pubis*, and *Dermatobia hominis*, as well as any other parasite now known or later identified to be pathogenic.

Other heterologous nucleotide sequences of the present invention include nucleotide sequences encoding antigens that are characteristic of an autoimmune disease. These antigens will typically be derived from the cell surface, cytoplasm, nucleus, mitochondria and the like of mammalian tissues. Examples of such antigens include, but are not limited to, anitgens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythromatosus.

In certain embodiments, the heterlogous nucleotide sequences of the present invention include antigens that are allergens. Antigens that are allergens generally include proteins or glycoproteins, including antigens derived from pollens, dust, molds, spores, dander, insects and foods. In other embodiments, the heterologous nucleotide sequences of the present invention include tumor antigens. Tumor antigens typically will be derived from the cell surface, cytoplasm, nucleus, organelles and the like of cells of tumor tissue. Non-limiting examples of tumor antigens include proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In certain embodiments, the heterologous nucleotide sequence encodes a biological response modifier such as a cytokine, cytokine receptor, hormone, growth factor or growth factor receptor. Non-limiting examples of such biological response modifiers include interferon (IFN)-alpha, IFN-beta, IFN gamma, interleukin (IL-1), IL-2, IL-3, IL-4, IL-5, IL-6, IL-7, IL-9, IL-10, IL-12, IL-15, IL-18, IL-23, erythropoietin (EPO), basic fibroblast growth factor (bFGF), acidic fibroblast growth factor (aFGF), vascular endothelial growth factor (VEGF), platelet derived growth factor (PDGF), epidermal growth factor (EGF), thymic stromal lymphopoietin (TSLP), TNFR and TNFR ligand superfamily members including TNFRSF 18 and TNFSF18. In other embodiments, the heterologous nucleotide sequence encodes an antibody. In yet other embodiments, the heterologous nucleotide sequence encodes a chimeric or fusion protein.

According to the invention, if the heterologous nucleotide sequence of the rAd vector is to be expressed in host cells, a transcriptional control element, also called a promoter/enhancer sequence, should be provided. The promoter/enhancer sequence may be widely active or may, alternatively, be tissue specific. The promoter/enhancer sequence may be derived from a non-adenovirus source or may be an adenovirus promoter. In a preferred embodiment, the promoter/enhancer sequences used to regulate the expression of the heterologous nucleotide sequence are not shared with those promoter/enhancer sequences that regulate the expression of the helper adenovirus nucleic acid sequences. In certain embodiments, the promoter is a constitutive promoter. In other embodiments, the promoter is an inducible promoter. In yet other embodiments, the promoter is a tissue-specific promoter. See Section 5.1, supra, for examples of promoters.

The desirable size of inserted non-adenovirus or heterologous nucleotide sequence is limited to that which permits packaging of the rAd vector into virions, and depends on the size of retained adenovirus sequences. The genome of a human adenovirus is approximately 36 kilobase pairs in length (measured to be 35938 nucleotides in length by Davison et al. (2003) J. Gen. Virology 84 (Pt 11), 2895-2908). The total size of the rAd to be packaged into virions should be about 37735 nucleotides in length (about 105% of the normal genome length). Therefore, it may be desirable to exclude portions of the adenovirus genome in the rAd vector in order to maximize expression of the inserted heterologous nucleotide sequence.

Insertion of a foreign gene sequence into a rAd vector of the invention can be accomplished by either a complete replacement of a viral coding region with a heterologous nucleotide sequence or by a partial replacement or by adding the heterologous nucleotide sequence to the viral genome. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the gene that is to be replaced; and a stretch of nucleotides complementary to the carboxy-terminus coding portion of the heterologous nucleotide sequence. PCR-primer B would contain from the 5' to 3' end: a unique restriction enzyme site; a stretch of nucleotides complementary to the gene that is to be replaced; and a stretch of nucleotides corresponding to the 5' coding portion of the heterologous or non-native gene. After a PCR reaction using these primers with a cloned copy of the heterologous or non-native gene, the product may be excised and cloned using the unique restriction sites. Digestion with the class IIS enzyme and transcription with the purified phage polymerase would generate a RNA molecule containing the exact untranslated ends of the viral gene that carries now a heterologous or non-native gene insertion. In an alternate embodiment, PCR-primed reactions could be used to prepare double-stranded DNA containing the bacteriophage promoter sequence, and the hybrid gene sequence so that RNA templates can be transcribed directly without cloning.

When inserting a heterologous nucleotide sequence into the rAd vector of the invention, the intergenic region between the end of the coding sequence of the heterologous nucleotide sequence and the start of the coding sequence of the downstream gene can be altered to achieve a desired effect. As used herein, the term "intergenic region" refers to nucleotide sequence between the stop signal of one gene and the start codon (e.g., AUG) of the coding sequence of the next downstream open reading frame. An intergenic region may comprise a non-coding region of a gene, i.e., between the transcription start site and the start of the coding sequence (AUG) of the gene. This non-coding region occurs naturally in some viral genes.

The expression of the inserted heterologous nucleotide sequence can be determined by various indexes including, but not limited to, protein or mRNA expression levels, measured by following non-limiting examples of assays: immunostaining, immunoprecipitation and immunoblotting, enzyme-linked immunosorbent assay, nucleic acid detection (e.g., Southern blot analysis, Northern blot analysis, Western blot analysis), employment of a reporter gene (e.g., using a reporter gene, such as Green Fluorescence Protein (GFP) or enhanced Green Fluorescence Protein (eGFP), integrated to the viral genome the same fashion as the interested heterologous gene to observe the protein expression), or a combination thereof. Procedures of performing these assays are well known in the art (see, e.g., Flint et al., PRINCIPLES OF VIROLOGY, MOLECULAR BIOLOGY, PATHOGENESIS, AND CONTROL, 2000, ASM Press pp 25-56, the entire text is incorporated herein by reference).

For example, expression levels can be determined by infecting cells in culture with a recombinant adenovirus of the invention and subsequently measuring the level of protein expression by, e.g., Western blot analysis or ELISA using antibodies specific to the gene product of the heterologous nucleotide sequence, or measuring the level of RNA expression by, e.g., Northern blot analysis using probes specific to the heterologous sequence. Similarly, expression levels of the heterologous sequence can be determined by infecting an animal model and measuring the level of protein expressed from the heterologous nucleotide sequence of the recombinant virus of the invention in the animal model. The protein level can be measured by obtaining a tissue sample from the infected animal and then subjecting the tissue sample to Western blot analysis or ELISA, using antibodies specific to the gene product of the heterologous sequence. Further, if an animal model is used, the titer of antibodies produced by the animal against the gene product of the heterologous sequence can be determined by any technique known to the skilled artisan, including but not limited to, ELISA.

According to the invention, a rAd vector may be propagated in microorganisms, for example, as part of a bacterial plasmid or bacteriophage, in order to obtain large quantities of rAd vector.

5.3 Generation of Cell Lines for Production of Recombinant Adenovirus

The present invention provides host cells comprising the helper adenovirus nucleic acid sequences described herein and methods for producing such cells. The host cells transfected or transformed with the helper adenovirus nucleic acid sequences are useful in the production of recombinant adenovirus, in particular replication-defective recombinant adenovirus. Specifically, the host cells of the present invention complement functions missing from the recombinant adenovirus vector and/or recombinant adenovirus of interest (i.e., the adenoviral E1A, for example, SEQ ID NO: 17, and E1B, for example, SEQ ID NO: 18, coding regions). More specifically, host cells transfected or transformed with the helper adenovirus nucleic acid sequences described herein express adenoviral proteins that complement the recombinant adenovirus vectors described herein. Preferably, the host cells contain complementing adenoviral genes that lack any homology to those in the recombinant adenoviral vector of interest, which reduces the possibility of the viral genome recombining with the cellular DNA to produce replication competent adenovirus. Host cells that complement the recombinant adenovirus vectors described herein are sometimes referred to herein as "complementing cell lines", "rAd production cell lines", "rAd complementation cells" and "rAd complementation cell lines".

In a specific embodiment, the present invention provides an isolated host cell comprising: (a) first nucleic acid molecule comprising a nucleotide sequence encoding adenoviral E1A proteins deficient in binding to p300 protein family members and pRb protein family members; and (b) a second nucleic acid molecule comprising a nucleotide sequence encoding an adenoviral E1B-55K protein. In accordance with this embodiment, the second nucleic acid molecule, in certain embodiments, does not comprise a nucleotide sequence encoding an adenoviral E1B-19K protein. In a preferred embodiment, the present invention provides an isolated host cell comprising: (a) a first nucleic acid molecule comprising a nucleotide sequence encoding adenoviral E1A proteins deficient in binding to p300 protein family members and pRb protein family members; (b) a second nucleic acid molecule comprising a nucleotide sequence encoding an adenoviral E2B polymerase; and (c) a third nucleic acid molecule comprising a nucleotide sequence encoding adenoviral E1B-55K and E1B-19K proteins. In accordance with these embodiments, the host cell may further comprise additional nucleic acid molecules comprising nucleotide sequences encoding an adenoviral E2a DNA binding protein, an adenoviral E2b pre-terminal protein, an adenoviral E2b IVa2 protein, adenoviral E4 proteins (e.g., ORF 6, ORF 3 and ORF 6/7 of an adenoviral E4 gene), and/or an adenoviral protein encoded by L4 100K.

In certain embodiments, the present invention provides an isolated host cell comprising a nucleic acid molecule comprising: (i) a nucleotide sequence encoding adenoviral E1A proteins deficient in binding to p300 protein family members and pRb protein family members; and (ii) a nucleotide sequence encoding an adenoviral E1B-55K protein. In certain other embodiments, the present invention provides an isolated host cell comprising a nucleic acid molecule comprising: (i) a nucleotide sequence encoding adenoviral E1A proteins deficient in binding to p300 protein family members and pRb protein family members; (ii) a nucleotide sequence encoding an adenoviral E2B polymerase; and (iii) a nucleotide sequence encoding adenoviral E1B-55K and E1B-19K proteins.

In a specific embodiment, the E1A proteins expressed by the host cells comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein. In a preferred embodiment, the E1A proteins expressed by the host cells comprise: (a) a first deletion corresponding to amino acid residues 4-25 of an E1A 289R protein (dl1101) and amino acid residues 4-25 of an E1A 243R protein (dl1101); and (b) a second deletion corresponding to amino acid residues 111-123 (dl1107) of an E1A 289R protein and amino acid residues 111-123 (dl1107) of an E1A 243R protein.

The ability of the E1A adenoviral proteins to activate the early transcription units is required in all production cell lines for successful productive infection, but the ability of the E1A to induce the cell cycle may not be required in established cell lines that divide continuously. The mutated E1A adenovirus genes expressed in the rAd complementing cell lines of the present invention retain the ability to activate transcription, but are defective for induction of cellular DNA synthesis. The adenoviral E1A regions required for stimulation of cellular DNA synthesis, which are not expressed in the rAd complementing cell lines of the invention, may also be responsible for induction of apoptosis which may hinder successful establishment of rAd complementing cell lines.

Any type of cell may be used as a host cell. In a preferred embodiment, a cell that is permissible to adenovirus, preferably human adenovirus, infection is used. A host cell strain may be chosen which modulates, or modifies and processes the expression of a gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines can be chosen to ensure the correct modification and processing of the foreign protein expressed. To this end, eukaryotic host cells (e.g., mammalian host cells) which possess the cellular machinery for proper processing of the primary transcript, glycosylation, and phosphorylation of a gene product may be used. Examples of such mammalian host cells include, but are not limited to, CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells. In a specific embodiment, the host cell is a A549, HCT-15, IGROV-1, HeLa, U87, W162 or 293-D22 cell. In a preferred embodiment, the host cell is a A549 cell. In certain embodiments, the host cells can be cultured and propagated in suspension.

In a preferred embodiment, human cells are used as host cells. Human established cell lines such as those from human tumor cells or human tumor cell lines have the ability to replicate indefinitely in culture. Human tumor cells, cells from human established cell lines or cells from human tumor cell lines are preferred over human primary cells for generating complementing cell lines of the present invention because the mutated E1A adenovirus genes expressed in the E1-complementing cell lines of the present invention retain the ability to activate transcription, but are defective for induction of cellular DNA synthesis and for transformation of a primary cell line to a continuously replicating cell line or an established cell line. Such cell lines can be generated in accordance with standard molecular biological techniques.

Host cells may be transiently or stably transfected with helper adenovirus nucleic acid sequences. Non-limiting methods for transfecting a host cell include the DEAE dextran method (McCutchen and Pagano, 1968, J. Natl. Cancer Inst. 41:351-357), the calcium phosphate procedure (Graham et al., 1973, J. Virol. 33:739-748), microinjection, lipofection, electroporation, and any other method known in the art. Preferably, the helper adenovirus nucleic acid sequences are stably integrated into the nuclear genome of the host cells. It is believed that genomic integration of the heterologous nucleic acid sequences encoding the complementary factors is required to generate stable recombinant cell lines for adenoviral vector production. Additionally, complementation by transient transfection is labor-intensive, difficult to scale-up and may provide low adenovirus yields. The introduction and stable integration of the heterologous nucleic acid sequences into the genome of the cell requires standard molecular biological techniques that are within the skill of the art, (see. e.g., Sambrook, Fritsch & Maniatis, *Molecular Cloning: A Laboratory Manual*, Second Edition (1989) Cold Spring Harbor Laboratory Press, Cold Spring Harbor, N.Y.).

For long-term, high-yield production of recombinant adenoviral proteins, stable expression is preferred. For example, cell lines which stably express the adenoviral proteins encoded by the helper adenovirus nucleic acid sequences may be engineered. Host cells can be transformed with nucleotide sequences controlled by appropriate expression control elements (e.g., promoter, enhancer, sequences, transcription terminators, polyadenylation sites, etc.), and a selectable marker. Following the introduction of the foreign nucleotide sequences, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the adenoviral proteins encoded by the helper adenovirus nucleic acid sequences.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1, which are incorporated by reference herein in their entireties.

The expression levels of adenoviral proteins encoded by helper adenovirus nucleic acid sequences can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an adenoviral protein(s) is amplifiable, increase in the level of inhibitor present in culture of host cell will increase the number of copies of the marker gene. Since the amplified region is associated with the adenoviral protein(s), production of the adenoviral protein(s) will also increase (Crouse et al., 1983, Mol. Cell. Biol. 3:257).

The present invention provides methods for producing a host cell for the production of replication-defective adenovirus comprising transforming or transfecting a cell (preferably, a human cell) with a first nucleic acid molecule and a second nucleic acid molecule, wherein the first nucleic acid molecule comprising a nucleotide sequence encoding adenoviral E1A proteins deficient in binding to p300 protein family members and pRb protein family members (see above for examples of such adenoviral proteins), and the second nucleic acid molecule comprises a nucleotide sequence encoding an adenoviral E1B-55K protein (and preferably, does not comprise a nucleotide sequence encoding an adenoviral E1B-19K protein). The cell may be transformed or transfected with the first and second nucleic acid molecules simultaneously or sequentially in any order. In a specific embodiment, the cell is transformed or transfected with the first nucleic acid molecule and then the second nucleic acid molecule.

The present invention provides methods for producing a cell for the production of replication-defective adenovirus comprising transforming or transfecting a cell (preferably, a human cell) with a first nucleic acid molecule, a second nucleic acid molecule and a third nucleic acid molecule, wherein the first nucleic acid molecule comprises a nucleotide sequence encoding adenoviral E1A proteins deficient in binding to p300 protein family members and pRb protein family members (see above for examples of such adenoviral proteins), the second nucleic acid molecule comprises a nucleotide sequence encoding an adenoviral E2b polymerase, and the third nucleic acid molecule comprises a nucleotide sequence encoding an adenoviral E1B-55K protein and preferably, a nucleotide sequence encoding an adenoviral E1B-55K protein and E1B-19K protein. The cell may be transformed or transfected with the first, second and third nucleic acid molecules simultaneously or sequentially in any order. In a specific embodiment, the cell is transformed or transfected with the first nucleic acid molecule, the second nucleic acid molecule, and then the third nucleic acid molecule.

The rAd production cell lines of the invention may be propagated using standard cell culture techniques (see e.g., R. I. Freshney, Culture of Animal Cells-A Manual of Basic Techniques, Second Edition, Wiley-Liss, Inc. New York, N.Y., 1987). The rAd production cell lines are propagated by culturing the cells in an appropriate cell culture medium, such as Dulbecco's Modified Eagle's medium supplemented with 1-10% fetal bovine serum (in certain embodiments, it is 1% fetal bovine serum and other embodiments, it is 10% fetal bovine serum), antibiotics (e.g., 200 µg/ml hygromycin B and 200 µg/ml G418 for SL0003, and 150 µg/ml hyromycin B, 350 µg/ml G418, and 0.2 µg/ml puromycin for SL0006). For suspension culture of the rAd production cell lines, the rAd production cell lines are propagated by culturing the cells in, e.g., OptiPro media supplemented with 0.1% pluronic F-68, 1% chemically purified lipids, 4 mM glutamax, and antibiotics (e.g., 15 µg/ml hyromycin B, 35 µg/ml G418, and 0.02 µg/ml puromycin for SL0006). The antibiotics such as, e.g., hygromycin B, G418 and puromycin are included in the cell culture medium to maintain the selection pressure on the cell line. In certain embodiments, the rAd production cell lines of the invention are propagated in suspension culture.

The cells may be cryopreserved and stored for future use. Preferably, the cells are cryopreserved by propagating the cells to late exponential phase of growth; concentrating the cells; exchanging the growth medium to a medium supplemented with a cryoprotectant and a stabilizer; freezing the cells; and storing the cells at a temperature of 0° C. or less. Preferably, the cells are stored at −70° C. or less (e.g., −80° C.) or in liquid nitrogen or in the vapor phase of liquid nitrogen. The cells may be concentrated by any method known in the art. For example, the cells may be concentrated by centrifugation, sedimentation, concentration with a perfusion device (e.g., a sieve) or by filtration. Preferably, the cells are concentrated to at least about $1\times10^7$ cells/ml. The cells may be stored in any cryoprotectant known in the art. For example, the cryoprotectant may be dimethyl sulfoxide (DMSO) or glycerol. The cells may be stored in any stabilizer known in the art. For example, the stabilizer may be methyl cellulose or serum.

Prior to freezing down, the concentrated cells may be portioned into several separate containers to create a cell bank. The cells may be stored, for example, in a glass or plastic vial or tube or in a cell culture bag. When the cells are needed for future use, a portion of the cryopreserved cells (from one container) may be selected from the cell bank, thawed and propagated.

The rAd production cell line may be propagated or grown by any method known in the art for mammalian cell culture. Propagation may be done by a single step or a multiple step procedure. In a single step propagation procedure, the production cells are removed from storage and inoculated directly to a culture vessel where production of virus is going to take place. In a multiple step propagation procedure, the production cells are removed from storage and propagated through a number of culture vessels of gradually increasing size until reaching the final culture vessel where the production of recombinant adenovirus is going to take place. During the propagation steps, the cells are grown under conditions that are optimized for growth. Culture conditions, such as temperature, pH, dissolved oxygen level and the like are those known to be optimal for the particular cell line and will be apparent to the skilled person or artisan within this field (see e.g., *Animal Cell culture: A Practical Approach* $2^{nd}$ edition, Rickwood, D. and Hames, B. D. eds., Oxford University Press, New York (1992)).

The rAd production cells or rAd production cell lines may be grown in any suitable vessel which is known in the art. For example, cells may be grown and the infected cells may be cultured in a biogenerator or a bioreactor. Generally, "biogenerator" or "bioreactor" means a culture tank, generally made of stainless steel or glass, with a volume of 0.5 liter or greater, comprising an agitation system, a device for injecting a stream of $CO_2$ gas and an oxygenation device. Typically, it is equipped with probes measuring the internal parameters of the biogenerator, such as the pH, the dissolved oxygen, the temperature, the tank pressure or certain physicochemical parameters of the culture (for instance the consumption of glucose or of glutamine or the production of lactate and ammonium ions). The pH, oxygen, and temperature probes are connected to a bioprocessor which permanently regulates these parameters. In other embodiments, the vessel is a spinner flask, a roller bottle, a shaker flask or in a flask with a stir bar providing mechanical agitation. In another embodiment, a the vessel is a WAVE Bioreactor (WAVE Biotech, Bridgewater, N.J., U.S.A.).

Cell density in the culture may be determined by any method known in the art. For example, cell density may be determined microscopically (e.g., hemacytometer) or by an electronic cell counting device (e.g., COULTER COUNTER; AccuSizer 780/SPOS Single Particle Optical Sizer).

5.3.1 SL0003 Cell Line

As described in Example 1, the transformed cell line A549E1Adl01/07, that constitutively expressed the E1A mutated E1Adl01/07 gene, was selected for further development because it supported replication of E1-deleted rAd vectors at levels higher than A549 cell clones expressing either wild-type E1A or the single mutations E1Adl1101 or E1Adl1107. As shown in Example 1, infra, A549 cell clones, A549E1Adl01/07-1 to A549E1Adl01/07-5, supported replication of E1-deleted rAd vectors at levels higher than A549 cell clones A549E1Awt-1 to A549E1Awt-5, or A549 cell clones A549E1Adl01-1 to A549E1Adl1101-5, or A549 cell clones A549E1Adl1107-1 to A549E1Adl1107-5.

The transformed cell line, A549E1Adl01/07, was also selected for further development because of its reduced sensitivity to apoptosis during adenovirus vector production. A549 clones expressing wild-type E1A, i.e., A549E1Awt, were especially sensitive to apoptosis following infection with E1-deleted rAd vectors and viral yields were extremely low. The rapid induction of apoptosis in clone A549E1Awt-2 suggested that early events in viral infection may supply death signals that may be recognized by A549 cells expressing wild-type E1A but not E1Adl01/07.

Apoptosis in adenovirus-infected cells has been reported to be stimulated though p53-dependent and p53-independent pathways (Teodoro et al., (1995) Oncogene 11:467-474). It was found that both E2F and p53 pathways were stimulated in the A549 wt-2 clone as compared to the A549E1Adl01/07 clones in which E2F and p53 transcriptional activity was similar to the parental A549 cells. It was found that A549E1Awt-2 cells were driven into apoptosis by low levels of cycloheximide, but that A549E1Adl01/07 clones were unaffected by this treatment. The stimulation of the E2F and p53 pathways by wild-type E1A was not sufficient to induce apoptosis in the A549 wt-2 clone, but may have contributed to the increased sensitivity of these cells to death stimuli.

Although the transformed cell line, A549E1Adl01/07, was capable of producing replication defective adenovirus, it was reasoned that the viral yield may be further improved by complementation using E1B. It was unknown whether both E1B genes were needed for rAd vector complementation in the E1Adl01/07-expressing A549 cell line. Analysis of virus yield using a series of E1B-mutant viruses showed that in A549E1Adl01/07-4 cells, expression of E1B-55K alone was sufficient for production of the mutant viruses at wild-type levels. These results suggested that efficient complementation may be achieved in A549 cells by E1Adl01/07 plus E1B55K, which was subsequently achieved in the SL0003 cell line. The yield of rAd vectors from the SL0003 cell line was similar to that obtained from 293 cells, without generation of detectable replication competent adenovirus (RCA).

The SL0003 cell line was deposited under the Budapest Treaty, on Sep. 22, 2004 with the American Type Culture Collection (ATCC), 10801 University Blvd., Manassas, Va., 20110-2209, USA, under the indicated name and accession number as follows; Deposit name: "SL0003"; ATCC Accession Number: PTA-6231. All restrictions on access to the cell line deposited with the ATCC will be removed upon grant of a patent.

5.3.2 SL0006 Cell Line

As described in Example 2, to improve viral yield, the transformed cell line, A549E1Adl01/07, was transformed with a nucleic acid molecule comprising a nucleotide sequence encoding adenoviral E2b polymerase and a nucleic acid molecule comprising a nucleotide sequence encoding adenoviral E1B-55K and E1B-19K proteins. The results presented in Example 2 demonstrate that efficient complementation may be achieved in A549 cells by E1Adl01/07 plus E2b polymerase, E1B-55K and E1B-19K. The yield of rAd vectors from the SL0006 cell line was similar to that obtained from 293 cells, without generation of detectable replication competent adenovirus (RCA).

The SL0006 cell line was deposited under the Budapest Treaty, on Apr. 7, 2005 with the American Type Culture Collection (ATCC), 10801 University Blvd., Manassas, Va., 20110-2209, USA, under the indicated name and accession number as follows; Deposit name: "SL0006"; ATCC Accession Number: PTA-6663. All restrictions on access to the cell line deposited with the ATCC will be removed upon grant of a patent.

5.4 Production of Recombinant Adenovirus

In accordance with the invention, recombinant adenovirus (preferably, recombinant replication-defective adenovirus) may be produced by co-transfecting an appropriate cell type with rAd vector and helper adenovirus nucleic acid sequences. Co-transfection may be performed by the DEAE dextran method (McCutchen and Pagano, 1968, J. Natl. Cancer Inst. 41:351-357), the calcium phosphate procedure (Graham et al., 1973, J. Virol. 33:739-748) or by any other method known in the art, including but not limited to microinjection, lipofection, and electroporation. Amounts of rAd vector and helper adenovirus nucleic acid sequences used in transfection are approximately 0.2 to 10 µg of DNA per $10^6$ cells, but may vary among different DNA constructs and cell types. Cells suitable for transfection include any cell line permissive for adenvirus infection, including, but not limited to HeLa cells, 293-D22 cells, A549 cells, HCT-15 cells, IGROV-1 cells, U87 cells and W162 cells.

Alternatively, a rAd complementing cell line may be transfected with rAd vector to produce of recombinant adenovirus (preferably, recombinant replication-defective adenovirus). In a specific embodiment, the present invention provides a method for producing recombinant adenovirus comprising culturing a rAd complementing cell line transfected with recombinant adenovirus vector under conditions so as to permit replication of the viral genome in the cell line, wherein the cell line comprises: (a) a first nucleic acid molecule comprising a nucleotide sequence encoding adenoviral E1A proteins deficient in binding to p300 protein family members and pRb protein family members (see the description above regarding such E1A proteins); and (b) a second nucleic acid molecule comprising a nucleotide sequence encoding an adenoviral E1B-55K protein (and preferably, does not comprise a nucleotide sequence encoding an adenoviral E1B-19K protein). In a preferred embodiment, the present invention provides a method for producing recombinant adenovirus comprising culturing a rAd complementing cell line transfected with recombinant adenovirus vector under conditions so as to permit replication of the viral genome in the cell line, wherein the cell line comprises: (a) a first nucleic acid molecule comprising a nucleotide sequence encoding adenoviral E1A proteins deficient in binding to p300 protein family members and pRb protein family members (see the description above regarding such E1A proteins); (b) a second nucleic acid molecule comprising a nucleotide sequence encoding an adenoviral E2B polymerase; and (c) a third nucleic acid molecule comprising a nucleotide sequence encoding an adenoviral E1B-55K protein, and preferably, an adenoviral E1B-19K protein.

In a specific embodiment, the present invention provides a method for propagating recombinant adenovirus comprising culturing a rAd complementing cell line infected with a recombinant adenovirus (preferably, a replication-defective adenovirus) under conditions so as to permit replication of the viral genome in the cell line, wherein the cell line comprises: (a) a first nucleic acid molecule comprising a nucleotide sequence encoding adenoviral E1A proteins deficient in binding to p300 protein family members and pRb protein family members (see the description above regarding such E1A proteins); and (b) a second nucleic acid molecule comprising a nucleotide sequence encoding an adenoviral E1B-55K protein (and preferably, does not comprise a nucleotide sequence encoding an adenoviral E1B-19K protein). In a preferred embodiment, the present invention provides a method for propagating recombinant adenovirus comprising culturing a rAd complementing cell line infected with a recombinant adenovirus (preferably, a replication-defective adenovirus) under conditions so as to permit replication of the viral genome in the cell line, wherein the cell line comprises: (a) a first nucleic acid molecule comprising a nucleotide sequence encoding adenoviral E1A proteins deficient in binding to p300 protein family members and pRb protein family members (see the description above regarding such E1A proteins); (b) a second nucleic acid molecule comprising a nucleotide sequence encoding an adenoviral E2B polymerase; and (c) a third nucleic acid molecule comprising a nucleotide sequence encoding an adenoviral E1B-55K protein, and preferably, an adenoviral E1B-19K protein.

Recombinant adenovirus of the present invention may be produced by any suitable method, many of which are known in the art (see, e.g., Berkner et al., Nucl. Acids Res. 12:925-941 (1984); Berkner et al. Nucl. Acids. Res. 11:6003-6020 (1983); Brough et al., Virol. 190:624-634 (1992)). In the preferred practice of the invention, the recombinant adenoviruses are derived from the human adenoviridae. In a preferred embodiment of the invention, the recombinant adenovirus is derived from the human adenovirus serotype 2 or 5. In another preferred practice of the invention, the recombinant adenovirus is a replication-defective adenovirus and comprises a mutated genome with a partial or complete (preferably, complete) deletion of E1A coding region (e.g., SEQ ID NO: 17) and E1B coding region (e.g., SEQ ID NO: 18), and may include one or more additional heterologous genes. In another preferred practice of the invention, the recombinant adenovirus is a replication-defective adenovirus and comprises a mutated genome with a partial or complete (preferably, complete) deletion of the E1A coding region (e.g., SEQ ID NO: 17), E1B coding region (e.g., SEQ ID NO: 18), and E2B polymerase coding region (for example, SEQ ID NO: 23), and includes one or more heterologous nucleotide sequences. In a more preferred practice of the invention, the recombinant adenovirus is a replication-defective adenovirus and comprises a mutated genome with a partial or complete (preferably, complete) deletion of the E1A coding region, E1B coding region, E2b polymerase coding region, and E3 coding region, and includes one or more heterologous nucleotide sequences in the deleted E3 coding region. The preferred recombinant adenoviruses of the present invention comprise viral DNA sequences that lack any homology with the adenoviral DNA sequences in the rAd production cell, which reduces the possibility of the viral genome recombining with the cellular DNA to produce RCAs.

In certain embodiments, the quantity of recombinant adenovirus is titrated. Titrating the quantity of the adenovirus in the culture may be performed by techniques known in the art. In a particular embodiment, the concentration of viral particles is determined by the Resource Q assay as described by Shabram, et al. Human Gene Therapy 8:453-465 (1997). As used herein, the term "lysis" refers to the rupture of the virus-containing cells. Lysis may be achieved by a variety of means well known in the art. For example, mammalian cells may be lysed under low pressure (100-200 psi differential pressure) conditions, by homogenization, by microfluidization, or by conventional freeze-thaw methods. Exogenous free DNA/RNA may be removed by degradation with DNAse/RNAse.

Virus-containing cells may be frozen. Virus may be harvested from the virus-containing cells and the medium. In one embodiment, the virus is harvested from both the virus-containing cells and the medium simultaneously. In a particular embodiment, the virus producing cells and medium are subjected to cross-flow microfiltration, for example, as described in U.S. Pat. No. 6,146,891, under conditions to both simultaneously lyse virus-containing cells and clarify the medium of cell debris which would otherwise interfere with virus purification.

As used herein, the term "harvesting" means the collection of the cells containing the recombinant adenovirus from the media and may include collection of the recombinant adenovirus from the media. This may be achieved by conventional methods such as differential centrifugation or chromatographic means. At this stage, the harvested cells may be stored or further processed by lysis and purification to isolate the recombinant virus. For storage, the harvested cells should be buffered at or about physiological pH and frozen at −70° C.

Virus may also be harvested from the virus-containing cells and medium separately. The virus-containing cells may be collected separately from the medium by conventional methods such as differential centrifugation. Harvested cells may be stored frozen or further processed by lysis to liberate the virus. Virus may be harvested from the medium by chromatographic means. Exogenase free DNA/RNA may be removed by degradation with DNAse/RNAse, such as BENZONASE (American International Chemicals, Inc.).

The virus harvest may be further processed to concentrate the virus by methods such as ultrafiltration or tangential flow filtration, for example, as described in U.S. Pat. Nos. 6,146,891; 6,544,769 and 6,783,983.

As used herein, the term "recovering" means the isolation of a substantially pure population of recombinant virus particles from the lysed producer cells and optionally from the supernatant medium. Viral particles produced in the cell cultures of the present invention may be isolated and purified by any method which is commonly known in the art. Conventional purification techniques such as chromatographic or differential density gradient centrifugation methods may be employed. For example, the viral particles may be purified by cesium chloride gradient purification, column or batch chromatography, diethylaminoethyl (DEAE) chromatography (Haruna et al. Virology 13: 264-267 (1961); Klemperer et al, Virology 9: 536-545 (1959); Philipson Virology 10: 459-465 (1960)), hydroxyapatite chromatography (U.S. Patent Application Publication Number US2002/0064860) and chromatography using other resins such as homogeneous cross-linked polysaccharides, which include soft gels (e.g., agarose), macroporous polymers based on synthetic polymers, which include perfusion chromatography resins with large "throughpores", "tentacular" sorbents, which have tentacles that were designed for faster interactions with proteins (e.g., fractogel) and materials based on a soft gel in a rigid shell, which exploit the high capacity of soft gels and the rigidity of composite materials (e.g., Ceramic HyperD® F) (Boschetti, Chromatogr. 658: 207 (1994); Rodriguez, J. Chromatogr. 699: 47-61 (1997)). In the preferred practice of the invention, the virus is purified by column chromatography in substantial accordance with the process of Huyghe, et al. (1995) Human Gene Therapy 6: 1403-1416 as described in Shabram, et al., U.S. Pat. No. 5,837,520 issued Nov. 17, 1998, the entire teaching of which is herein incorporated by reference.

The rAd production cell lines producing virus may be cultured in any suitable vessel which is known in the art. For example, cells may be grown and the infected cells may be cultured in a biogenerator or a bioreactor. Generally, "biogenerator" or "bioreactor" means a culture tank, generally made of stainless steel or glass, with a volume of 0.5 liter or greater, comprising an agitation system, a device for injecting a stream of $CO_2$ gas and an oxygenation device. Typically, it is equipped with probes measuring the internal parameters of the biogenerator, such as the pH, the dissolved oxygen, the temperature, the tank pressure or certain physicochemical parameters of the culture (for instance the consumption of glucose or of glutamine or the production of lactate and ammonium ions). The pH, oxygen, and temperature probes are connected to a bioprocessor which permanently regulates these parameters. In other embodiments, the vessel is a spinner flask, a roller bottle, a shaker flask or in a flask with a stir bar providing mechanical agitation. In another embodiment, a the vessel is a WAVE Bioreactor (WAVE Biotech, Bridgewater, N.J., U.S.A.).

Recombinant adenoviruses may be propagated in the rAd production cell lines of the invention. Virus may be produced by culturing the cells; optionally adding fresh growth medium to the cells; inoculating the cells with the virus; incubating the inoculated cells; optionally adding fresh growth medium to the inoculated cells; and optionally harvesting the virus from the cells and the medium. Typically, when the concentration of viral particles, as determined by conventional methods, such as high performance liquid chromatography using a Resource Q column, as described in Shabram, et al. Human Gene Therapy 8:453-465 (1997), begins to plateau, the harvest is performed.

Proteins produced by recombinant adenoviruses grown in the rAd production cell lines of the invention (e.g., adenovirus comprising a deletion of the E1A and E1B coding regions and comprising a heterologous nucleotide sequence, or adenovirus comprising a deletion of E1A, E1B and E2B polymerase coding regions and comprising a heterologous nucleotide sequence) may also be isolated and purified. Proteins, polypeptides and peptides may be purified by standard methods, including, but not limited to, salt or alcohol precipitation, affinity, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "*Guide to Protein Purification*", *Methods in Enzymology*, Vol. 182, M. Deutscher, Ed., 1990, Academic Press, New York, N.Y.

5.5 Utility of Recombinant Adenovirus

The recombinant adenoviruses of the invention can be used in vitro to express proteins, polypeptides and peptides of interest. The recombinant adenoviruses of the invention can also be used in gene therapy. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215.

The recombinant adenoviruses can be used for in vivo or ex vivo gene therapy. For in vivo gene therapy, recombinant adenovirus is directly administered to a subject. For ex vivo gene therapy, cells are infected with the recombinant adenovirus in vitro and then the infected cells are transplanted into the subject. In a specific embodiment, the recombinant adenovirus is directly administered in vivo, where a protein of interest is expressed.

In another embodiment, a cell is infected with a recombinant adenovirus and the resulting recombinant cell is administered to a subject. The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art. In accordance with the invention, any cells which can be infected with a recombinant adenovirus can be for purposes of gene therapy. Non-limiting examples include epithelial cells (e.g., respiratory epithelial cells), endothelial cells, keratinocytes, fibroblasts, muscle cells, hepatocytes, blood cells (such as T lymphocytes, B lymphocytes, monocytes, macrophages, neutrophils, eosinophils, megakaryocytes, granulocytes), and various stem or progenitor cells (in particular, hematopoietic stem or progenitor cells, e.g., as obtained from bone marrow, umbilical cord blood, peripheral blood, fetal liver, etc.). In a preferred embodiment, the cell used for gene therapy is autologous to the subject. In an embodiment in which recombinant cells are used in gene therapy, the proteins encoded by the genome of the recombinant adenovirus are expressible by the cells or their progeny, and the recombinant cells are then administered in vivo for therapeutic effect.

The recombinant adenovirus of the present invention may be used to immunize a subject. For example, the recombinant adenovirus may be used to generate antibodies against a heterologous antigen expressed by the recombinant adenovirus. The amount of recombinant adenovirus to be used to immunize a subject and the immunization schedule will be determined by a physician skilled in the art and will be administered by reference to the immune response and antibody titers of the subject.

The antibodies generated against an antigen by immunization with a recombinant adenovirus may used in diagnostic immunoassays, passive immunotherapy, and generation of anti-idiotypic antibodies. The generated antibodies may be isolated by standard techniques known in the art (e.g., immunoaffinity chromatography, centrifugation, precipitation, etc.) and used in diagnostic immunoassays. The antibodies may also be used to monitor treatment and/or disease progression. Any immunoassay system known in the art may be used for this purpose including, but not limited to, competitive and noncompetitive assay systems using techniques such as radioimmunoassays, ELISA (enzyme-linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The recombinant of the present invention can be used to produce antibodies for use in passive immunotherapy, in which short-term protection of a subject is achieved by the administration of pre-formed antibody directed against a heterologous antigen. The antibodies generated by the recombinant adenovirus of the present invention can also be used in the production of anti-idiotypic antibody. The anti-idiotypic antibody can then in turn be used for immunization, in order to produce a subpopulation of antibodies that bind the initial antigen (Jerne, 1974, Ann. Immunol. (Paris) 125c:373; Jerne et al., 1982, EMBO J. 1:234).

In certain embodiments, the antibody produced by immunization with a recombinant adenovirus is modified prior to administration to a subject. For example, the antibody may be humanized and/or affinity matured.

5.6 Compositions and Methods of Administering Recombinant Adenovirus

The invention encompasses compositions comprising a recombinant adenovirus (preferably, replication-defective recombinant adenovirus) generated by the methods of the invention. In a preferred embodiment, the compositions are pharmaceutical compositions suitable for administration to a subject.

The pharmaceutical compositions of the present invention comprise an effective amount of recombinant adenovirus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain an effective amount of recombinant adenovirus, preferably in purified form, together with a suitable amount of carrier so as to provide the form for proper administration to the patient. The formulation should suit the mode of administration.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Methods of administration of the compositions include, but are not limited to, intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the lungs by any suitable route. Pulmonary administration can be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249: 1527-1533).

In a specific embodiment, a composition of the invention is a vaccine or immunizing composition comprising a recombinant adenovirus (preferably, replication-defective recombinant adenovirus) generated by the methods of the invention, and a suitable excipient. Many methods may be used to introduce the vaccine compositions, these include but are not limited to intranasal, intratracheal, oral, intradermal, intramuscular, intraperitoneal, intravenous, and subcutaneous routes. It may be preferable to introduce the recombinant adenovirus vaccine composition via the natural route of infection of adenovirus.

5.7 Plasmid Systems

The present invention provides plasmid systems for generating cell lines for production of recombinant adenovirus. In a specific embodiment, the present invention provides a plasmid system for generating a cell line (preferably, a human cell line) for the production of recombinant adenovirus comprising in separate containers: (a) a first expression cassette comprising a regulatory element operably linked to a first nucleic acid molecule comprising a nucleotide sequence encoding adenoviral E1A proteins deficient in binding to p300 protein family members and pRb protein family members; and (b) a second expression cassette comprising a regulatory element in said cell line operably linked to a second nucleic acid molecule comprising a nucleotide sequence encoding an adenoviral E1B-55K protein. In an alternative embodiment, the plasmid system comprises a single expression cassette that comprises a nucleic acid molecule comprising a nucleotide sequence encoding adenoviral E1A proteins deficient in binding to p300 protein family members and pRb protein family members and a nucleotide sequence encoding an adenoviral E1B-55K protein.

In a specific embodiment, the present invention provides a plasmid system for generating a cell line (preferably, a human cell line) for the production of recombinant adenovirus comprising in separate containers: (a) a first expression cassette comprising a regulatory element operably linked to a first nucleic acid molecule comprising a nucleotide sequence encoding adenoviral E1A proteins deficient in binding to p300 protein family members and pRb protein family members; (b) a second expression cassette comprising a regulatory element operably linked to a second nucleic acid molecule comprising a nucleotide sequence encoding an adenoviral E2B polymerase; and (c) a third expression cassette comprising a regulatory element operably linked to a third nucleic acid molecule comprising a nucleotide sequence encoding an adenoviral E1B-55K protein. In an alternative embodiment, the plasmid system comprises a single expression cassette that comprises a nucleic acid molecule comprising (i) a nucleotide sequence encoding adenoviral E1A proteins deficient in binding to p300 protein family members and pRb protein family members, (ii) a nucleotide sequence encoding an adenoviral E1B-55K protein and (iii) a nucleotide sequence encoding an adenoviral E2B polymerase.

In another embodiment, the present invention provides a plasmid system for generating a cell line (preferably, a human cell line) for the production of recombinant adenovirus comprising in separate containers: (a) a first expression cassette comprising a regulatory element operably linked to a first nucleic acid molecule comprising a nucleotide sequence encoding adenoviral E1A proteins deficient in binding to p300 protein family members and pRb protein family members; (b) a second expression cassette comprising a regulatory element operably linked to a second nucleic acid molecule comprising a nucleotide sequence encoding an adenoviral E2B polymerase; and (c) a third expression cassette comprising a regulatory element operably linked to a third nucleic acid molecule comprising a nucleotide sequence encoding an adenoviral E1B-55K protein and an adenoviral E1B-19K protein. In an alternative embodiment, the plasmid system comprises a single expression cassette that comprises a nucleic acid molecule comprising (i) a nucleotide sequence encoding adenoviral E1A proteins deficient in binding to p300 protein family members and pRb protein family members, (ii) a nucleotide sequence encoding adenoviral E1B-55K and E1B-19K proteins and (iii) a nucleotide sequence encoding an adenoviral E2B polymerase In a specific embodiment, the E1A proteins encoded by the first expression cassette comprise: (a) a first deletion corresponding to: (i) amino acid residues 4-25 of an E1A 289R protein (dl1101) and amino acid residues 4-25 of an E1A 243R protein (dl1101); or (ii) amino acid residues 36-49 of an E1A 289R protein and amino acid residues 36-49 of an E1A 243R protein; and (b) a second deletion corresponding to: (i) amino acid residues 111-123 (dl1107) of an E1A 289R protein and amino acid residues 111-123 (dl1107) of an E1A 243R protein; or (ii) amino acid residues 124-127 (dl1108) of an E1A 289R protein and amino acid residues 124-127 (dl1108) of an E1A 243R protein.

EXAMPLES

The following examples are merely illustrative and not meant to be limiting of the scope of the invention described herein.

Example 1

Generation an E1A and E1b Complementing Cell Line and Use of the Cell Line in the Production of Recombinant Adenovirus This example demonstrates the utility of an E1A and E1b complementing cell line for the production of high titers of replication-defective, helper-independent recombinant viruses.

I. Materials & Methods

Cell Culture 293 (ATCC# CRL-1573), A549 (ATCC# CCL-185) and HeLa (ATCC# CCL-2) cells were obtained from the American Type Culture Collection (ATCC, Manassas, Va.). Cell lines were cultured in Dulbecco's Modified Eagle Medium (DMEM) supplemented with 10% (v/v) fetal bovine serum (JRH Biosciences, Lenexa, Kans.), 1% (v/v) antibiotic-antimycotic solution (Cellgro, Kansas, Mo.) and 1 mM sodium pyruvate (BioWhittaker, Inc., Walkersville, Md.).

Plasmids

The Ad5 wild-type E1A gene, and E1A sequences containing the E1Adl1101, E1Adl1107 and E1Adl01/07 mutations were cloned by standard procedures from pXC1 (McKinnon et al., (1982) Gene 19:33-42) or Ad-dl01/07 (Howe et al., (1990) Proc. Natl. Acad. Sci. USA 87:5883-5887) into the RSV promoter/SV40 polyA expression cassette of pRc/RSV-Neo (Invitrogen, Carlsbad Calif.) to create pRc/RSV-E1Awt, pRc/RSV-E1Adl1101, pRc/RSV-E1Adl1107 and pRc/RSV-E1Adl01/07. pcDNA3.1-E1B-55K, was constructed by cloning the E1B-55K gene from PXC1 using PCR into the CMV promoter/BGH poly A expression cassette of pcDNA3.1-hygro (Invitrogen Carlsbad, Calif.). p53con-luc contained 4 consensus p53 binding sites, and a TATA box from the simian virus-40 (SV40) early promoter (Ramachandra et al., (2001) Nat. Biotechnol. 19: 1035-1041), upstream of the luciferase gene in pGL3-basic (Promega, Madison, Wis.). pE2F-luc contained 4 copies of the E2F binding sites from the adenovirus early region 2 promoter and an SV40 TATA box upstream of the luciferase gene in pGL3-basic.

Viral Constructs rAd-β-gal and rAd-GFP were E1/E3 deleted adenovirus vectors with expression cassettes inserted into the E1-deletion and which contained either the β-galactosidase (β-gal) gene, or green fluorescent protein (GFP) gene, under control of the constitutively active CMV immediate early promoter (Cheney et al., (1998) Cancer Res. 58:2331-2334; Wills et al, (1994) Hum. Gene Ther. 5:1079-1088). The p53 reporter rAd-PRE-GFP contained an expression cassette in the E3-deletion in which a p53-response element (Ramachandra et al, (2001) Nat. Biotechnol. 19:1035-1041) regulated expression of GFP. Ad5-dl309 (Jones and Shenk, (1979) Proc. Natl. Acad. Sci. 76:3665-3669) was used as a wild-type control virus. The Ad5-dl309 based mutant viruses E1B/19K−, which does not produce the E1B-19K protein (Marcellus et al, (1996) J. Virol. 70:6207-6215), and NT1010, which has a large deletion in the E1A region (Whyte et al, (1989) Cell 56:67-75), have been described previously. dl1520 (Barker and Berk, (1987) Virology 156:107-121) was a chimeric adenovirus (Ad2 and Ad5-dl309) containing a deletion in the E1B coding region (Ad5 coordinates 2496-3233) and a stop codon at the third codon of E1B-55K. The Ad-E1B- virus was constructed by removing the E1B coding region in plasmid pXC1 by EcoIVI and BglII digestion, Klenow fill in and blunt end ligation to create pXC1-E1B-. Ad sequence containing the mutated E1B region was transferred from pXC1-E1B⁻ into a larger transfer plasmid pTG9530 (Transgene S. A., Strasbourg), to create pTG9530-E1B⁻. Homologous recombination in E. coli strain BJ5183 (Chartier et al., (1996) J. Virol. 70:4805-4810) was used to generate infectious Ad-E1B⁻ adenoviral DNA by transformation of pTG9530-E1B⁻ and viral plasmid pTG4213-Ad5-dl309. The resulting Ad-E1B⁻ plasmid was isolated and transfected into 293 cells to generate virus. All viruses were purified by column chromatography using a method described previously (Huyghe et al., (1995) Hum. Gene Ther. 6:1403-1416). Particle concentrations were estimated by an ion exchange HPLC-based method (RQ-HPLC) that determines concentrations of intact adenovirus particles relative to an internal adenovirus standard (Shabram et al, (1997) Hum. Gene Ther. 8:453-465).

Selection of A549 Cell Clones Expressing E1Awt, E1A-Mutant Proteins and E1B-55K

For selection of clones expressing E1Awt or E1A-mutant proteins plasmids pRc/RSV-E1Awt, pRc/RSV-E1A1101, pRc/RSV-E1A1107 and pRc/RSV-E1A01/07 were transfected into A549 cells using Superfect reagent (Qiagen, Valencia Calif.). After incubation for two days, selection was initiated in growth medium containing 350 µg/ml neomycin (Invitrogen, Carlsbad, Calif.). Drug-resistant colonies from the cultures transfected with the E1Awt, or E1A-mutant selection plasmids, were trypsinized, established as cell pools, and dilution cloned in 96-well plates. Selection in culture medium containing neomycin was carried out three more weeks, after which 48 individual clones from each transfection were expanded and screened for virus production potential. A549-E1Adl01/07-4 based cell lines were engineered to express E1B-55K using the same procedure except that A549-E1Adl01/07-4 cells were transfected with pcDNA3.1-E1B-55K and selected in 350 µg/ml hygromycin (Invivogen, San Diego, Calif.)

Generation of the E1-Complementing Cell Line

Figure 2:
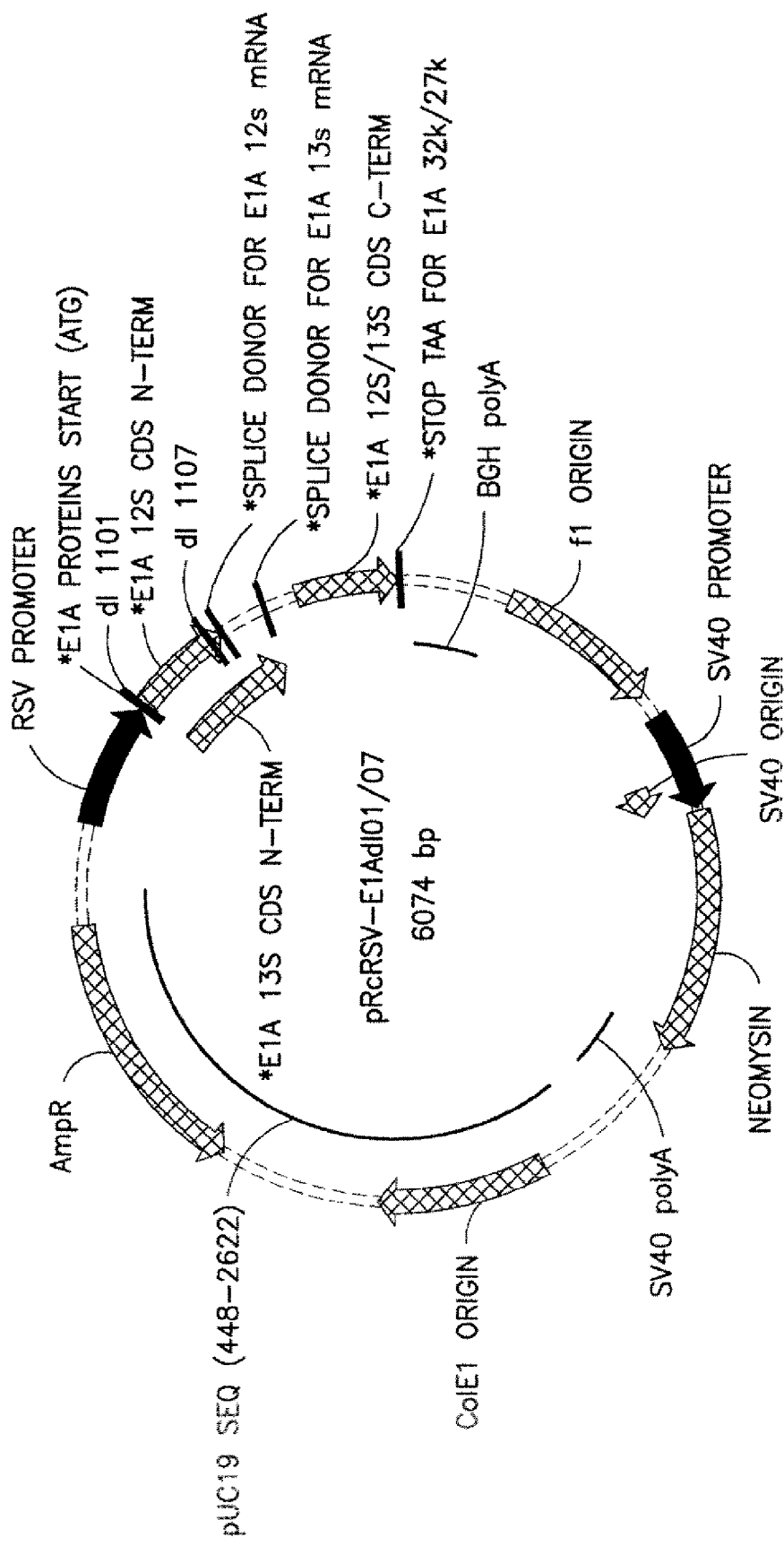
FIG. 2. Plasmid map of pRcRSV-E1Ad|01/07.
RSV promoter: Start:209 End:605
BGH poly A signal: Start:1556 End:1782
f1 origin: Start:1838 End:2360
SV40 promoter: Start:2422 End:2747
SV40 origin: Start:2616 End:2701
Neomycin resistance gene: Start:2753 End:3547

The Ad5 E1A sequences containing the E1Adl01/07 mutation were cloned by standard procedures from Ad-dl01/07 (Howe et al., (1990) Proc. Natl. Acad. Sci. USA 87:5883-5887) into the RSV promoter/SV40 polyA expression cassette of pRc/RSV-E1A to create pRc/RSV-E1Adl01/07. See FIG. 2 for a map of pRc/RSV-E1Adl01/07. pcDNA3.1-E1B-55K was constructed by cloning the E1B-55K gene from pXC1 (McKinnon et al., (1982) Gene 19:33-42) using PCR into the CMV promoter/BGH poly A expression cassette of pcDNA3.1-hygro (Invitrogen Carlsbad, Calif.). See FIG. 3 for a map of pcDNA3.1-E1B-55K.

The plasmid pRc/RSV-E1A01/07 was transfected into A549 cells using Superfect reagent (Qiagen, Valencia Calif.). After incubation for two days, selection was initiated in growth medium containing 350 µg/ml neomycin (Invitrogen, Carlsbad, Calif.). Drug-resistant colonies from the transfected cultures were trypsinized, established as cell pools, and dilution cloned in 96-well plates. Selection in culture medium containing neomycin was carried out three more weeks, after which 48 individual clones from the transfection were expanded and screened for virus production potential. The plasmid pcDNA3.1-E1B-55K was transfected into A549-E1Adl01/07-4, a transformed cell line, using Superfect reagent. After incubation for two days, selection was initiated in growth medium containing hygromycin (350 µg/ml) (Invivogen, San Diego, Calif.). Drug-resistant colonies from the transfected cultures were trypsinized, established as cell pools, and dilution cloned in 96-well plates. Selection in culture medium, Dulbecco's Modified Eagle Medium (DMEM) supplemented with 10% (v/v) fetal bovine serum (JRH Biosciences, Lenexa, Kans.), hygromycin (200 µg/ml) and neomycin (200 µg/ml), was carried out three more weeks, after which 48 individual clones from the transfection were expanded and screened for virus production potential.

Screening Procedures for Cells Clones

The virus production potential of A549-based clones expressing E1Awt or E1A-mutant proteins was assessed by infecting cells that were plated on 6-well plates with rAd-GFP ($1\times10^8$ particles/ml). Virus replication efficiency was estimated by monitoring green fluorescence protein intensity and cytopathic effect (CPE). For screening E1A01/07-4 based clones established by transfection with pcDNA3.1-E1B-55K cells were infected with rAd-PRE-GFP ($1\times10^8$ particles/ml) and clones with low GFP intensity, suggesting reduced p53 activity, and robust CPE were chosen for further characterization.

Virus production in the selected clones was determined by measuring the number of particles produced on a per cell basis. For this assay, cells were infected with rAd vector at 5×10e8 particles/ml, and at the time of infection cells in duplicate plates or flasks were trypsinized and counted using a Coulter Counter (Beckman-Coulter, Miami, Fla.). At a time point when the infection was complete (3-4 days) cells, and media were collected, freeze/thawed three times and centrifuged to remove cellular debris. The particle concentration in the cleared lysates was determined using anion-exchange high-performance liquid chromatography (Shabram et al., (1997) Hum. Gene Ther. 453-465).

Western Blotting Analysis to Determine E1A Protein Levels

Whole cell protein lysates were prepared by incubation of the indicated cells in lysis A buffer (50 mM Tris [pH 8.0], 150 mM NaCl, 0.5% [vol/vol] IGEPAL CA-630 [Sigma, St. Louis, Mo.] and protease-inhibitor cocktail [Roche, Indianapolis, Ind.]) followed by centrifugation. Total protein concentration in the lysates was determined by the Bio-Rad protein assay (Bio-Rad, Hercules, Calif.) and 50 μg aliquots were separated by sodium dodecyl sulfate-polyacrylamide gel electrophoresis (SDS-PAGE) with gradient (4%-12%) NUPAGE gels (Invitrogen, Carlsbad, Calif.). After transfer onto PVDF membranes (Invitrogen, Carlsbad, Calif.) western detection was performed using antibodies specific for E1A (M73, Calbiochem, La Jolla, Calif.) or α-actin (Sigma-Aldrich, St. Louis, Mo.). Binding patterns were determined by incubating the membranes with horseradish peroxidase-conjugated anti-mouse immunoglobulin G and M (Roche, Indianapolis, Ind.) and detected by enhanced chemiluminesce (Amersham BioSciences, Piscataway, N.J.).

Analysis of Viral DNA

Small molecular weight DNA was isolated from cells infected with rAd-β-gal (1×10e8 particles/ml) on 6-well plates at the indicated time points using a modified Hirt extraction (Hirt, 1967). Infected cells were harvested by scraping and lysed in TNE buffer [500 mM NaCl, 10 mM Tris (7.5), 10 mM EDTA, 1% SDS, 0.5 mg/ml proteinase K (Sigma), 0.25 mg/ml pronase E (Sigma)]. After a freeze-thaw cycle lysates were cleared by centrifugation, extracted with a phenol:chloroform mixture (Sigma, St. Louis, Mich.) and ethanol precipitated. The nucleic acid pellets were suspended in 60 μl of TE containing RNase (Ambion, Austin, Tex.), after which 12 μl samples were restricted with XhoI, separated on 1% agarose gels. DNA restriction patterns were visualized by ethidium bromide staining.

Flow Cytometric Determination of Apoptosis with FITC-VAD-FMK

E1Awt, E1A-mutant clones and A549 control cells were plated on 6-well plates at 150,000 cells per well and infected at 24 hours with rAd-β-gal (1×10$^8$ particles/ml). At 20 hours after infection, 5 μM CaspACE FITCTM-VAD-FMK (Promega, Madison, Wis.) was added directly to the culture medium. After incubation for 20 minutes at 20° C., the cells were trypsinized, washed two times with PBS and fixed in 0.5% fomaldehyde for 30 minutes at 20° C. Flow cytometry analysis was performed using an FACSCalibur (Becton Dickinson, San Jose, Calif.) and fluorescence was measured at 530 nm (excitation of 488 nm).

Luciferase Assays

Lysates of cells transfected with reporter plasmids using Superfect (Qiagen, Valencia, Calif.) were mixed with the reconstituted luciferase substrate (Promega, Madison, Wis.) according to the manufactures specifications. Luciferase activity of each lysate was determined using an Analyst AD (Molecular Devices, Sunnyvale, Calif.).

Immunoprecipition of E1B-55K

Protein lysates (1 mg total protein), prepared as described above, were pre-cleared with protein-G sepharose beads (Amersham BioSciences, Piscataway, N.J.) and incubated with 5 μg of the E1B-55K specific mouse monoclonal antibody, 2A6 (Sarnow et al., (1982) Cell 28:387-394). E1B-55K-immunoglobulin complexes were purified on protein-G sepharose, washed extensively with lysis buffer and incubated with SDS-PAGE sample buffer containing reducing agent (Invitrogen, Carlsbad, Calif.). The samples were separated on SDS-PAGE gels and E1B-55K protein was detected by Western blot as described above, using the 2A6 monoclonal antibody.

Serial Passage of an E1-Deleted rAd-Vector in 293 or SL0003

The rAd-β-gal virus to be used for serial passage was first plaque purified three times, propagated using SL0003 cells grown in a cell factory (Nunc A/S, Kamstrupvej, Denmark) and purified by column chromatography. The resulting virus stock, rAd-β-gal (p0), tested free of replication competent adenovirus (RCA) using the 21-day bioassay described below. For the first serial passage, cell factories containing 293 or SL0003 were infected with purified rAd-β-gal (p0) at 5×10e8 particles/ml. Cell lysates, prepared when the infections were complete were used to infect a second set of fresh 293 or SL0003 cells seeded in cell factories. Lysates for infection of passages 2 to 5 were prepared similarly and at passage 5, virus was purified by column chromatography.

Assay for RCA

A modified bioassay based on a previously described protocol (Zhu et al., (1999) Hum. Gene Ther. 10:113-121) was used to detect RCA using 1×10e11 total particles of rAd-β-gal purified after propagation in 293 or SL0003. For the initial RCA bioassay infection, 10-T225 flasks were each seeded with 1×10e7 cells of A549 cells and infected, 24 hours later with 1×10e10 particles per flask of rAd-β-gal prepared from 293 or SL0003 cells. After three days, a cell lysate was prepared from the infected A549 cells and used to infect a second set of flasks that had been seeded with 3×10e6 A549 cells. For the second infection, the rAd-β-gal and control lysates from the first infections were divided in half and used to infect a set of 5-T225 flasks. At 12 days after the initial infection, lysates from the second round of infections were prepared. Each lysate was divided in half and used to infect 5 flasks seeded with 3×10e6 A549 cells and incubated for 9 more days. Control samples included Ad5 wild-type (6 virus particles per 10 flasks) and 1×10e11 virus particles of rAd-β-gal spiked with 6 virus particles of Ad5 wild-type. Both the spiked and wild-type adenovirus controls were required to produce CPE during the 21 day infection. If CPE was observed in the rAd-β-gal samples during the bioassay, low molecular weight DNA was isolated from approximately 1×10e7 cells for viral DNA analysis.

II. Results

Production Levels

Virus production potential in selected cell lines was assessed by infection with the replication competent virus Ad5-dl309. A549 cells and HeLa cells produced virus at 558,000 and 444,000 particles/cell, respectively. Other lines tested including, DLD-1, U87MG, MDA468 and IGROV-1, all produced less than 120,000 particles/cell. 293 cells produced Ad5-dl309 virus at 139,000 particles/cell and rAd-β-gal virus at 127,000 particles/cells. The production capacity for Ad5-dl309 in HeLa and A549 cell lines suggested that these human tumor lines were the best candidates for use in development of E1-complementing cell lines.

Complementation of E1A in A549 Cells

Figure 1:
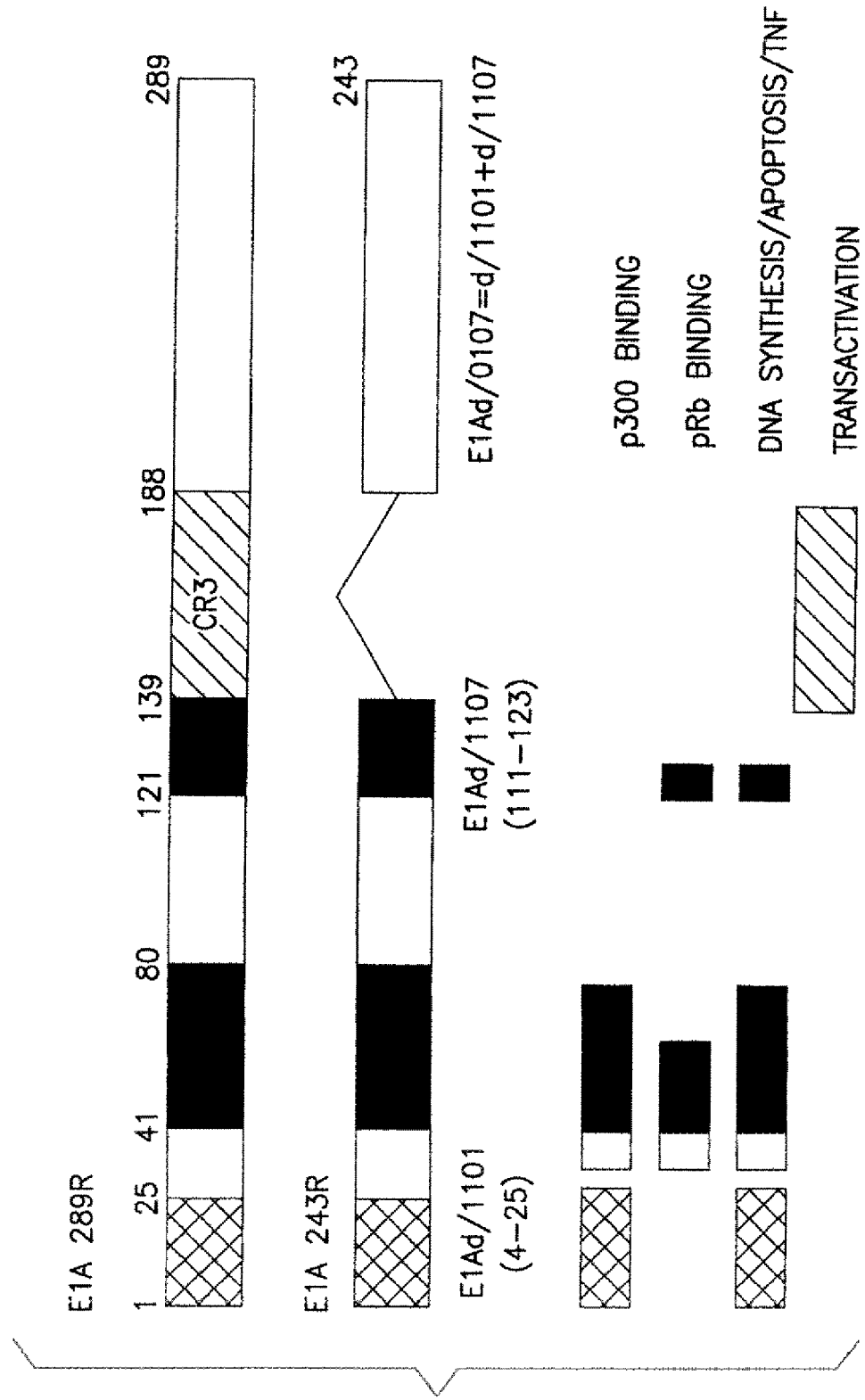
FIG. 1 is a schematic diagram of the functional domains of the 243R and 289R E1A proteins. Regions required for binding of the cellular proteins p300/CBP and pRb are indicated as are domains necessary for activation of cellular apoptosis, induction of cell cycle progression in quiescent cells and transcriptional activation of the adenovirus early gene regions.

Expression of wild-type E1A has been reported to reduce the proliferative capacity of A549 cells and leads to apoptosis under serum-depleted conditions (Hubberstey et al., (2002) Cancer Gene Ther. 9:321-329. To limit the toxicities associated with E1A expression in A549 cells, several E1A mutants were tested for stable expression and complementation of E1 function for rAd vector production. The E1A mutants used, E1Adl1101, E1Adl1107 and E1Adl01/07, carried deletions in regions of E1A proteins that were required for induction of cell cycle progression and apoptosis (FIG. 1) but did not compromise the E1A transactivation domain required for stimulation of the other early virus promoters. Specifically, the E1Adl1101 and E1Adl1107 mutants were defective for binding to the cellular proteins p300/CBP and pRb, respectively, whereas the E1Adl01/07 mutant was defective for binding both cellular proteins.

Plasmids expressing either E1Adl1101, E1Adl1107, E1Adl01/07 or wild-type E1A under control of an RSV promoter were used to transfect A549 cells. The plasmids also contained a neomycin resistance gene as a selectable marker. Individual clones from pools of G418 resistant cells were isolated and screened by infection with rAd-GFP. The level of GFP expression was visually examined in 48 clones and then five clones were selected for further characterization. The production capacity of each clone (A549E1Adl1101-1 to A549E1Adl1101-5, A549E1Adl1107-1 to A549E1Adl1107-5, A549E1Adl01/07-1 to A549E1Adl01/07-5, A549E1Awt-1 to A549E1Awt-5) was determined by quantification of rAd-GFP particles produced per cell as described herein. Results of the production assays (see Table 2) show that the cell clones expressing either E1Awt, or E1Adl1101, had low virus productivity. Cell clones isolated from the E1Adl1107 generally gave poor production yields, with the exception of cell clone E1Adl1107-1 which had a yield of over 20,000 particles per cell. In contrast, cell clones isolated from the E1Adl01/07 transfection pool had the highest production yields as four of the five cell clones assayed yielded particle concentrations between 20,000 and 30,000 per cell.

TABLE 2 rAd-GFP yield from indicated cell clones (virus particles/cell)

| Cell Clone # | Clone and E1A Status | | | |
| --- | --- | --- | --- | --- |
| | E1Adl1101 | E1Adl1107 | E1Adl01/07 | E1Awt |
| Clone #1 | 2700 | 21000 | 7800 | 1800 |
| Clone #2 | 2200 | 800 | 25000 | 400 |
| Clone #3 | 800 | 4200 | 23000 | 0 |
| Clone #4 | 3600 | 1200 | 32000 | 800 |
| Clone #5 | 1200 | 1200 | 20000 | 700 |

Measurement of E1A Protein Levels in E1A Expressing A549 Clones

E1A protein levels in the selected clones (E1Adl1101-1 to E1Adl1101-5, E1Adl1107-1 to E1Adl1107-5, E1Adl01/07-1 to E1Adl01/07-5, E1Awt-1 to E1Awt-5) were determined by Western blot analysis using an E1A-specific monoclonal antibody (Harlow et al., (1985) J. Virol. 55:533-546) that recognized an epitope in the C-terminal region of E1A. This epitope was unaffected by the dl1101 and dl1107 mutations. Western analysis showed that expression levels of E1A proteins varied greatly between the clones. In addition, the amount of wild-type or mutant E1A protein expressed did not correlate with the production yields. All cell clones expressing wild-type E1A or the E1Adl1101 mutant were inefficient producers regardless of the amount of E1A protein expressed. Among the E1Adl1107 cell clones only E1Adl1107-1 was an efficient producer despite expressing nearly undetectable levels of E1A protein. The E1Adl1107-1 cell clone was not further analyzed as it grew poorly, a characteristic undesirable in a production cell line. The E1Adl01/07 cell clones also displayed various levels of protein with the best producer cell clone E1Ad01/07-4 expressing lower levels as compared to E1Adl01/07-5, which had comparatively high levels.

Analysis of Viral Replication and Apoptosis after Infection

The E1Awt-2 and E1Adl01/07-5 cell clones, which expressed similar levels of E1A proteins, were selected to further characterize the biological basis for the different production yields. Because the E1Adl01/07-4 cell clone produced viral particles more efficiently than any other line (see Table 2), it was also selected for further characterization.

The ability of the A549-E1Awt-2 and the two A549-E1Adl01/07 cell clones (E1Adl01/07-4 and E1Ad01/07-5) to support replication of an E1-deleted virus rAd-β-gal virus was analyzed by restriction enzyme digest of low molecular weight DNA from infected cells. Restriction analysis indicated that there were differences in the quantity and quality of viral DNA isolated from the various cell lines. The quality of rAd-β-gal DNA from the E1Adl01/07 cell clones was comparable to 293 cell isolated viral DNA. Extremely low levels of rAd-β-gal viral DNAs were produced from the E1Awt-2 clone, and the DNA that was isolated smeared on the agarose gel with DNA fragmentation suggesting high levels of apoptosis in these cells.

Analysis of viral DNA produced from clone E1Awt-2 suggested that apoptosis could be occurring, potentially limiting the amount of virus produced. A FITC-VAD-FMK peptide was used to measure caspase activity by flow cytometry as an indicator of apoptotic cell death after infection. As shown in Table 3 almost half of the E1Awt-2 cells were apoptotic 20 hours after infection, whereas apoptosis was not induced in the E1Ad01/07-4 and E1Adl01/07-5 cell clones. Together these results suggest that viral infection of the E1Awt-2 cells induces premature apoptosis, limiting viral DNA replication and subsequent virus particle production.

TABLE 3

Percentage of apoptotic cells at 20 hours after infection with rAd-β-gal

| Experiment | Clone | | | Control |
| --- | --- | --- | --- | --- |
| | E1Awt-2 | E1Adl01/07-4 | E1Adl01/07-5 | A549 |
| Experiment 1 | 49% | 4% | 6% | 1% |
| Experiment 2 | 49% | 6% | 7% | 2% |

Status of the E2F and p53 Transcription Factors in E1Awt and E1Adl01/07 Cell Clones Induction of apoptosis by E1A has been shown to be linked to binding of pRb and p300/CBP, resulting in activation of the E2F and p53 transcription factors (Querido et al., (1997) J. Virol. 71: 3526-3533). To measure E2F and p53 activity levels in the selected production cell clones, reporter plasmids were constructed in which a luciferase gene was placed under control of either a consensus p53 promoter or an E2F promoter. p53 and E2F promoter activities were found to be elevated in the E1Awt-2 clone (see Table 4). In contrast, p53 and E2F activity levels in the E1Adl01/07-4 and E1Adl01/07-5 clones were similar to the control A549 cells.

TABLE 4

Activation of the p53 and E2F transcription factors in the indicated cell clones (relative fluorescence units × 1e+6)

| Reporter Plasmid | Clones | | | Control |
|---|---|---|---|---|
| | E1Awt-2 | E1Adl01/07-4 | E1Adl01/07-5 | A549 |
| p53-luciferase | 3.7 +/− 0.22 | 0.81 +/− 0.14 | 0.53 +/− 0.06 | 1.29 +/− 0.22 |
| E2F-luciferase | 4.7 +/− 0.19 | 0.53 +/− 0.17 | 0.32 +/− 0.006 | 1.36 +/− 0.18 |

Complementation of E1B in E1Adl01/07-4

Although the E1Adl01/07-4 clone was capable of producing replication defective adenovirus in small scale format, it was reasoned that the yield may be further improved by complementation using E1B. To study the production yield of E1Adl01/07-4 cells after E1B complementation, E1Adl01/07-4 cells were infected, at two different concentrations (1×10e8 particles/ml and 5×10e8 particles/ml), with a series of E1 adenovirus mutants to express E1B-19K and E1B-55K either individually or together. It was found that infection of E1Adl01/07-4 cells of a virus that produces a non-functional truncated E1A and wild-type E1B (Ad-NT1010) yielded virus comparable to Ad5-dl309 (see Table 5). In contrast, a mutant virus that expressed E1A but no E1B (AdE1B−) yielded only about 55,000 particles per cell after infection at both concentrations of test virus. These results suggested that complementation of E1B increases production yield. To further define the contribution of the E1B region, viruses expressing either E1B-19K (dl1520) or E1B-55K (AdE1B-19K−) alone were tested for growth on E1Adl01/07-4 cells. The E1B-19K expressing virus productivity was considerably lower than Ad5-dl309 whereas the E1B-55K expressing virus produced at levels higher than Ad5-dl309.

TABLE 5

Virus yield from E1Adl01/07-4 cells after infection with various E1− mutant adenovirus (E1A, E1B-19K, E1B-55K status indicated)

| | | Virus | | | | |
|---|---|---|---|---|---|---|
| | | dl309 | dl1520 | E1B19K− | E1B− | NT1010 |
| Status | E1A | + | + | + | + | − |
| | E1B-55K | + | − | + | − | + |
| | E1B-19K | + | + | − | − | + |
| Virus Yield | Yield (1e+8 p/ml) | 155000 | 86000 | 231000 | 55000 | 177000 |
| | Yield (5e+8 p/ml) | 242000 | 84000 | 306000 | 58000 | 261000 |

These results suggested that addition of an E1B-55K gene increases the viral yield in the E1Adl01/07-4 cell line. Use of only the E1B-55K coding sequences may further reduce the possibility of generating RCA during rAd production. A selection plasmid was used in which the E1B-55K gene was cloned under control of the CMV promoter (pcDNA-55K) to complement E1B-55K function in E1Adl01/07-4 cells. The sequence of the expression cassette in pcDNA-55K was verified by DNA sequencing and expression of intact E1B-55K protein was demonstrated by transient transfection in HeLa cells.

A549E1Adl01/07-4 cells were transfected with pcDNA-55K, which also carried a hygromycin resistance marker, and individual clones (A549E1Adl01/07-4-E1B-55K-1 to A549E1Adl01/07-4-E1B-55K-6) were selected from the drug-resistant pool by dilution cloning. Clones were screened for E1B-55K function using an immunofluorescent assay that measured inhibition of a p53 responsive promoter (PRE) controlling GFP expression carried in a replication defective adenovirus named rAd-PRE-GFP. In cells expressing wild type p53, such as the parental A549E1Adl01/07-4 line, GFP was expressed at high levels from rAd-PRE-GFP. In contrast, expression of GFP from rAd-PRE-GFP was low in 293 cells (control) and A549E1Adl01/07-4-E1B-55K cells, which express E1B-55K and wild-type p53. Several clones including A549E1Adl01/07-4-E1B-55K-2 were selected using this assay and further characterized for E1B-55K expression and virus production.

Similar levels of E1B-55K protein were detected by immunoprecipitation, with the E1B-55K specific monoclonal antibody 2A6, in cell lysates from all of the selected clones (A549E1Adl01/07-4-E1B-55K-1 to A549E1Adl01/07-4-E1B-55K-6) and one clone A549E1Adl01/07-4-E1B-55K-2, hereafter designated SL0003, was selected for further characterization based on its growth properties and virus production.

Cell line stability is important for pharmaceutical scale-up production and therefore the virus growth capacity of SL0003 cells was evaluated during 20 cell culture passages. Table 6 shows that SL0003 cells assayed at passage 5, 15 and 20 produced rAd-β-gal virus at an average of about 96,000 particles per cell.

TABLE 6 rAd-β-gal yield from SL0003 cells

| SL0003 Passage No. | Particle No. (+/− Std.Dev.) |
|---|---|
| 5 | 88800 +/− 2800 |
| 15 | 105600 +/− 3700 |
| 20 | 93021 +/− 2800 |

RCA Testing of Virus Produced in SL0003 Cells

To test for RCA generation during production of rAd vectors, rAd-β-gal was serially-passaged in either SL0003 cells or 293 cells grown in cell factories containing approximately 1×10e9 cells, using a RCA-free virus lot as the initial inoculum. The bioassay used for detection of RCA had a sensitivity level of 1 particle of wild-type virus per 1.7×10e10 particles of rAd-β-gal (see above). After five serial passages, RCA was detected in rAd-β-gal virus purified from 293 cells, but no RCA was detected in rAd-β-gal purified from SL0003 cells. PCR analysis confirmed that the virus detected in the RCA assay from the 293 cells arose from recombination rather than contamination by Ad5.

III. Discussion

As exemplified herein, a human cell line (designated "SL0003") was created which incorporates separate expression cassettes, the first expression cassette containing an adenoviral E1A gene comprising the dl01/07 deletions and a second expression cassette containing the adenoviral E1B-55K gene which provides selected viral and cellular functions to complement adenovirus replication in A549 tumor cells. Optimization of E1 complementation in SL0003 cell line was achieved using sequential addition of separate E1A and E1B expression cassettes. In the SL0003 cell line, the E1Adl01/07 mutant gene was constitutively expressed to provide E1A function and to reduce cellular toxicity associated with wild-type E1A. E1B function in the SL0003 cell line was provided by constitutive expression of the E1B-55K gene; the E1B-19K gene was not included. Separation of the E1A and E1B cassettes, use of a mutant E1A gene, and only the E1B-55K gene eliminated the possibility of reconstitution of an intact E1 region through either homologous or non-homologous recombination and subsequent generation of RCA. Although the adenovirus sequences used for complementation in the SL0003 cell line are extensively modified compared to the wild-type E1 adenovirus sequence in 293 cells, the SL0003 cell line was shown to produce rAd vectors at viral production levels comparable to those obtained from the 293 cell line and without generation of detectable RCA.

Example 2

Generation an E1A, E1b and E2b Complementing Cell Line and Use of the Cell Line in the Production of Recombinant Adenovirus This example demonstrates the utility of an E1A, E1b and E2b complementing cell line for the production of high titers of replication-defective, helper-independent recombinant viruses.

I. Materials & Methods
Tissue Culture

A549, CHO-K1, Saos2, HeLa, and HepG2 cells were all purchased from ATCC. C7 cells (Amalfitano et al. (1996) PNAS 93:3352-3356) were kindly provided by J. Chamberlain, U. of Michigan. Human Tenon's capsule ocular fibroblast cells (designated as HOF cells) were isolated as described in Perkins et al ((2002) Arch. Ophthalmol. 120: 941-9). The development of Clone 4 cells are described above in Example 1; the clone is designated clone E1A01/07-4i. A549, C7, and HepG2 cells were maintained in Dulbecco's modified Eagle's medium (DME) supplemented with 10% fetal bovine serum (FBS). HeLa cells were maintained in Eagle's minimal essential media (MEM) supplemented with 5% FBS. CHO-K1 and Saos2 cells were maintained in Hams F12/DME media supplemented with 10% FBS. HOF cells were maintained in DME+20% FBS. Clone 4 cells were maintained in DME+10% FBS supplemented with 350 ug/ml of G418 (Geneticin, Invitrogen).

Isolation of Ad E2b Pol Expressing Cells

Clone 4 cells were transfected with 10 µg of linearized plasmid pMGCMVE2bPol using CaPO4 transfection (Sambrook et al. *Molecular Cloning: A Laboratory Manual* (1998) Cold Spring Harbor Laboratory Press, Plainview, N.Y.). Following transfection, the cells were selected in DME+10% serum supplemented with 150 µg/ml of hygromycin. The pool underwent limiting dilution cloning under drug selection and clone 3D8 was chosen. Clone 3D8 was grown in DME+10% serum supplemented with 150 µg/ml of hygromycin and 350 ug/ml G418.

Isolation of Ad E1b Expressing Cells

15M15 cells were derived from clone 3D8 described above. 3D8 cells were transfected with 10 µg linearized pVITRO2IRESPuroE1b (FIG. 4) using CaPO$_4$ transfection as before. Clone 15 was originally isolated from transfected pools treated with 0.2 µg/ml puromycin. Clone15M15 was further isolated from clone 15 through limiting dilution isolation and propagated in DME+10% FBS supplemented with 350 µg/ml of G418, 150 µg/ml of hygromycin, and 0.2 µg/ml of puromycin.

Plasmid Constructs Expressing Adenovirus Functions

Adenovirus E2b polymerase sequence was isolated from the plasmid PACN (Wills et al. (1995) Can. Gene Ther. 2:191-197) by PCR utilizing primers to add the first three upstream amino acids 'MAL', as described by Shu et al. (1988) Virol. 165:348-356, to the rest of the Ad 5 E2b polymerase coding sequence. The primers also added restriction sites allowing the PCR fragment to be cloned into the vector pMG (Invivo-Gen, San Diego, Calif.) downstream of the CMV promoter into the Bam HI restriction site. The resulting plasmid was named pMGCMVE2 Bpol (FIG. 5). The CMV driven full-length E2b polymerase coding sequence was followed by an IRES sequence and the hygromycin resistance gene which was used for selection.

The plasmid pIRESPuro2 (from Clontech, Palo Alto, Calif.) was digested with NdeI and BstBI, and the 4.7 kb fragment containing the ampicillin and puromycin resistance genes were isolated from a 1% TAE agarose gel following the protocol from the QIAEX II gel extraction kit from Qiagen (Valencia, Calif.). The plasmid pVITRO2 (from InvivoGen, San Diego, Calif.) was digested with NdeI and AccI, and the 3.9 kb fragment containing the human ferritin light and heavy subunit promoters with enhancers was isolated from a 1% TAE agarose gel as above. The two fragments were ligated together to form the plasmid pVITRO2IRESPuro. Adenovirus E1b sequence was isolated from the adenoviral plasmid pTG4609 (Transgene, FR) by PCR and subcloned into the plasmid pCR-Blunt II TOPO (Invitrogen, Carlsbad, Calif.) cloning vector. From there, the E1b fragment was digested out with EcoRI and BamHI and treated with Klenow and blunt end cloned into EcoRV digested pVITRO2IRESPuro. This created the plasmid pVITRO2IRESPuroE1b which had the E1b region driven by the human ferritin heavy subunit promoter and SV40 enhancer with a puromycin resistance gene for cell selection. The correct orientation of the E1b sequence was verified through restriction digestion patterns.

Viral Constructs

The construction of GFCB has been described previously (Cheney et al, (1998) Can. Res. 58: 2331-2334). Briefly, it is an E1, pIX, E3 deleted virus expressing the enhanced green fluorescent protein (eGFP, Clontech, Palo Alto, Calif.) from the human cytomegalovirus immediate-early promoter/enhancer and Ad 2 TPL cDNA from the E1 deleted region, utilizing the E1b/pIX viral polyA signal to terminate its message. CONG has also been described previously. It contains a consensus p53 response element driving eGFP in the 3' to 5' orientation in the deleted E3 region of an E1/E3 deleted viral backbone similar to GFCB. The viral constructs CGAB, 42GC, 46GC, and 2GCP all utilize the same expression cassette isolated from the plasmid pEGFP-N1 (Clontech, Palo Alto, Calif.). The cassette contains the human CMV immediate-early promoter/enhancer, the enhanced green fluorescent protein gene, and the SV40 early mRNA polyadenylation signal. For CGAB, this expression cassette replaces that contained in GFCB. 42GC, 46GC and 2GCP all contain their expression cassettes in the 5' to 3' orientation in the E3 deleted region of the viral backbone. 42GC and 2GCP are also E1a and E1b deleted, with pIX remaining intact. 46GC is an E1 intact virus and is replication competent. The 2GCP virus also has approximate 600 bp deletion in the E2b viral DNA polymerase region as reported in Amalfitano et al. (1998) ((1996) PNAS 93: 3352-3356) rendering it replication incompetent in the absence of exogenous E2b polymerase protein.

Western

To determine E2b polymerase expression levels, clones 3C4, 3C9, 3D8, and parental clone 4 and A549 cells were seeded in 10 cm dishes. The cells were incubated and allowed to grow for 2 days and then harvested. Equal protein, as determined by Bradford assay (Bio-Rad cat# 500-0006), was loaded onto a 4-12% NuPAGE Bis-Tris gel (Invitrogen, Carlsbad, Calif.). The protein was transferred and the filter was blocked, then incubated with a 1:2,000 dilution of rabbit anti E2b polymerase polyclonal antibody (provided by Dr Padmanabhan, U. Kansas), followed by a 1:2,000 dilution of goat anti-rabbit IgG-HRP (Jackson ImmunoResearch, West Grove, Pa.). The filters were developed with SuperSignal West Pico Chemiluminescent kit (Pierce, Rockford, Ill.) and exposed to film. The filters were then stripped and re-probed with β-actin (Sigma, St. Louis, Mo.) at a 1:10,000 dilution, followed by sheep anti-mouse IgG-HRP (Amersham Biosciences, Piscataway, N.J.) at a 1:2,000 dilution.

In determining adenovirus late gene protein expression, CHO, HELA, HepG2, and 15M15 cells were seeded in 6 well plates and infected the following day with $5 \times 10^8$ P/ml of CGAB, 42GC, 2GCP, 46GC or GFCB virus. The cells were harvested 4 days post transduction, and total protein content was determined by Bradford assay. Equal total protein was loaded onto 4-12% NuPAGE Bis-Tris gel and transferred onto PVDF filters (Millipore Corp, Bedford, Mass.). The filters were incubated with rabbit anti sera to Adenovirus type 5 (Access Biomedical, San Diego, Calif.) at a 1:2,500 dilution, followed by a 1:2,000 dilution of goat anti-rabbit IgG-HRP. The filters were then processed as described above.

Virus Productivity

To evaluate the viral productivity in the engineered cells, selected clones were seeded in 10 cm dishes and infected with $5 \times 10^8$ p/ml of 2GCP virus. An additional control plate was seeded for counting at the time of infection. Infected cells were harvested 3-4 days post infection when the majority of cells had rounded up and lifted off the plate, indicating viral replication had occurred. Virus was released from the cellular lysates by 3 cycles of freeze/thawing and removal of cellular debris by centrifugation. Virus was then purified and quantitated by column chromatography as described previously (Shabram et al. (1997) Hum. Gene Ther. 8: 453-465).

Productivity was determined by dividing the total virus particles by the number of cells at the time of infection, giving the virus particle per cell ratio as a measure of productivity of the cells in complementing virus growth.

Cytofluor/Transgene Expression

Cells were seeded in 6 well plates and returned to their incubators until they had reached 80-90% confluency. They were then infected with $5 \times 10^8$ P/ml of viruses in triplicate in a total volume of 3 ml per well. Cells were measured for GFP transgene expression using the CytoFluor Series 4000 Multi-well plate reader (PerSeptive Biosystems) and photographed using a Hammamatsu 3CCD analog camera and controller. GFP fluorescence is plotted as the average of relative Cytofluor values for the triplicate wells at each time point, minus background fluorescence, and +/−the standard deviation. Twice a week, 0.5 ml of fresh media was added per well for all cells.

E1b Complementation

Clones to be analyzed for E1b expression were seeded in 6 well plates and allowed to incubate and grow until they had reached approximately 80-90% confluency. At this point, the cells were infected with $5 \times 10^8$ P/ml of either GFCB or CONG virus in triplicate. Infected cells were then photographed using a Hammamatsu 3CCD analog camera and controller and assayed for GFP fluorescence using the CytoFluor Series 4000 Multi-well plate reader (PerSeptive Biosystems) set at 450 nm excitation and 508 nm emission at 48 hours post-infection. Average values from the duplicate wells+/−standard deviation were plotted as the ratio of CONG fluorescence over the GFCB derived fluorescent values.

II. Results

Addition of E2b Polymerase to E1a Complementing Cells

Figure 7A:
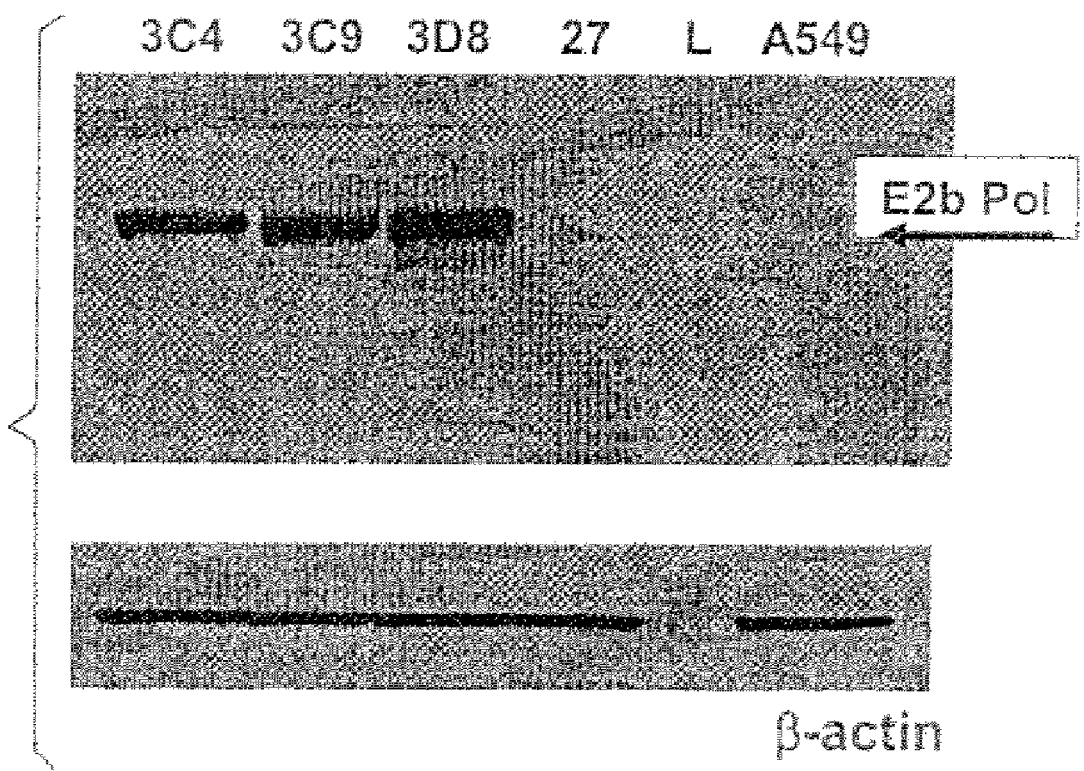
Figure 7B:
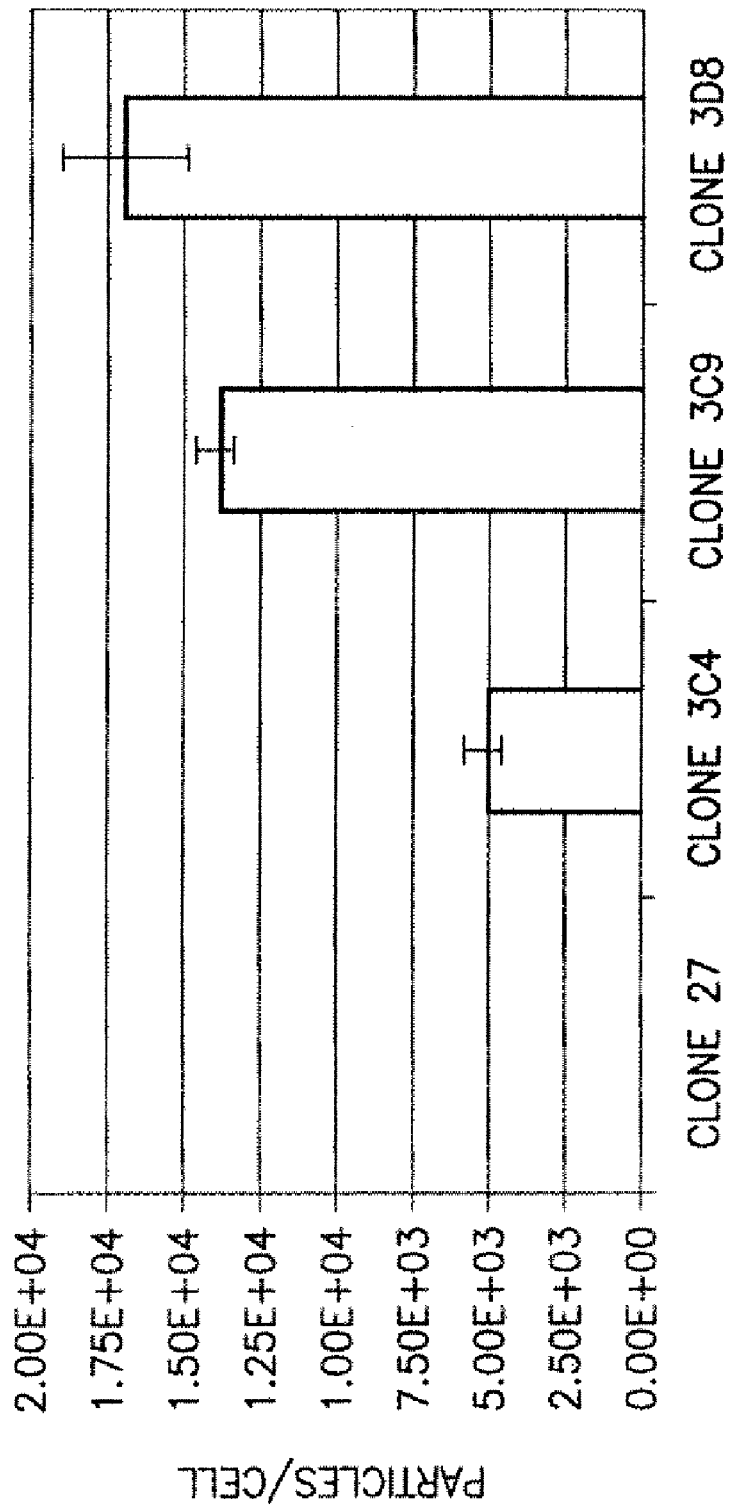

Following transfection of clone 4 cells with the E2b polymerase expressing plasmid pMGCMVE2bPol, resistant cells were selected by treatment with hygromycin and isolated as individual clones by limiting dilution purification. Western analysis of cellular lysates was used to select clones specifically expressing the 140 kd band representing E2b polymerase. In FIG. 7A, the clones 3C4, 3C9, and 3D8 all show the expected band for E2b Pol. This band is not present in the parental clone #4, or in A549 cells upon which all clones were based. All lanes were loaded at equal total protein concentrations as determined by Bradford assay and verified by β-actin detection. Since equal total protein was loaded per lane, the density of the polymerase band should reflect its level of expression in that particular clone. When compared to the ability of the particular clones to produce the polymerase deleted virus 2GCP, there is a positive correlation between the amount of polymerase expressed and the productivity of the clone (FIG. 7B). Since clone 4 was not engineered to express E2b polymerase, it is not able to support the growth of a polymerase deleted virus and no virus was recovered. Clone 3D8 expressed the highest amount of polymerase protein and also produced the most virus particles per cell. This clone was chosen for further analysis and was used as the parental line for introducing and expressing adenovirus E1b proteins.

Addition of E1b to 3D8

Figure 8A:
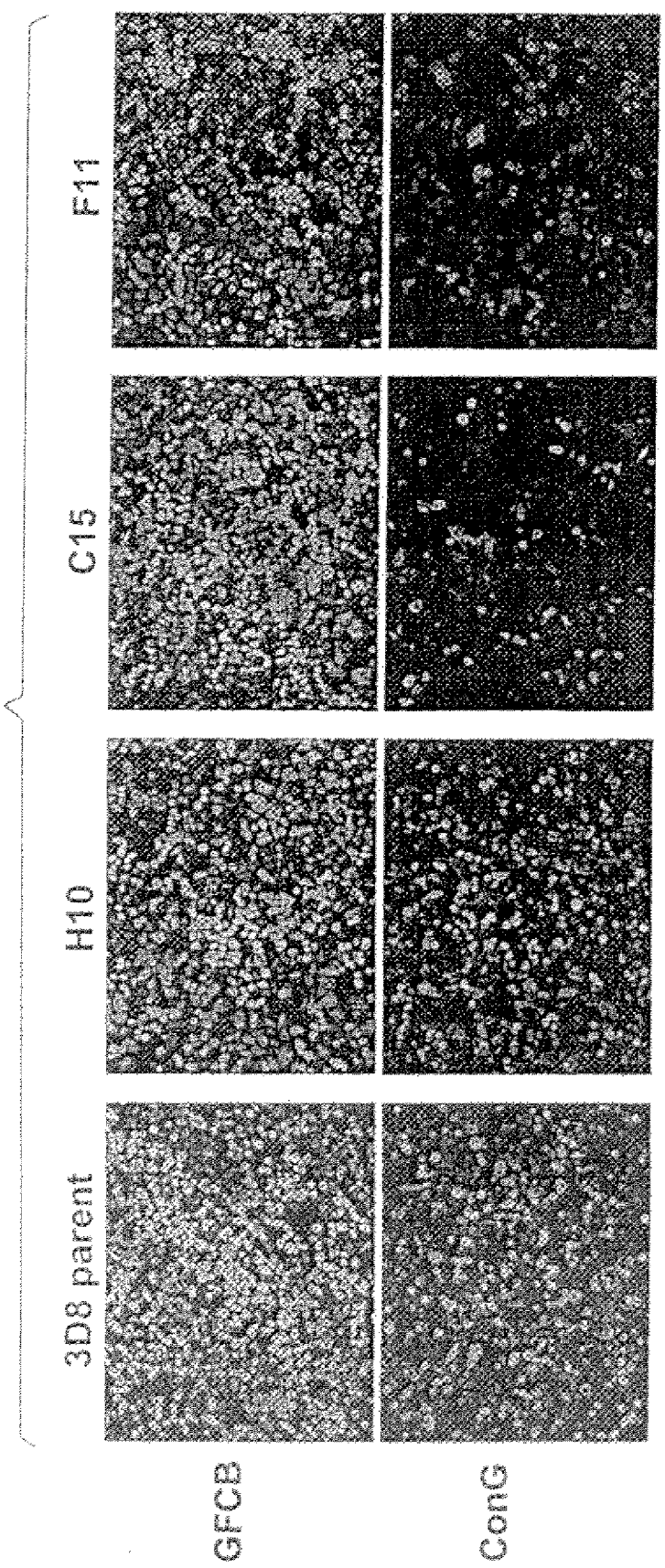
Figure 8B:
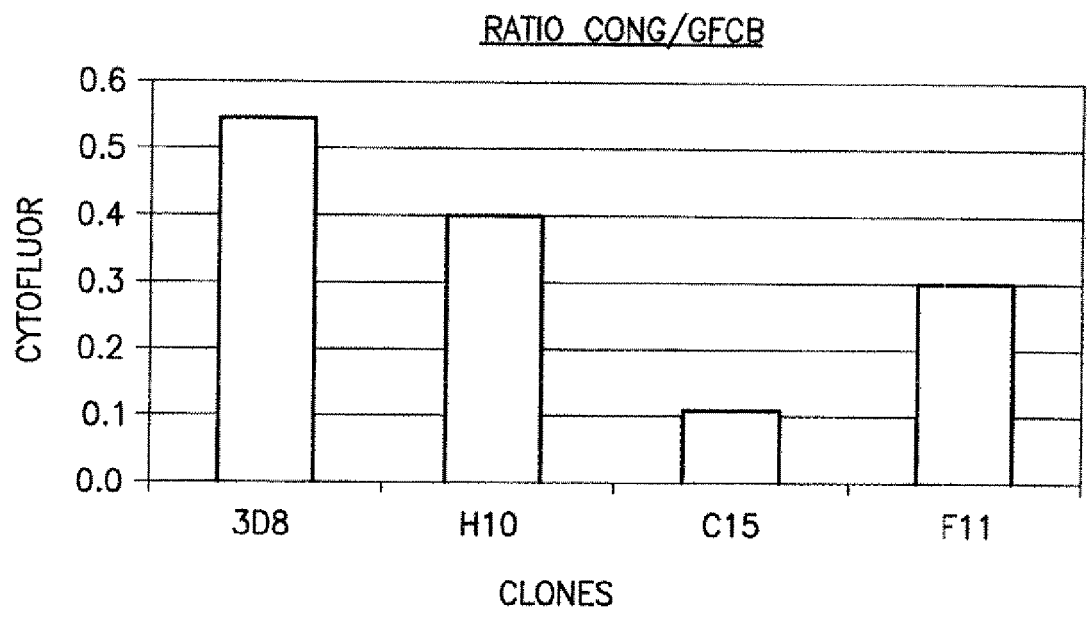
Figure 8C:
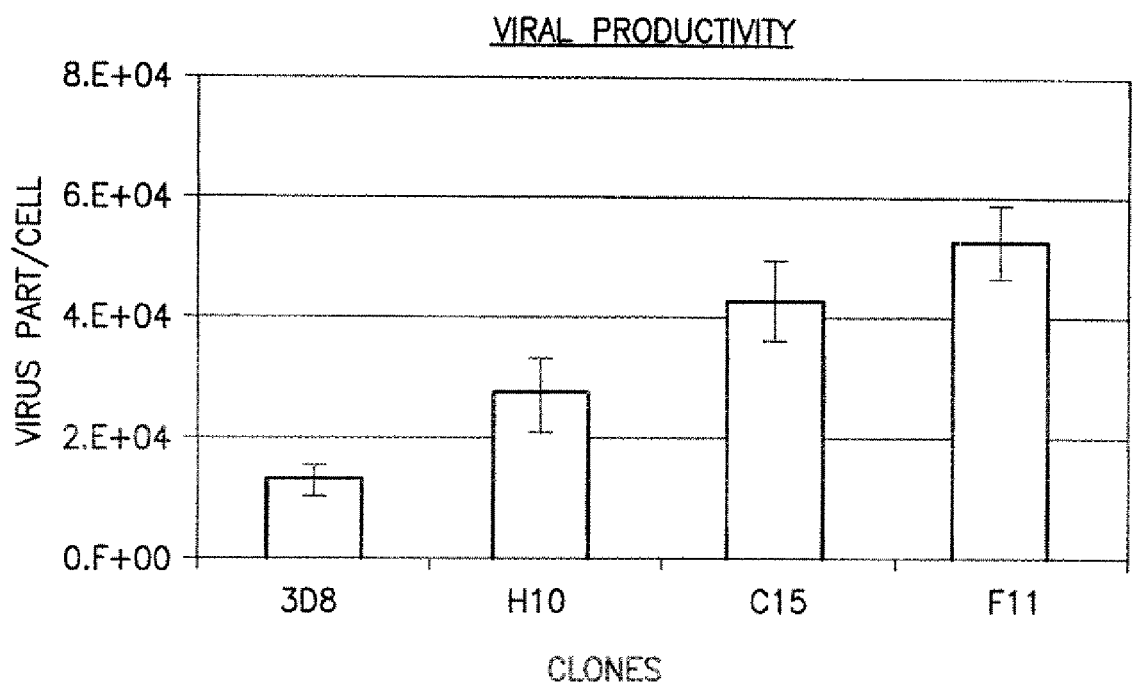

Clone 3D8 was transfected with the E1b encoding plasmid pVITRO2IRESPuroE1b, and individual clones resistant to puromycin treatment were selected and isolated as before. A functional assay was used to detect E1b function during the isolation process using the viruses CONG and GFCB. Clones isolated by limiting dilution which had been expanded to duplicate 6 well plates and were infected with $5 \times 10e8$ P/ml of CONG or GFCB virus. Forty eight hours later, GFP expression from the infected clones was measured by Cytofluor analysis. Infection with GFCB is used to control for potentially differing infectability of clones to adenovirus and so that a ratio of E1b mediated decrease in GFP fluorescence can be established. CONG is a virus using a p53 consensus sequence response element (p53RE) to drive GFP expression. The clones are based on A549 cells, which are positive for p53 expression. Therefore, infection of A549 based clones such as 3D8 will lead to p53 mediated expression of GFP. Adenovirus E1b 55 kd protein is known to bind p53 and convert it from a transcriptional activator to a transcriptional repressor (Yew and Berk (1992) Nature 357:82-85, Roth and Dobbelstein (2003) Methods Mol. Biol. 234:135-149). Clones expressing E1b 55 should then bind up p53 and prevent or reduce GFP fluorescence from CONG infected cells. Although the p53RE driving GFP expression is a weaker promoter than the CMV utilized in GFCB, clones expressing E1b proteins should lead to a further decrease in GFP expression from CONG dependent on the amount of E1b 55 expressed. In FIG. 8A, parental cell line 3D8 and three clones infected with either GFCB or CONG virus were photographed and their GFP fluorescence levels were quantitated using Cytofluor analysis. In FIG. 8B, the ratio of GFP fluorescence from CONG to GFCB was plotted. The change in values represents the varying degrees of decrease in GFP expression from CONG infections relative to the parental 3D8 clone due to differences in expression of E1b 55 kd from the cells. Clone 15 showed the greatest differential, suggesting that it should be expressing the greatest amount of E1b protein. It was shown above that the addition of E1b 55 to A549 based clones already expressing E1a function leads to an increased productivity of virus growth in the cells. When the clones in FIG. 8 were tested for productivity in the growth of 2GCP virus, an inverse correlation was found between the degree of GFP expression and productivity (FIG. 8C). Clones which showed the greatest decrease in GFP expression, which should result from greater expression of the E1b 55 protein, had the greatest increase in productivity compared to the non-E1b expressing parental clone 3D8 (FIG. 8C). Based on these results, clone C15 was chosen for further study.

Final Clone Analysis 15M15

Figure 9A:
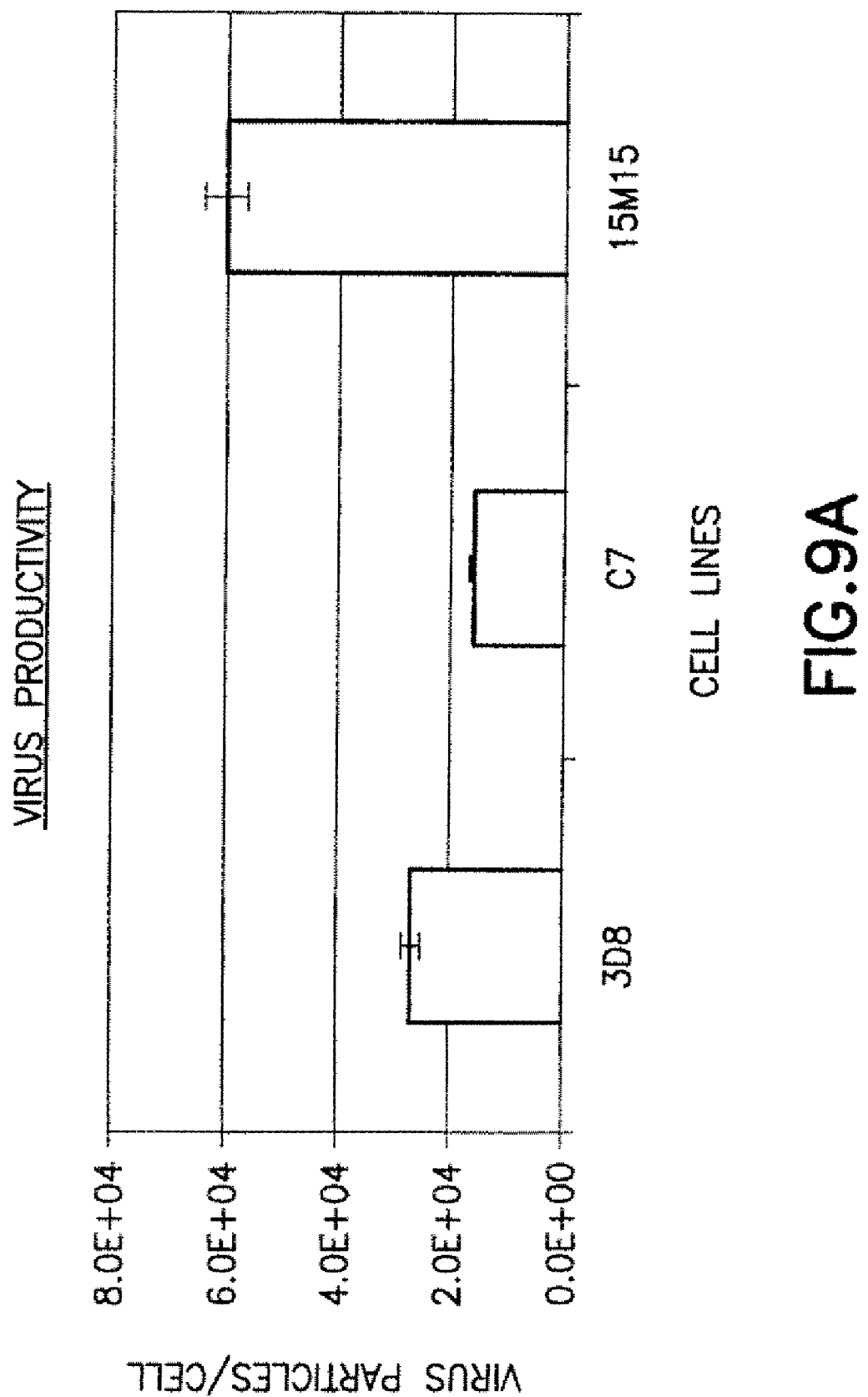
Figure 9C:
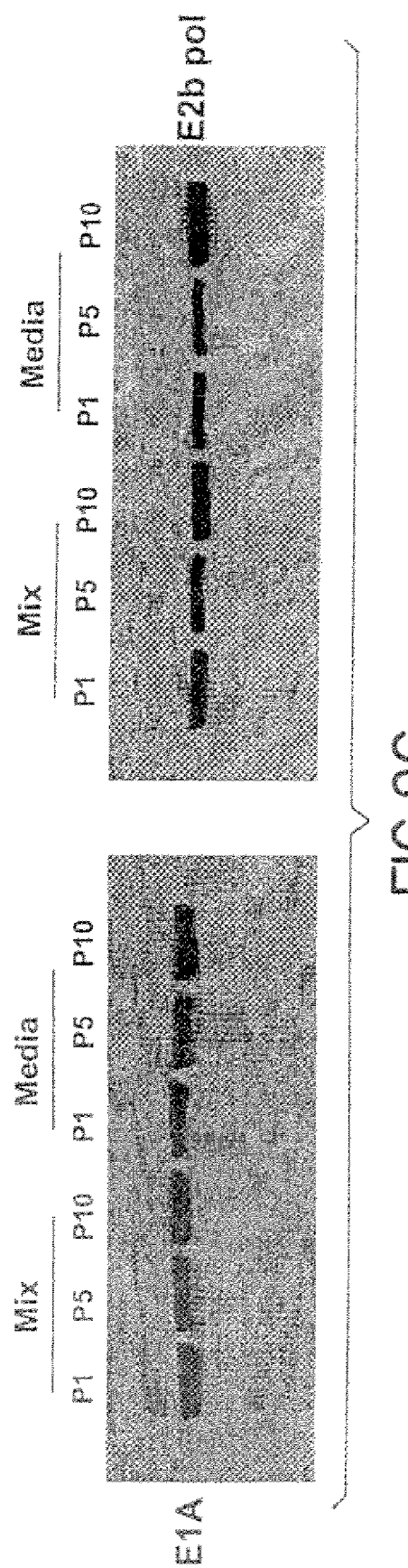

Clone 15 underwent further purification through sub-cloning in a combination selection media of G418, hygromycin, and puromycin. This combination should select for retention of E1a, E1b and E2b function. Further screening of isolated clones by productivity assays with 2GCP virus led to the selection of 15M15 as the final choice for the new complementing cell line. In FIG. 9A shows the productivity of clone 15M15 for 2GCP growth compared to its parental clone 3D8, as well as to C7 cells. C7 cells are based on the Ad E1 complementing 293 cells which have been further engineered to also express E2b polymerase (Amalfitano et al. (1996) PNAS 93:3352-3356). The 15M15 cell line is able to propagate the polymerase deleted virus 2GCP to a higher extent than its 293 based counterpart (C7) or its E1b lacking parental cell line 3D8. The genomic stability of the new line was tested by serial passage and infection of the cells either in their complete selection media mix or just media alone. FIG. 9B shows the results of viral productivity under each condition at passages 1, 5, and 10 for cells infected with 2 different doses of 2GCP virus. The clone's ability to complement the adenovirus functions necessary to propagate polymerase deleted virus to high yields appears very stable through 10 passages, even without selection drugs in the media. Western analysis was used to detect the E1a and E2b polymerase proteins from cells isolated at passages 1, 5, and 10. As shown in FIG. 9C, both proteins also appeared to be stable over 10 passages, even in the absence of selection media.

Viral Constructs

FIG. 6 shows a schematic for the viruses used in this study. The E3 and E1 deletions indicated are the same for all but two of the viruses. For control virus GFCB, the E1 deletion extends an additional 700 base pairs into the pIX coding sequence, allowing the E1b/pIX viral polyA signal to be used for the GFP expression cassette. Virus 46GC is E1 wild-type and replication competent. The CMV-GFP-pA expression cassette is identical for the CGAB, 42GC, 2GCP and 46GC viruses as verified by restriction analysis, PCR, and sequencing. In the CONG virus, the CMV promoter in the expression cassette is replaced by a p53 consensus response element to drive the GFP gene. The E2b polymerase deletion in 2GCP restricts its growth to cell lines expressing E2b polymerase. 2GCP was originally isolated in the E2b polymerase expressing cell line C7.

Decreased Late Ad Gene Expression

Infected cell lysates were analyzed for adenovirus protein expression by Western analysis using polyclonal antibody against Ad 5. The complementing producer cell line 15M15 was infected with GFCB, CGAB, 42GC, and 2GCP. All 4 viruses are able to replicate well in this cell line and all show expected viral bands (FIG. 10A).

CHO cells were infected with CGAB, 42GC, 2GCP and 46GC virus. As shown in FIG. 10B, only the replication competent 46GC virus showed any viral bands corresponding to hexon and fiber in this non-complementing cell line.

HeLa and HepG2 cells were infected with CGAB, 42GC, 2GCP and 46GC virus. HepG2 cells were also infected with GFCB virus. HeLa cells are able to partially complement E1a function due to the expression of the E7 gene from integrated human papillomavirus (Schneider-Gadicke and Schwarz (1986) EMBO 5:2285-2292, Phelps et al. (1988) Cell 53:539-547), while HepG2 cells have been reported to have high NFIL-6 responsive activity, which can functionally substitute for E1a in activation of other adenovirus promoters (Spergel and Chen-Kiang (1991) PNAS 88:6472-6476). In both cell lines, there is a greatly reduced or absent expression of viral proteins observed with the polymerase deleted 2GCP virus compared to the other E1/E3 deleted but polymerase intact viruses (FIGS. 10C and 10D). These results are in agreement with the findings of others using viruses deleted for essential replication functions (refs, E2b pol, pTp, DBP). A decrease in the ability of a virus to express its own proteins in infected cells is the basis for reducing the immune mediated clearance of infected cells and prolonging transgene expression (Yang et al., (1994) PNAS 91: 4407-4411; Gilgenkrantz et al., (1995) Hum. Gene Ther. 6: 1265-1274; Yang et al., (1995) J. Immunol. 155: 2564-2570). The replication competent 46GC virus shows the highest levels of viral proteins as expected.

Improved Transgene Expression

In comparing GFP fluorescence in vitro, despite having identical expression cassettes, there was a consistent ranking of constructs. GFP fluorescence was consistently greatest with 2GCP, followed by 42GC, and then CGAB. This was found in multiple cell types, including CHO, Saos 2, and human ocular fibroblasts (HOF) cells as shown in FIG. 11. Cytofluor values are plotted as the average from triplicate infections +/− their standard deviation, along with representative pictures of the cells infected with the indicated constructs for HOF and Saos 2 cells in FIG. 11A-D and for CHO cells in FIG. 11 E-F. The high levels of in vitro expression from the new constructs persisted over extended periods of time.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A recombinant adenovirus production cell line, designated SL0003, deposited with the American Type Culture Collection (ATCC) under accession number PTA-6231.

2. A recombinant adenovirus production cell line, designated SL0006, deposited with the American Type Culture Collection (ATCC) under accession number PTA-6663.

* * * * *

UNITED STATES PATENT AND TRADEMARK OFFICE
CERTIFICATE OF CORRECTION

PATENT NO. : 7,851,218 B2
APPLICATION NO. : 11/301309
DATED : December 14, 2010
INVENTOR(S) : John A. Howe et al.

Page 1 of 1

It is certified that error appears in the above-identified patent and that said Letters Patent is hereby corrected as shown below:

On the Title page, Item [73] Assignee should read:

CANJI, Inc., Palo Alto, CA

Signed and Sealed this
Twenty-ninth Day of May, 2012

David J. Kappos
*Director of the United States Patent and Trademark Office*

SEQUENCE LISTING

<160> NUMBER OF SEQ ID NOS: 27

<210> SEQ ID NO 1
<211> LENGTH: 6074
<212> TYPE: DNA
<213> ORGANISM: Artificial Sequence
<220> FEATURE:
<223> OTHER INFORMATION: plasmid pRcRSV-E1Adl01/07

<400> SEQUENCE: 1

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgtatctgag     240
gggactaggg tgtgtttagg cgaaaagcgg ggcttcggtt gtacgcggtt aggagtcccc     300
tcaggatata gtagtttcgc ttttgcatag ggaggggggaa atgtagtctt atgcaataca     360
cttgtagtct tgcaacatgg taacgatgag ttagcaacat gccttacaag gagagaaaaa     420
gcaccgtgca tgccgattgg tggaagtaag gtggtacgac cgtgccttat taggaaggca     480
acagacaggt ctgacatgga ttggacgaac cactgaattc cgcattgcag agataattgt     540
atttaagtgc ctagctcgat acaataaacg ccatttgacc attcaccaca ttggtgtgca     600
cctccaagct tggtaccgag ctcggatcca aaatgagaca tgaggtactg gctgataatc     660
ttccacctcc tagccatttt gaaccaccta cccttcacga actgtatgat ttagacgtga     720
cggcccccga agatcccaac gaggaggcgg tttcgcagat ttttcccgac tctgtaatgt     780
tggcggtgca ggaagggatt gacttactca cttttccgcc ggcgcccggt tctccggagc     840
cgcctcacct ttcccggcag cccgagcagc cggagcagag agccttgggt ccggtttgcc     900
acgaggctgg ctttccaccc agtgacgacg aggatgaaga gggtgaggag tttgtgttag     960
attatgtgga gcaccccggg cacggttgca ggtcttgtca ttatcaccgg aggaatacgg    1020
gggacccaga tattatgtgt tcgctttgct atatgaggac ctgtggcatg tttgtctaca    1080
gtaagtgaaa attatgggca gtgggtgata gagtggtggg tttggtgtgg taatttttt     1140
tttaattttt acagttttgt ggtttaaaga attttgtatt gtgatttttt taaaaggtcc    1200
tgtgtctgaa cctgagcctg agcccgagcc agaaccggag cctgcaagac ctacccgccg    1260
tcctaaaatg gcgcctgcta tcctgagacg cccgacatca cctgtgtcta gagaatgcaa    1320
tagtagtacg gatagctgtg actccggtcc ttctaacaca cctcctgaga tacacccggt    1380
ggtcccgctg tgccccatta aaccagttgc cgtgagagtt ggtgggcgtc gccaggctgt    1440
ggaatgtatc gaggacttgc ttaacgagcc tgggcaacct ttggacttga gctgtaaacg    1500
ccccaggcca taaggtgtaa acctgtgatt gcggccgctc gagcatgcat ctagagctcg    1560
ctgatcagcc tcgactgtgc cttcagttg ccagccatct gttgtttgcc ctcccccgt     1620
gccttccttg accctggaag gtgccactcc cactgtcctt tcctaataaa atgaggaaat    1680
tgcatcgcat tgtctgagta ggtgtcattc tattctgggg ggtggggtgg ggcaggacag    1740
caagggggag gattgggaag acaatagcag gcatgctggg gatgcggtgg gctctatggc    1800
ttctgaggcg gaaagaacca gctgggctc gaggggggat ccccacgcgc cctgtagcgg    1860
cgcattaagc gcggcgggtg tggtggttac gcgcagcgtg accgctacac ttgccagcgc    1920
cctagcgccc gctcctttcg ctttcttccc ttcctttctc gccacgttcg ccggctttcc    1980
ccgtcaagct ctaaatcggg gcatcccttt agggttccga tttagtgctt tacggcacct    2040
cgaccccaaa aaacttgatt agggtgatgg ttcacgtagt gggccatcgc cctgatagac    2100
ggttttcgc cctttgacgt tggagtccac gttctttaat agtggactct gttccaaac      2160
tggaacaaca ctcaaccta tctcggtcta ttcttttgat ttataaggga ttttggggat     2220
ttcggcctat tggttaaaaa atgagctgat ttaacaaaaa tttaacgcga attttaacaa    2280
```

-continued

```
aatattaacg tttacaattt aaatatttgc ttatacaatc ttcctgtttt tggggctttt    2340
ctgattatca accggggtgg gtaccgagct cgaattctgt ggaatgtgtg tcagttaggg    2400
tgtggaaagt ccccaggctc cccaggcagg cagaagtatg caaagcatgc atctcaatta    2460
gtcagcaacc aggtgtggaa agtccccagg ctccccagca ggcagaagta tgcaaagcat    2520
gcatctcaat tagtcagcaa ccatagtccc gcccctaact ccgcccatcc cgcccctaac    2580
tccgcccagt tccgcccatt ctccgcccca tggctgacta atttttttta tttatgcaga    2640
ggccgaggcc gcctcggcct ctgagctatt ccagaagtag tgaggaggct ttttggagg    2700 cctaggcttt tgcaaaaagc tcccgggagc ttggatatcc attttcggat ctgatcaaga    2760
gacaggatga ggatcgtttc gcatgattga acaagatgga ttgcacgcag gttctccggc    2820
cgcttgggtg gagaggctat tcggctatga ctgggcacaa cagacaatcg gctgctctga    2880
tgccgccgtg ttccggctgt cagcgcaggg gcgcccggtt cttttgtca agaccgacct    2940 gtccggtgcc ctgaatgaac tgcaggacga ggcagcgcgg ctatcgtggc tggccacgac    3000
gggcgttcct tgcgcagctg tgctcgacgt tgtcactgaa gcgggaaggg actggctgct    3060
attgggcgaa gtgccggggc aggatctcct gtcatctcac cttgctcctg ccagaaagt    3120 atccatcatg gctgatgcaa tgcggcggct gcatacgctt gatccggcta cctgcccatt    3180
cgaccaccaa gcgaaacatc gcatcgacg agcacgtact cggatggaag ccggtcttgt    3240
cgatcaggat gatctggacg aagagcatca ggggctcgcg ccagccgaac tgttcgccag    3300
gctcaaggcg cgcatgcccg acggcgagga tctcgtcgtg acccatggcg atgcctgctt    3360
gccgaatatc atggtggaaa atggccgctt ttctggattc atcgactgtg gccggctggg    3420
tgtggcggac cgctatcagg acatagcgtt ggctacccgt gatattgctg aagagcttgg    3480
cggcgaatgg gctgaccgct tcctcgtgct ttacggtatc gccgctcccg attcgcagcg    3540
catcgccttc tatcgccttc ttgacgagtt cttctgagcg ggactctggg gttcgaaatg    3600
accgaccaag cgacgcccaa cctgccatca cgagatttcg attccaccgc cgccttctat    3660
gaaaggttgg gcttcggaat cgttttccgg gacgccggct ggatgatcct ccagcgcggg    3720
gatctcatgc tggagttctt cgcccacccc aacttgttta ttgcagctta taatggttac    3780
aaataaagca atagcatcac aaatttcaca aataaagcat ttttttcact gcattctagt    3840
tgtggtttgt ccaaactcat caatgtatct tatcatgtct ggatcccgtc gacctcgaga    3900
gcttggcgta atcatggtca tagctgtttc ctgtgtgaaa ttgttatccg ctcacaattc    3960
cacacaacat acgagccgga agcataaagt gtaaagcctg gggtgcctaa tgagtgagct    4020
aactcacatt aattgcgttg cgctcactgc ccgctttcca gtcgggaaac ctgtcgtgcc    4080
agctgcatta atgaatcggc caacgcgcgg ggagaggcgg tttgcgtatt gggcgctctt    4140
ccgcttcctc gctcactgac tcgctgcgct cggtcgttcg gctgcggcga gcggtatcag    4200
ctcactcaaa ggcggtaata cggttatcca cagaatcagg ggataacgca ggaaagaaca    4260
tgtgagcaaa aggccagcaa aaggccagga accgtaaaaa ggccgcgttg ctggcgtttt    4320
tccataggct ccgcccccct gacgagcatc acaaaaatcg acgctcaagt cagaggtggc    4380
gaaacccgac aggactataa agataccagg cgtttccccc tggaagctcc ctcgtgcgct    4440
ctcctgttcc gaccctgccg cttaccggat acctgtccgc ctttctccct tcgggaagcg    4500
tggcgctttc tcaatgctca cgctgtaggt atctcagttc ggtgtaggtc gttcgctcca    4560
agctgggctg tgtgcacgaa ccccccgttc agcccgaccg ctgcgcctta tccggtaact    4620
atcgtcttga gtccaacccg gtaagacacg acttatcgcc actggcagca gccactggta    4680
```

```
acaggattag cagagcgagg tatgtaggcg gtgctacaga gttcttgaag tggtggccta    4740
actacggcta cactagaagg acagtatttg gtatctgcgc tctgctgaag ccagttacct    4800
tcggaaaaag agttggtagc tcttgatccg gcaaacaaac caccgctggt agcggtggtt    4860 ttttttgtttg caagcagcag attacgcgca gaaaaaagg atctcaagaa gatcctttga    4920
tcttttctac ggggtctgac gctcagtgga acgaaaactc acgttaaggg attttggtca    4980
tgagattatc aaaaggatc ttcacctaga tccttttaaa ttaaaaatga agttttaaat    5040
caatctaaag tatatatgag taaacttggt ctgacagtta ccaatgctta atcagtgagg    5100
cacctatctc agcgatctgt ctatttcgtt catccatagt tgcctgactc ccgtcgtgt    5160 agataactac gatacgggag ggcttaccat ctggccccag tgctgcaatg ataccgcgag    5220
acccacgctc accggctcca gatttatcag caataaacca gccagccgga agggccgagc    5280
gcagaagtgg tcctgcaact ttatccgcct ccatccagtc tattaattgt tgccgggaag    5340
ctagagtaag tagttcgcca gttaatagtt tgcgcaacgt tgttgccatt gctacaggca    5400
tcgtggtgtc acgctcgtcg tttggtatgg cttcattcag ctccggttcc caacgatcaa    5460
ggcgagttac atgatccccc atgttgtgca aaaaagcggt tagctccttc ggtcctccga    5520
tcgttgtcag aagtaagttg gccgcagtgt tatcactcat ggttatggca gcactgcata    5580
attctcttac tgtcatgcca tccgtaagat gcttttctgt gactggtgag tactcaacca    5640
agtcattctg agaatagtgt atgcggcgac cgagttgctc ttgcccggcg tcaatacggg    5700
ataataccgc gccacatagc agaactttaa aagtgctcat cattggaaaa cgttcttcgg    5760
ggcgaaaact ctcaaggatc ttaccgctgt tgagatccag ttcgatgtaa cccactcgtg    5820
cacccaactg atcttcagca tcttttactt tcaccagcgt ttctgggtga gcaaaaacag    5880
gaaggcaaaa tgccgcaaaa aagggaataa gggcgacacg gaaatgttga atactcatac    5940
tcttcctttt tcaatattat tgaagcattt atcagggtta ttgtctcatg agcggataca    6000
tatttgaatg tatttagaaa aataaacaaa tagggggttcc gcgcacattt ccccgaaaag    6060
tgccacctga cgtc                                                      6074

<210> SEQ ID NO 2
<211> LENGTH: 7049
<212> TYPE: DNA
<213> ORGANISM: Artificial Sequence
<220> FEATURE:
<223> OTHER INFORMATION: plasmid pcDNA3.1(+)E1B 55K Hygro

<400> SEQUENCE: 2
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
```

```
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg       780
gtaggcgtgt acggtgggag gtctatataa gcagagctct ctggctaact agagaaccca     840
ctgcttactg gcttatcgaa attaatacga ctcactatag ggagacccaa gctggctagc      900
gtttaaactt aagcttggta ccgagctcgg atccaggaaa aatggagcga agaaacccat      960
ctgagcgggg ggtacctgct ggattttctg gccatgcatc tgtggagagc ggttgtgaga     1020
cacaagaatc gcctgctact gttgtcttcc gtccgcccgg cgataatacc gacggaggag     1080
cagcagcagc agcaggagga agccaggcgg cggcggcagg agcagagccc atggaacccg     1140
agagccggcc tggaccctcg ggaatgaatg ttgtacaggt ggctgaactg tatccagaac     1200
tgagacgcat tttgacaatt acagaggatg ggcaggggct aaaggggta aagagggagc      1260 ggggggcttg tgaggctaca gaggaggcta ggaatctagc ttttagctta atgaccagac     1320
accgtcctga gtgtattact tttcaacaga tcaaggataa ttgcgctaat gagcttgatc     1380
tgctggcgca gaagtattcc atagagcagc tgaccactta ctggctgcag ccaggggatg     1440
attttgagga ggctattagg gtatatgcaa aggtggcact taggccagat tgcaagtaca     1500
agatcagcaa acttgtaaat atcaggaatt gttgctacat ttctgggaac ggggccgagg     1560
tggagataga tacggaggat agggtggcct ttagatgtag catgataaat atgtggccgg     1620
gggtgcttgg catggacggg gtggttatta tgaatgtaag gtttactggc cccaattta      1680 gcggtacggt tttcctggcc aataccaacc ttatcctaca cggtgtaagc ttctatgggt     1740
ttaacaatac ctgtgtggaa gcctggaccg atgtaagggt tcggggctgt gccttttact     1800
gctgctggaa gggggtggtg tgtcgcccca aaagcagggc ttcaattaag aaatgcctct     1860
ttgaaaggtg taccttgggt atcctgtctg agggtaactc cagggtgcgc cacaatgtgg     1920
cctccgactg tggttgcttc atgctagtga aaagcgtggc tgtgattaag cataacatgg     1980
tatgtggcaa ctgcgaggac agggcctctc agatgctgac ctgctcggac ggcaactgtc     2040
acctgctgaa gaccattcac gtagccagcc actctcgcaa ggcctggcca gtgtttgagc     2100
ataacatact gacccgctgt tccttgcatt gggtaacag gaggggggtg ttcctacctt      2160
accaatgcaa tttgagtcac actaagatat tgcttgagcc cgagagcatg tccaaggtga     2220
acctgaacgg ggtgtttgac atgaccatga agatctggaa ggtgctgagg tacgatgaga     2280
cccgcaccag gtgcagaccc tgcgagtgtg gcggtaaaca tattaggaac cagcctgtga     2340
tgctggatgt gaccgaggag ctgaggcccg atcacttggt gctggcctgc acccgcgctg     2400
agtttggctc tagcgatgaa gatacagatt gactcgagtc tagagggccc gtttaaaccc     2460
gctgatcagc ctcgactgtg ccttctagtt gccagccatc tgttgtttgc ccctcccccg     2520
tgccttcctt gaccctggaa ggtgccactc ccactgtcct ttcctaataa aatgaggaaa     2580
ttgcatcgca ttgtctgagt aggtgtcatt ctattctggg gggtggggtg ggcaggaca      2640 gcaaggggga ggattgggaa gacaatagca ggcatgctgg gatgcggtg ggctctatgg      2700 cttctgaggc ggaaagaacc agctgggct ctaggggta tccccacgcg ccctgtagcg       2760
gcgcattaag cgcggcggt gtggtggtta cgcgcagcgt gaccgctaca cttgccagcg      2820
ccctagcgcc cgctcctttc gctttcttcc cttcctttct cgccacgttc gccggctttc     2880
cccgtcaagc tctaaatcgg ggcatccctt tagggttccg atttagtgct ttacggcacc     2940
tcgaccccaa aaaacttgat tagggtgatg gttcacgtag tgggccatcg ccctgataga     3000
```

```
cggttttttcg cccttttgacg ttggagtcca cgttctttaa tagtggactc ttgttccaaa    3060
ctggaacaac actcaaccct atctcggtct attcttttga tttataaggg attttgggga    3120
tttcggccta ttggttaaaa aatgagctga tttaacaaaa atttaacgcg aattaattct    3180
gtggaatgtg tgtcagttag ggtgtggaaa gtccccaggc tccccaggca ggcagaagta    3240
tgcaaagcat gcatctcaat tagtcagcaa ccaggtgtgg aaagtcccca ggctccccag    3300
caggcagaag tatgcaaagc atgcatctca attagtcagc aaccatagtc ccgcccctaa    3360
ctccgcccat cccgccccta actccgccca gttccgccca ttctccgccc catggctgac    3420
taattttttt tatttatgca gaggccgagg ccgcctctgc ctctgagcta ttccagaagt    3480
agtgaggagg cttttttgga ggcctaggct tttgcaaaaa gctcccggga gcttgtatat    3540 ccatttcgg atctgatcag cacgtgatga aaaagcctga actcaccgcg acgtctgtcg    3600
agaagtttct gatcgaaaag ttcgacagcg tctccgacct gatgcagctc tcggagggcg    3660
aagaatctcg tgctttcagc ttcgatgtag gagggcgtgg atatgtcctg cgggtaaata    3720
gctgcgccga tggtttctac aaagatcgtt atgtttatcg gcactttgca tcggccgcgc    3780
tcccgattcc ggaagtgctt gacattgggg aattcagcga gagcctgacc tattgcatct    3840
cccgccgtgc acagggtgtc acgttgcaag acctgcctga aaccgaactg cccgctgttc    3900
tgcagccggt cgcggaggcc atggatgcga tcgctgcggc cgatcttagc cagacgagcg    3960
ggttcggccc attcggaccg caaggaatcg gtcaatacac tacatggcgt gatttcatat    4020
gcgcgattgc tgatccccat gtgtatcact ggcaaactgt gatggacgac accgtcagtg    4080
cgtccgtcgc gcaggctctc gatgagctga tgctttgggc cgaggactgc cccgaagtcc    4140
ggcacctcgt gcacgcggat ttcggctcca acaatgtcct gacggacaat ggccgcataa    4200
cagcggtcat tgactggagc gaggcgatgt tcggggattc ccaatacgag gtcgccaaca    4260
tcttcttctg gaggccgtgg ttggcttgta tggagcagca gacgcgctac ttcgagcgga    4320
ggcatccgga gcttgcagga tcgccgcggc tccgggcgta tatgctccgc attggtcttg    4380
accaactcta tcagagcttg gttgacggca atttcgatga tgcagcttgg gcgcagggtc    4440
gatgcgacgc aatcgtccga tccggagccg ggactgtcgg gcgtacacaa atcgcccgca    4500
gaagcgcggc cgtctggacc gatggctgtg tagaagtact cgccgatagt ggaaaccgac    4560
gccccagcac tcgtccgagg gcaaaggaat agcacgtgct acgagatttc gattccaccg    4620
ccgccttcta tgaaaggttg gcttcggaa tcgtttttccg ggacgccggc tggatgatcc    4680
tccagcgcgg ggatctcatg ctggagttct tcgcccaccc caacttgttt attgcagctt    4740
ataatggtta caaataaagc aatagcatca caaatttcac aaataaagca tttttttcac    4800
tgcattctag ttgtggtttg tccaaactca tcaatgtatc ttatcatgtc tgtataccgt    4860
cgacctctag ctagagcttg gcgtaatcat ggtcatagct gtttcctgtg tgaaattgtt    4920
atccgctcac aattccacac aacatacgag ccggaagcat aaagtgtaaa gcctggggtg    4980
cctaatgagt gagctaactc acattaattg cgttgcgctc actgcccgct ttccagtcgg    5040
gaaacctgtc gtgccagctg cattaatgaa tcggccaacg cgcggggaga ggcggtttgc    5100
gtattgggcg ctcttccgct tcctcgctca ctgactcgct gcgctcggtc gttcggctgc    5160
ggcgagcggt atcagctcac tcaaaggcgg taatacggtt atccacagaa tcaggggata    5220
acgcaggaaa gaacatgtga gcaaaaggcc agcaaaaggc caggaaccgt aaaaaggccg    5280
cgttgctggc gtttttccat aggctccgcc cccctgacga gcatcacaaa aatcgacgct    5340
```

```
caagtcagag gtggcgaaac ccgacaggac tataaagata ccaggcgttt ccccctggaa    5400
gctccctcgt gcgctctcct gttccgaccc tgccgcttac cggatacctg tccgcctttc    5460
tcccttcggg aagcgtggcg ctttctcaat gctcacgctg taggtatctc agttcggtgt    5520
aggtcgttcg ctccaagctg gctgtgtgc acgaaccccc cgttcagccc gaccgctgcg     5580
ccttatccgg taactatcgt cttgagtcca acccggtaag acacgactta tcgccactgg    5640
cagcagccac tggtaacagg attagcagag cgaggtatgt aggcggtgct acagagttct    5700
tgaagtggtg gcctaactac ggctacacta aaggacagt atttggtatc tgcgctctgc     5760
tgaagccagt taccttcgga aaaagagttg gtagctcttg atccggcaaa caaccaccg     5820 ctggtagcgg tggttttttt gtttgcaagc agcagattac gcgcagaaaa aaggatctc     5880 aagaagatcc tttgatcttt tctacggggt ctgacgctca gtggaacgaa aactcacgtt    5940
aagggatttt ggtcatgaga ttatcaaaaa ggatcttcac ctagatcctt ttaaattaaa    6000
aatgaagttt taaatcaatc taagtatat atgagtaaac ttggtctgac agttaccaat     6060
gcttaatcag tgaggcacct atctcagcga tctgtctatt tcgttcatcc atagttgcct    6120
gactccccgt cgtgtagata actacgatac gggagggctt accatctggc cccagtgctg    6180
caatgatacc gcgagaccca cgctcaccgg ctccagattt atcagcaata aaccagccag    6240
ccggaagggc cgagcgcaga agtggtcctg caactttatc cgcctccatc cagtctatta    6300
attgttgccg ggaagctaga gtaagtagtt cgccagttaa tagtttgcgc aacgttgttg    6360
ccattgctac aggcatcgtg gtgtcacgct cgtcgtttgg tatggcttca ttcagctccg    6420
gttcccaacg atcaaggcga gttacatgat cccccatgtt gtgcaaaaaa gcggttagct    6480
ccttcggtcc tccgatcgtt gtcagaagta agttggccgc agtgttatca ctcatggtta    6540
tggcagcact gcataattct cttactgtca tgccatccgt aagatgcttt tctgtgactg    6600
gtgagtactc aaccaagtca ttctgagaat agtgtatgcg gcgaccgagt tgctcttgcc    6660
cggcgtcaat acgggataat accgcgccac atagcagaac tttaaaagtg ctcatcattg    6720
gaaaacgttc ttcggggcga aaactctcaa ggatcttacc gctgttgaga tccagttcga    6780
tgtaacccac tcgtgcaccc aactgatctt cagcatcttt tactttcacc agcgtttctg    6840
ggtgagcaaa aacaggaagg caaaatgccg caaaaaaggg aataagggcg acacggaaat    6900
gttgaatact catactcttc cttttccaat attattgaag catttatcag ggttattgtc    6960
tcatgagcgg atacatattt gaatgtattt agaaaaataa acaaataggg gttccgcgca    7020
catttccccg aaaagtgcca cctgacgtc                                       7049
```

<210> SEQ ID NO 3
<211> LENGTH: 870
<212> TYPE: DNA
<213> ORGANISM: Artificial Sequence
<220> FEATURE:
<223> OTHER INFORMATION: nucleotide sequence encoding human adenovirus
      type 5, 289R E1A, wild type

<400> SEQUENCE: 3

```
atgagacata ttatctgcca cggaggtgtt attaccgaag aaatggccgc cagtcttttg      60
gaccagctga tcgaagaggt actggctgat aatcttccac ctcctagcca ttttgaacca    120 cctaccctc acgaactgta tgatttagac gtgacggccc ccgaagatcc caacgaggag     180
gcggtttcgc agattttccc cgactctgta atgttggcgg tgcaggaagg gattgactta    240
ctcacttttc cgccggcgcc cggttctccg gagccgcctc acctttcccg gcagcccgag    300
```

-continued

```
cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cggggggaccc agatattatg tgttcgcttt gctatatgag gacctgtggc    540
atgtttgtct acagtcctgt gtctgaacct gagcctgagc ccgagccaga accggagcct    600
gcaagaccta cccgccgtcc taaaatggcg cctgctatcc tgagacgccc gacatcacct    660
gtgtctagag aatgcaatag tagtacggat agctgtgact ccggtccttc taacacacct    720
cctgagatac acccggtggt cccgctgtgc cccattaaac cagttgccgt gagagttggt    780
gggcgtcgcc aggctgtgga atgtatcgag gacttgctta acgagcctgg caacctttg    840 gacttgagct gtaaacgccc caggccataa                                    870
```

<210> SEQ ID NO 4
<211> LENGTH: 289
<212> TYPE: PRT
<213> ORGANISM: Artificial Sequence
<220> FEATURE:
<223> OTHER INFORMATION: amino acid sequence of human adenovirus type 5, 289R E1A, wild type, protein

<400> SEQUENCE: 4

```
Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Glu Glu Phe Val Leu
    130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
        195                 200                 205

Met Ala Pro Ala Ile Leu Arg Arg Pro Thr Ser Pro Val Ser Arg Glu
    210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255
```

```
Val Arg Val Gly Gly Arg Arg Gln Ala Val Glu Cys Ile Glu Asp Leu
                260                 265                 270

Leu Asn Glu Pro Gly Gln Pro Leu Asp Leu Ser Cys Lys Arg Pro Arg
            275                 280                 285

Pro

<210> SEQ ID NO 5
<211> LENGTH: 732
<212> TYPE: DNA
<213> ORGANISM: Artificial Sequence
<220> FEATURE:
<223> OTHER INFORMATION: nucleotide sequence of human adenovirus type 5,
      243R, wild type

<400> SEQUENCE: 5
atgagacata ttatctgcca cggaggtgtt attaccgaag aaatggccgc cagtcttttg      60
gaccagctga tcgaagaggt actggctgat aatcttccac ctcctagcca ttttgaacca    120
cctacccttc acgaactgta tgatttagac gtgacggccc ccgaagatcc caacgaggag    180
gcggtttcgc agattttttcc cgactctgta atgttggcgg tgcaggaagg gattgactta   240 ctcactttc cgccggcgcc cggttctccg gagccgcctc acctttcccg gcagcccgag     300
cagccggagc agagagcctt gggtccggtt tctatgccaa accttgtacc ggaggtgatc    360
gatcttacct gccacgaggc tggctttcca cccagtgacg acgaggatga gagggtcct    420 gtgtctgaac ctgagcctga gcccgagcca gaaccggagc ctgcaagacc tacccgccgt   480
cctaaaatgg cgcctgctat cctgagacgc ccgacatcac ctgtgtctag agaatgcaat   540
agtagtacgg atagctgtga ctccggtcct tctaacacac ctcctgagat acacccggtg    600
gtcccgctgt gccccattaa accagttgcc gtgagagttg gtgggcgtcg ccaggctgtg    660
gaatgtatcg aggacttgct taacgagcct gggcaacctt tggacttgag ctgtaaacgc   720
cccaggccat aa                                                        732

<210> SEQ ID NO 6
<211> LENGTH: 243
<212> TYPE: PRT
<213> ORGANISM: Artificial Sequence
<220> FEATURE:
<223> OTHER INFORMATION: amino acid sequence of human adenovirus tyep 5,
      243R E1A wild type, protein

<400> SEQUENCE: 6

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125
```

```
Phe Pro Pro Ser Asp Asp Glu Asp Glu Glu Gly Pro Val Ser Glu Pro
        130                 135                 140

Glu Pro Glu Pro Glu Pro Glu Pro Glu Pro Ala Arg Pro Thr Arg Arg
145                 150                 155                 160

Pro Lys Met Ala Pro Ala Ile Leu Arg Arg Pro Thr Ser Pro Val Ser
                165                 170                 175

Arg Glu Cys Asn Ser Ser Thr Asp Ser Cys Asp Ser Gly Pro Ser Asn
            180                 185                 190

Thr Pro Pro Glu Ile His Pro Val Val Pro Leu Cys Pro Ile Lys Pro
        195                 200                 205

Val Ala Val Arg Val Gly Gly Arg Arg Gln Ala Val Glu Cys Ile Glu
    210                 215                 220

Asp Leu Leu Asn Glu Pro Gly Gln Pro Leu Asp Leu Ser Cys Lys Arg
225                 230                 235                 240

Pro Arg Pro

<210> SEQ ID NO 7
<211> LENGTH: 22
<212> TYPE: PRT
<213> ORGANISM: Artificial Sequence
<220> FEATURE:
<223> OTHER INFORMATION: amino acid residues 4-25 of human adenovirus
      type 5, E1A 289R, wild type, protein

<400> SEQUENCE: 7

Ile Ile Cys His Gly Gly Val Ile Thr Glu Glu Met Ala Ala Ser Leu
1               5                   10                  15

Leu Asp Gln Leu Ile Glu
            20

<210> SEQ ID NO 8
<211> LENGTH: 22
<212> TYPE: PRT
<213> ORGANISM: Artificial Sequence
<220> FEATURE:
<223> OTHER INFORMATION: amino acid residues 4-25 of human adenovirus
      type 5, E1A 243R, wild type, protein

<400> SEQUENCE: 8

Ile Ile Cys His Gly Gly Val Ile Thr Glu Glu Met Ala Ala Ser Leu
1               5                   10                  15

Leu Asp Gln Leu Ile Glu
            20

<210> SEQ ID NO 9
<211> LENGTH: 14
<212> TYPE: PRT
<213> ORGANISM: Artificial Sequence
<220> FEATURE:
<223> OTHER INFORMATION: amino acid residues 36-49 of human adenovirus
      type 5, E1A 289R, wild type, protein

<400> SEQUENCE: 9

Ser His Phe Glu Pro Pro Thr Leu His Glu Leu Tyr Asp Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: amino acid residues 36-49 of human adenovirus
```

-continued type 5, E1A 243R, wild type, protein

<400> SEQUENCE: 10

Ser His Phe Glu Pro Pro Thr Leu His Glu Leu Tyr Asp Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: amino acid residues 111-123 of human adenovirus
      type 5, E1A 289R, wild type, protein

<400> SEQUENCE: 11

Ser Met Pro Asn Leu Val Pro Glu Val Ile Asp Leu Thr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: amino acid residues 111-123 of human adenovirus
      type 5, E1A 243R, wild type, protein

<400> SEQUENCE: 12

Ser Met Pro Asn Leu Val Pro Glu Val Ile Asp Leu Thr
1               5                   10

<210> SEQ ID NO 13
<211> LENGTH: 4
<212> TYPE: PRT
<213> ORGANISM: Artificial Sequence
<220> FEATURE:
<223> OTHER INFORMATION: amino acid residues 124-127 of human adenovirus
      type 5, E1A 289R, wild type, protein

<400> SEQUENCE: 13

Cys His Glu Ala
1

<210> SEQ ID NO 14
<211> LENGTH: 4
<212> TYPE: PRT
<213> ORGANISM: Artificial Sequence
<220> FEATURE:
<223> OTHER INFORMATION: amino acid residues 124-127 of human adenovirus
      type 5, E1A 243R, wild type, protein

<400> SEQUENCE: 14

Cys His Glu Ala
1

<210> SEQ ID NO 15
<211> LENGTH: 1491
<212> TYPE: DNA
<213> ORGANISM: Artificial Sequence
<220> FEATURE:
<223> OTHER INFORMATION: nucleotide sequence of human adenovirus type 5,
      E1B-55K, coding region

<400> SEQUENCE: 15
atggagcgaa gaaacccatc tgagcggggg gtacctgctg gattttctgg ccatgcatct       60
gtggagagcg gttgtgagac acaagaatcg cctgctactg ttgtcttccg tccgcccggc      120
gataatcccg acggaggagc agcagcagca gcaggaggaa gccaggcggc ggcggcagga      180

```
gcagagccca tggaacccga gagccggcct ggaccctcgg gaatgaatgt tgtacaggtg      240
gctgaactgt atccagaact gagacgcatt ttgacaatta cagaggatgg cagggggcta     300 aaggggggtaa agagggagcg gggggcttgt gaggctacag aggaggctag gaatctagct     360
tttagcttaa tgaccagaca ccgtcctgag tgtattactt ttcaacagat caaggataat     420
tgcgctaatg agcttgatct gctggcgcag aagtattcca tagagcagct gaccacttac     480
tggctgcagc caggggatga ttttgaggag gctattaggg tatatgcaaa ggtggcactt     540
aggccagatt gcaagtacaa gatcagcaaa cttgtaaata tcaggaattg ttgctacatt     600
tctgggaacg gggccgaggt ggagatagat acggaggata gggtggcctt tagatgtagc     660
atgataaata tgtggccggg ggtgcttggc atggacgggg tggttattat gaatgtaagg     720
tttactggcc ccaattttag cggtacggtt ttcctggcca taccaacct tatcctacac      780 ggtgtaagct tctatgggtt taacaatacc tgtgtggaag cctggaccga tgtaagggtt     840
cggggctgtg cctttactg ctgctggaag ggggtggtgt gtcgcccaa aagcagggct       900 tcaattaaga aatgcctctt tgaaaggtgt accttgggta tcctgtctga gggtaactcc     960
agggtgcgcc acaatgtggc ctccgactgt ggttgcttca tgctagtgaa aagcgtggct    1020
gtgattaagc ataacatggt atgtggcaac tgcgaggaca gggcctctca gatgctgacc    1080
tgctcggacg gcaactgtca cctgctgaag accattcacg tagccagcca ctctcgcaag    1140
gcctggccag tgtttgagca taacatactg acccgctgtt ccttgcattt gggtaacagg    1200
aggggggtgt tcctacctta ccaatgcaat ttgagtcaca ctaagatatt gcttgagccc    1260
gagagcatgt ccaaggtgaa cctgaacggg gtgtttgaca tgaccatgaa gatctggaag    1320
gtgctgaggt acgatgagac ccgcaccagg tgcagaccct gcgagtgtgg cggtaaacat    1380
attaggaacc agcctgtgat gctggatgtg accgaggagc tgaggcccga tcacttggtg    1440
ctggcctgca cccgcgctga gtttggctct agcgatgaag atacagatta             1491
```

<210> SEQ ID NO 16
<211> LENGTH: 496
<212> TYPE: PRT
<213> ORGANISM: Artificial Sequence
<220> FEATURE:
<223> OTHER INFORMATION: amino acid sequence of human Ad type 5, E1B-55K protein

<400> SEQUENCE: 16

```
Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125
```

```
Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
    290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
            340                 345                 350

Asp Arg Ala Ser Gln Met Leu Thr Cys Ser Asp Gly Asn Cys His Leu
        355                 360                 365

Leu Lys Thr Ile His Val Ala Ser His Ser Arg Lys Ala Trp Pro Val
    370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
            420                 425                 430

Asp Met Thr Met Lys Ile Trp Lys Val Leu Arg Tyr Asp Glu Thr Arg
        435                 440                 445

Thr Arg Cys Arg Pro Cys Glu Cys Gly Gly Lys His Ile Arg Asn Gln
    450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495

<210> SEQ ID NO 17
<211> LENGTH: 986
<212> TYPE: DNA
<213> ORGANISM: Artificial Sequence
<220> FEATURE:
<223> OTHER INFORMATION: Nucleotide sequence of human Ad type 5, E1A
      gene
```

<400> SEQUENCE: 17

```
atgagacata ttatctgcca cggaggtgtt attaccgaag aaatggccgc cagtcttttg    60
gaccagctga tcgaagaggt actggctgat aatcttccac ctcctagcca ttttgaacca   120
cctaccttc acgaactgta tgatttagac gtgacggccc ccgaagatcc caacgaggag   180
gcggtttcgc agattttttcc cgactctgta atgttggcgg tgcaggaagg gattgactta   240
ctcacttttc cgccggcgcc cggttctccg gagccgcctc acctttcccg gcagcccgag   300
cagccggagc agagagcctt gggtccggtt tctatgccaa accttgtacc ggaggtgatc   360
gatcttacct gccacgaggc tggctttcca cccagtgacg acgaggatga agagggtgag   420
gagtttgtgt tagattatgt ggagcacccc gggcacggtt gcaggtcttg tcattatcac   480
cggaggaata cgggggaccc agatattatg tgttcgcttt gctatatgag gacctgtggc   540
atgtttgtct acagtaagtg aaaattatgg gcagtgggtg atagagtggt gggtttggtg   600
tggtaatttt ttttttaatt tttacagttt tgtggtttaa agaattttgt attgtgattt   660
ttttaaaagg tcctgtgtct gaacctgagc ctgagcccga ccagaaccg gagcctgcaa   720
gacctacccg ccgtcctaaa atggcgcctg ctatcctgag acgccgaca tcacctgtgt   780
ctagagaatg caatagtagt acggatagct gtgactccgg tccttctaac acacctcctg   840
agatacaccc ggtggtcccg ctgtgcccca ttaaaccagt tgccgtgaga gttggtgggc   900
gtcgccaggc tgtggaatgt atcgaggact tgcttaacga gcctgggcaa cctttggact   960
tgagctgtaa acgccccagg ccataa                                         986
```

<210> SEQ ID NO 18
<211> LENGTH: 1794
<212> TYPE: DNA
<213> ORGANISM: Artificial Sequence
<220> FEATURE:
<223> OTHER INFORMATION: Nucleotide sequence of human Ad type 5, E1B-55K
      and E1B-19K, coding regions
<220> FEATURE:
<221> NAME/KEY: misc_feature
<222> LOCATION: (1)..(529)
<223> OTHER INFORMATION: nucleotide sequence encoding E1B-19K
<220> FEATURE:
<221> NAME/KEY: misc_feature
<222> LOCATION: (306)..(529)
<223> OTHER INFORMATION: Overlapping sequence C-terminal 19K and
      N-terminal 55K - (2019-2242 Ad 5 seq.)
<220> FEATURE:
<221> NAME/KEY: misc_feature
<222> LOCATION: (306)..(1794)
<223> OTHER INFORMATION: nucleotide sequence encoding E1B-55K

<400> SEQUENCE: 18

```
atggaggctt gggagtgttt ggaagatttt tctgctgtgc gtaacttgct ggaacagagc    60
tctaacagta cctcttggtt ttggaggttt ctgtggggct catcccaggc aaagttagtc   120
tgcagaatta aggaggatta caagtgggaa tttgaagagc ttttgaaatc ctgtggtgag   180
ctgtttgatt ctttgaatct gggtcaccag gcgcttttcc aagagaaggt catcaagact   240
ttggatttt ccacaccggg gcgcgctgcg gctgctgttg cttttttgag ttttataaag   300
gataaatgga gcgaagaaac ccatctgagc gggggtacc tgctggattt tctggccatg   360
catctgtgga gagcggttgt gagacacaag aatcgcctgc tactgttgtc ttccgtccgc   420
ccggcgataa taccgacgga ggagcagcag cagcagcagg aggaagccag gcggcggcgg   480
caggagcaga gccatggaa cccgagagcc ggcctggacc ctcggaatg aatgttgtac   540
aggtggctga actgtatcca gaactgagac gcattttgac aattacagag gatgggcagg   600
```

| | |
|---|---:|
| ggctaaaggg ggtaaagagg gagcgggggg cttgtgaggc tacagaggag gctaggaatc | 660 |
| tagcttttag cttaatgacc agacaccgtc ctgagtgtat tacttttcaa cagatcaagg | 720 |
| ataattgcgc taatgagctt gatctgctgg cgcagaagta ttccatagag cagctgacca | 780 |
| cttactggct gcagccaggg gatgattttg aggaggctat tagggtatat gcaaaggtgg | 840 |
| cacttaggcc agattgcaag tacaagatca gcaaacttgt aaatatcagg aattgttgct | 900 |
| acatttctgg gaacggggcc gaggtggaga tagatacgga ggatagggtg gcctttagat | 960 |
| gtagcatgat aaatatgtgg ccgggggtgc ttggcatgga cggggtggtt attatgaatg | 1020 |
| taaggtttac tggccccaat tttagcggta cggttttcct ggccaatacc aaccttatcc | 1080 |
| tacacggtgt aagcttctat gggtttaaca atacctgtgt ggaagcctgg accgatgtaa | 1140 |
| gggttcgggg ctgtgccttt tactgctgct ggaaggggt ggtgtgtcgc cccaaaagca | 1200 |
| gggcttcaat taagaaatgc ctctttgaaa ggtgtacctt gggtatcctg tctgagggta | 1260 |
| actccagggt gcgccacaat gtggcctccg actgtggttg cttcatgcta gtgaaaagcg | 1320 |
| tggctgtgat taagcataac atggtatgtg gcaactgcga ggacagggcc tctcagatgc | 1380 |
| tgacctgctc ggacggcaac tgtcacctgc tgaagaccat tcacgtagcc agccactctc | 1440 |
| gcaaggcctg gccagtgttt gagcataaca tactgacccg ctgttccttg catttgggta | 1500 |
| acaggagggg ggtgttccta ccttaccaat gcaatttgag tcacactaag atattgcttg | 1560 |
| agcccgagag catgtccaag gtgaacctga acggggtgtt tgacatgacc atgaagatct | 1620 |
| ggaaggtgct gaggtacgat gagacccgca ccaggtgcag accctgcgag tgtggcggta | 1680 |
| aacatattag gaaccagcct gtgatgctgg atgtgaccga ggagctgagg cccgatcact | 1740 |
| tggtgctggc ctgcacccgc gctgagtttg gctctagcga tgaagataca gatt | 1794 |

<210> SEQ ID NO 19
<211> LENGTH: 11128
<212> TYPE: DNA
<213> ORGANISM: Artificial Sequence
<220> FEATURE:
<223> OTHER INFORMATION: plasmid pVITRO2IRESPuroE1b

<400> SEQUENCE: 19

| | |
|---|---:|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catgatgatg cggttttggc agtacatcaa tgggcgtgga tagcggtttg | 660 |
| actcacgggg atttccaagt ctccacccca ttgacgtcaa tgggagtttg ttttgactag | 720 |
| tcagggcccc aacccccca agccccatt tcacaacacg ctggcgctac aggcgcgtga | 780 |
| cttcccttg ctttggggcg gggggctgag actcctatgt gctccggatt ggtcaggcac | 840 |

```
ggccttcggc cccgcctcct gccaccgcag attggccgct aggcctcccc gagcgccctg    900
cctccgaggg ccggcgcacc ataaaagaag ccgccctagc cacgtcccct cgcagttcgg    960
cggtcccgcg ggtctgtctc aagcttgccg ccagaacaca ggtaagtgcc gtgtgtggtt   1020
cccgcgggcc tggcctcttt acgggttatg gcccttgcgt gccttgaatt acttccatgc   1080
ccctggctgc agtacgtgat tcttgatccc gagcttcggg ttggaagtgg gtgggagagt   1140
tcgaggcctt gcgcttaagg agccccttcg cctcgtgctt gagttgaggc ctggcttggg   1200
cgctggggcc gccgcgtgct aatctggtgg caccttcgcg cctgtctcgc tgctttcgct   1260
aagtctctag ccatttaaaa ttttgataa ccagctgcga cgctttttt ctggcgagat    1320
agtcttgtaa atgcgggcca ggatctgcac actggtattt cggttttgg ggccgcgggc   1380
ggcgacgggg cccgtgcgtc ccagcgcaca tgttcggcga ggcggggcct gcgagcgcgg   1440
ccaccgagaa tcggacgggg gtagtctcaa actggccggc ctgctctggt gcctggcctc   1500
gcgccgccgt gtatcgcccc gccctgggcg gcaaggctgg cccggtcggc accagttgcg   1560
tgagcggaaa gatggccgct tcccggccct gctgcaggga gctcaaaatg gaggacgcgg   1620
cgcccgggag agcgggcggg tgagtcaccc acacaaagga aaagggcctt tccttcctca   1680
tccgtcgctt catgtgactc cacggagtac cgggcgccgt ccaggcacct cgattagttg   1740
tcgagctttt ggagtacgtc gtctttaggt tgggggagg ggttttatgc gatggagttt    1800
ccccacactg agtgggtgga gactgaagag ttaggccagc ttggcacttg atgtaattct   1860
ccttggaatt tgccctttt gagtttggat cttgcctcat tctcaagcct cagacagtgg    1920
ttcaaagttt ttttcttcca tttcaggtgt cgtgaaaact accctaaaa gccaccggcg     1980
tgcgcaagat ctgaattctt cgaactcgag gctagctggc cagacatgat aagatacatt   2040
gatgagtttg gacaaaccac aactagaatg cagtgaaaaa aatgctttat ttgtgaaatt   2100
tgtgatgcta ttgctttatt tgtaaccatt ataagctgca ataaacaagt taacaacaac   2160
aattgcattc atttatgtt tcaggttcag ggggaggtgt gggaggtttt ttaaagcaag    2220
taaaacctct acaaatgtgg tatggaaatg ttaattaact agccatgacc aaaatccctt   2280
aacgtgagtt ttcgttccac tgagcgtcag accccgtaga aagatcaaa ggatcttctt    2340
gagatccttt ttttctgcgc gtaatctgct gcttgcaaac aaaaaaacca ccgctaccag   2400
cggtggtttg tttgccggat caagagctac caactctttt tccgaaggta actggcttca   2460
gcagagcgca gataccaaat actgttcttc tagtgtagcc gtagttaggc caccacttca   2520
agaactctgt agcaccgcct acatacctcg ctctgctaat cctgttacca gtggctgctg   2580
ccagtggcga taagtcgtgt cttacccggg tggactcaag acgatagtta ccggataagg   2640
cgcagcggtc gggctgaacg gggggttcgt gcacacagcc cagcttggag cgaacgacct   2700
acaccgaact gagataccta cagcgtgagc tatgagaaag cgccacgctt cccgaaggga   2760
gaaaggcgga caggtatccg gtaagcggca gggtcggaac aggagagcgc acgagggagc   2820
ttccaggggg aaacgcctgg tatctttata gtcctgtcgg gtttcgccac ctctgacttg   2880
agcgtcgatt tttgtgatgc tcgtcagggg ggcggagcct atggaaaaac gccagcaacg   2940
cggccttttt acggttcctg gccttttgct ggccttttgc tcacatgttc ttaattaacc   3000
tgcagggcct gaaataacct ctgaaagagg aacttggtta ggtaccttct gaggctgaaa   3060
gaaccagctg tggaatgtgt gtcagttagg gtgtggaaag tccccaggct ccccagcagg   3120
cagaagtatg caaagcatgc atctcaatta gtcagcaacc aggtgtggaa agtccccagg   3180
ctccccagca ggcagaagta tgcaaagcat gcatctcaat tagtcagcaa ccatagtccc   3240
```

-continued

```
actagttccg ccagagcgcg cgagggcctc cagcggccgc ccctccccca cagcaggggc    3300
ggggtcccgc gcccaccgga aggagcgggc tcggggcggg cggcgctgat tggccggggc    3360
gggcctgacg ccgacgcggc tataagagac cacaagcgac ccgcagggcc agacgttctt    3420
cgccgaagct tgccgtcaga acgcaggtga ggggcgggtg tggcttccgc gggccgccga    3480
gctggaggtc ctgctccgag cgggccggcc ccgctgtcg tcgcggggga ttagctgcga     3540
gcattcccgc ttcgagttgc gggcggcgcg ggaggcagag tgcgaggcct agcggcaacc    3600
ccgtagcctc gcctcgtgtc cggcttgagg cctagcgtgg tgtccgcgcc gccgccgcgt    3660
gctactccgg ccgcactctg gtcttttttt tttttgttgt tgttgccctg ctgccttcga    3720
ttgccgttca gcaataggg ctaacaaagg gagggtgcgg ggcttgctcg cccggagccc     3780
ggagaggtca tggttgggga ggaatggagg gacaggagtg gcggctgggg cccgcccgcc    3840
ttcggagcac atgtccgacg ccacctggat ggggcgaggc ctgggtttt tcccgaagca     3900 accaggctgg ggttagcgtg ccgaggccat gtggcccag cacccggcac gatctggctt     3960
ggcggcgccg cgttgccctg cctccctaac tagggtgagg ccatcccgtc cggcaccagt    4020
tgcgtgcgtg gaaagatggc cgctcccggg ccctgttgca aggagctcaa aatggaggac    4080
gcggcagccc ggtggagcgg gcgggtgagt cacccacaca aaggaagagg gcctggtccc    4140
tcaccggctg ctgcttcctg tgaccccgtg gtcctatcgg ccgcaatagt cacctcgggc    4200
ttttgagcac ggctagtcgc ggcgggggga ggggatgtaa tggcgttgga gtttgttcac    4260
atttggtggg tggagactag tcaggccagc ctggcgctgg aagtcatttt tggaatttgt    4320
ccccttgagt tttgagcgga gctaattctc gggcttctta gcggttcaaa ggtatctttt    4380 aaacccttt ttaggtgttg tgaaaaccac cgctaattca aagcaaccgg tgataattcg     4440
cccttaaccg gtgggcttaa agggtatata atgcgccgtg ggctaatctt ggttacatct    4500
gacctcatgg aggcttggga gtgtttggaa gattttctg ctgtgcgtaa cttgctggaa     4560
cagagctcta acagtacctc ttggttttgg aggtttctgt ggggctcatc ccaggcaaag    4620
ttagtctgca gaattaagga ggattacaag tgggaatttg aagagctttt gaaatcctgt    4680
ggtgagctgt ttgattcttt gaatctgggt caccaggcgc ttttccaaga aaggtcatc     4740 aagactttgg atttttccac accggggcgc gctgcggctg ctgttgcttt tttgagtttt    4800 ataaggata aatggagcga agaaacccat ctgagcgggg ggtacctgct ggattttctg     4860
gccatgcatc tgtggagagc ggttgtgaga cacaagaatc gcctgctact gttgtcttcc    4920
gtccgcccgg cgataatacc gacggaggag cagcagcagc agcaggagga agccaggcgg    4980
cggcggcagg agcagagccc atggaaccg agagccggcc tggaccctcg ggaatgaatg     5040
ttgtacaggt ggctgaactg tatccagaac tgagacgcat tttgacaatt acagaggatg    5100
ggcaggggct aaaggggta aagagggagc gggggcttg tgaggctaca gaggaggcta      5160
ggaatctagc ttttagctta atgaccagac accgtcctga gtgtattact tttcaacaga    5220
tcaaggataa ttgcgctaat gagcttgatc tgctggcgca gaagtattcc atagagcagc    5280
tgaccactta ctggctgcag ccaggggatg attttgagga ggctattagg gtatatgcaa    5340
aggtggcact taggccagat tgcaagtaca agatcagcaa acttgtaaat atcaggaatt    5400
gttgctacat ttctgggaac ggggccgagg tggagataga tacggaggat agggtggcct    5460
ttagatgtag catgataaat atgtggccgg ggtgcttgg catggacggg gtggttatta    5520
tgaatgtaag gtttactggc cccaatttta gcggtacggt tttcctggcc aataccaacc    5580
```

```
ttatcctaca cggtgtaagc ttctatgggt ttaacaatac ctgtgtgaa gcctggaccg    5640
atgtaagggt tcggggctgt gccttttact gctgctggaa gggggtggtg tgtcgcccca   5700
aaagcagggc ttcaattaag aaatgcctct ttgaaaggtg taccttgggt atcctgtctg   5760
agggtaactc cagggtgcgc cacaatgtgg cctccgactg tggttgcttc atgctagtga   5820
aaagcgtggc tgtgattaag cataacatgg tatgtggcaa ctgcgaggac agggcctctc   5880
agatgctgac ctgctcggac ggcaactgtc acctgctgaa gaccattcac gtagccagcc   5940
actctcgcaa ggcctggcca gtgtttgagc ataacatact gacccgctgt tccttgcatt   6000
tgggtaacag gagggggtg ttcctacctt accaatgcaa tttgagtcac actaagatat     6060
tgcttgagcc cgagagcatg tccaaggtga acctgaacgg ggtgtttgac atgaccatga   6120
agatctggaa ggtgctgagg tacgatgaga cccgcaccag gtgcagaccc tgcgagtgtg   6180
gcggtaaaca tattaggaac cagcctgtga tgctggatgt gaccgaggag ctgaggcccg   6240
atcacttggt gctggcctgc acccgcgctg agtttggctc tagcgatgaa gatacagatt   6300
gaggtactga aatgtgtggg cgtggcttaa gggtgggaaa gaatatataa ggtgggggtc   6360
ttatgtagtt ttgtatctgt tttgcagcag ccgccgccgc catgagcacc aactcgtttg   6420
atggaagcat tgtgagctca tatttgacaa cgcgcatgcc cccatgggcc ggggtgcgtc   6480
agaatgtgat gggctccagc attgatggtc gcccgtcct gcccgcaaac tctactacct     6540
tgacctacga gaccgtgtct ggaacgccgt tggagactgc agcctccgcc gccgcttcag   6600
ccgctgcagc caccgcccgc gggattgtga ctgactttgc tttcctgagc ccgcttgcaa   6660
gcagtgcagc ttcccgttca tccgcccgcg atgacaagtt gacggctctt ttggcacaat   6720
tggattcttt gacccgggaa cttaatgtcg tttctcagca gctgttggat ctgcgccagc   6780
aggtttctgc cctgaaggct tcctcccctc ccaatgcggt ttaaaacata aataaaaaac   6840
cagactctgt ttggatttgg catcgatcta agggttggat catcggatcc acgcgtatcg   6900
attgtcgaat tcggatccgc ggccgcatag ataactgatc cagtgtgctg gaattaattc   6960
gctgtctgcg agggccagct gttggggtga gtactccctc tcaaaagcgg gcatgacttc   7020
tgcgctaaga ttgtcagttt ccaaaaacga ggaggatttg atattcacct ggcccgcggt   7080
gatgcctttg agggtggccg cgtccatctg gtcagaaaag acaatctttt tgttgtcaag   7140
cttgaggtgt ggcaggcttg agatctggcc atacacttga gtgacaatga catccacttt   7200
gcctttctct ccacaggtgt ccactcccag gtccaactgc aggtcgagca tgcatctagg   7260
gcggccaatt ccgcccctct ccctccccc ccctaacgt tactggccga agccgcttgg      7320
aataaggccg gtgtgcgttt gtctatatgt gattttccac catattgccg tcttttggca   7380
atgtgagggc ccggaaacct ggccctgtct tcttgacgag cattcctagg ggtctttccc   7440
ctctcgccaa aggaatgcaa ggtctgttga atgtcgtgaa ggaagcagtt cctctggaag   7500
cttcttgaag acaaacaacg tctgtagcga ccctttgcag gcagcggaac cccccacctg   7560
gcgacaggtg cctctgcggc caaaagccac gtgtataaga tacacctgca aaggcggcac   7620
aaccccagtg ccacgttgtg agttggatag ttgtggaaag agtcaaatgg ctctcctcaa   7680
gcgtattcaa caaggggctg aaggatgccc agaaggtacc ccattgtatg ggatctgatc   7740
tggggcctcg gtgcacatgc tttacatgtg tttagtcgag gttaaaaaaa cgtctaggcc   7800
ccccgaacca cggggacgtg gttttccttt gaaaaacacg atgataagct tgccacaacc   7860
cacaaggaga cgaccttcca tgaccgagta caagcccacg gtgcgcctcg ccacccgcga   7920
cgacgtcccc cgggccgtac gcaccctcgc cgccgcgttc gccgactacc ccgccacgcg   7980
```

```
ccacaccgtc gacccggacc gccacatcga gcgggtcacc gagctgcaag aactcttcct      8040
cacgcgcgtc gggctcgaca tcggcaaggt gtgggtcgcg gacgacggcg ccgcggtggc      8100
ggtctggacc acgccggaga gcgtcgaagc gggggcggtg ttcgccgaga tcggcccgcg      8160
catggccgag ttgagcggtt cccggctggc cgcgcagcaa cagatggaag gcctcctggc      8220
gccgcaccgg cccaaggagc ccgcgtggtt cctggccacc gtcggcgtct cgcccgacca      8280
ccagggcaag ggtctgggca gcgccgtcgt gctccccgga gtggaggcgg ccgagcgcgc      8340
cggggtgccc gccttcctgg agacctccgc gccccgcaac ctccccttct acgagcggct      8400
cggcttcacc gtcaccgccg acgtcgagtg cccgaaggac cgcgcgacct ggtgcatgac      8460
ccgcaagccc ggtgcctgac gcccgcccca cgacccgcag cgcccgaccg aaaggagcgc      8520
acgaccccat ggctccgacc gaagccgacc cgggcggccc cgccgacccc gcacccgccc      8580
ccgaggccca ccgactctag agctcgctga tcagcctcga ctgtgccttc tagttgccag      8640
ccatctgttg tttgcccctc ccccgtgcct tccttgaccc tggaaggtgc cactcccact      8700
gtcctttcct aataaaatga ggaaattgca tcgcattgtc tgagtaggtg tcattctatt      8760
ctgggggtg gggtggggca ggacagcaag ggggaggatt gggaagacaa tagcaggcat      8820
gctggggatg cggtgggctc tatggcttct gaggcggaaa gaaccagctg gggctcgagt      8880
gcattctagt tgtggtttgt ccaaactcat caatgtatct tatcatgtct gtataccgtc      8940
gacctctagc tagagcttgg cgtaatcatg gtcatagctg tttcctgtgt gaaattgtta      9000
tccgctcaca attccacaca acatacgagc cggaagcata aagtgtaaag cctggggtgc      9060
ctaatgagtg agctaactca cattaattgc gttgcgctca ctgcccgctt tccagtcggg      9120
aaacctgtcg tgccagctgc attaatgaat cggccaacgc gcggggagag gcggtttgcg      9180
tattgggcgc tcttccgctt cctcgctcac tgactcgctg cgctcggtcg ttcggctgcg      9240
gcgagcggta tcagctcact caaaggcggt aatacggtta tccacagaat caggggataa      9300
cgcaggaaag aacatgtgag caaaaggcca gcaaaaggcc aggaaccgta aaaaggccgc      9360
gttgctggcg ttttttccata ggctccgccc ccctgacgag catcacaaaa atcgacgctc      9420
aagtcagagg tggcgaaacc cgacaggact ataaagatac caggcgtttc ccnctggaag      9480
ctccctcgtg cgctctcctg ttccgaccct gccgcttacc ggatacctgt ccgcctttct      9540
cccttcggga agcgtggcgc tttctcaatg ctcacgctgt aggtatctca gttcggtgta      9600
ggtcgttcgc tccaagctgg gctgtgtgca cgaaccccc gttcagcccg accgctgcgc      9660
cttatccggt aactatcgtc ttgagtccaa cccggtaaga cacgacttat cgccactggc      9720
agcagccact ggtaacagga ttagcagagc gaggtatgta ggcggtgcta cagagttctt      9780
gaagtggtgg cctaactacg gctacactag aaggacagta tttggtatct gcgctctgct      9840
gaagccagtt accttcggaa aaagagttgg tagctcttga tccggcaaac aaaccaccgc      9900
tggtagcggt ggtttttttg tttgcaagca gcagattacg cgcagaaaaa aaggatctca      9960
agaagatcct ttgatctttt ctacggggtc tgacgctcag tggaacgaaa actcacgtta     10020
agggattttg gtcatgagat tatcaaaaag gatcttcacc tagatccttt taaattaaaa     10080
atgaagtttt aaatcaatct aaagtatata tgagtaaact tggtctgaca gttaccaatg     10140
cttaatcagt gaggcaccta tctcagcgat ctgtctattt cgttcatcca tagttgcctg     10200
actccccgtc gtgtagataa ctacgatacg ggagggctta ccatctggcc ccagtgctgc     10260
aatgataccg cgagacccac gctcaccggc tccagattta tcagcaataa accagccagc     10320
```

```
cggaagggcc gagcgcagaa gtggtcctgc aactttatcc gcctccatcc agtctattaa    10380
ttgttgccgg gaagctagag taagtagttc gccagttaat agtttgcgca acgttgttgc    10440
cattgctaca ggcatcgtgg tgtcacgctc gtcgtttggt atggcttcat tcagctccgg    10500
ttcccaacga tcaaggcgag ttacatgatc ccccatgttg tgcaaaaaag cggttagctc    10560
cttcggtcct ccgatcgttg tcagaagtaa gttggccgca gtgttatcac tcatggttat    10620
ggcagcactg cataattctc ttactgtcat gccatccgta agatgctttt ctgtgactgg    10680
tgagtactca accaagtcat tctgagaata gtgtatgcgg cgaccgagtt gctcttgccc    10740
ggcgtcaata cgggataata ccgcgccaca tagcagaact ttaaaagtgc tcatcattgg    10800
aaaacgttct cggggcgaaa actctcaag gatcttaccg ctgttgagat ccagttcgat    10860
gtaacccact cgtgcaccca actgatcttc agcatctttt actttcacca gcgtttctgg    10920
gtgagcaaaa acaggaaggc aaaatgccgc aaaaaaggga ataagggcga cacggaaatg    10980
ttgaatactc atactcttcc ttttttcaata ttattgaagc atttatcagg gttattgtct    11040
catgagcgga tacatatttg aatgtattta gaaaaataaa caaatagggg ttccgcgcac    11100
atttccccga aaagtgccac ctgacgtc                                      11128

<210> SEQ ID NO 20
<211> LENGTH: 9287
<212> TYPE: DNA
<213> ORGANISM: Artificial Sequence
<220> FEATURE:
<223> OTHER INFORMATION: plasmid pMGCMVE2Bpol

<400> SEQUENCE: 20
ggatctgcga tcgctccggt gcccgtcagt gggcagagcg cacatcgccc acagtccccg       60
agaagttggg gggaggggtc ggcaattgaa ccggtgccta gagaaggtgg cgcggggtaa      120
actgggaaag tgatgtcgtg tactggctcc gccttttcc cgagggtggg ggagaaccgt       180
atataagtgc agtagtcgcc gtgaacgttc tttttcgcaa cgggtttgcc gccagaacac      240
agctgaagct tcgaggggct cgcatctctc cttcacgcgc ccgccgccct aacctgaggcc     300 gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacgtaagt gatatctact agattatca aaaagagtgt tgacttgtga gcgctcacaa     600
ttgatactta gattcatcga gagggacacg tcgactacta accttcttct ctttcctaca     660
gctgagatca ccgcgaagg aggcctagat ctatcgattg tacagctagc tcgacatgat      720
aagatacatt gatgagtttg gacaaaccac aactagaatg cagtgaaaaa aatgctttat     780
ttgtgaaatt tgtgatgcta ttgctttatt tgtgaaattt gtgatgctat tgctttattt     840
gtaaccatta taagctgcaa taaacaagtt aacaacaaca attgcattca tttttatgttt    900 caggttcagg gggaggtgtg ggaggttttt taaagcaagt aaaacctcta caaatgtggt     960
agatcattta aatgttaatt aagaacatgt gagcaaaagg ccagcaaaag gccaggaacc    1020
gtaaaaaggc cgcgttgctg gcgttttcc ataggctccg cccccctgac gagcatcaca     1080
aaaatcgacg ctcaagtcag aggtggcgaa acccgacagg actataaaga taccaggcgt    1140
ttccccctgg aagctccctc gtgcgctctc ctgttccgac cctgccgctt accggatacc    1200
tgtccgcctt tctcccttcg ggaagcgtgg cgctttctca tagctcacgc tgtaggtatc    1260
```

```
tcagttcggt gtaggtcgtt cgctccaagc tgggctgtgt gcacgaaccc cccgttcagc    1320
ccgaccgctg cgccttatcc ggtaactatc gtcttgagtc caacccggta agacacgact    1380
tatcgccact ggcagcagcc actggtaaca ggattagcag agcgaggtat gtaggcggtg    1440
ctacagagtt cttgaagtgg tggcctaact acggctacac tagaagaaca gtatttggta    1500
tctgcgctct gctgaagcca gttaccttcg aaaaagagt tggtagctct tgatccggca     1560
aacaaaccac cgctggtagc ggtggttttt ttgtttgcaa gcagcagatt acgcgcagaa    1620 aaaaggatc tcaagaagat cctttgatct tttctacggg gtctgacgct cagtggaacg     1680
aaaactcacg ttaagggatt ttggtcatgg ctagttaatt aagctgcaat aaacaatcat    1740
tattttcatt ggatctgtgt gttggttttt tgtgtgggct tgggggaggg ggaggccaga    1800
atgactccaa gagctacagg aaggcaggtc agagacccca ctggacaaac agtggctgga    1860
ctctgcacca taacacacaa tcaacagggg agtgagctgg atcgagctag agtccgttac    1920
ataacttacg gtaaatggcc cgcctggctg accgcccaac gacccccgcc cattgacgtc    1980
aataatgacg tatgttccca tagtaacgcc aatagggact ttccattgac gtcaatgggt    2040
ggagtattta cggtaaactg cccacttggc agtacatcaa gtgtatcata tgccaagtac    2100
gccccctatt gacgtcaatg acggtaaatg gcccgcctgg cattatgccc agtacatgac    2160
cttatgggac tttcctactt ggcagtacat ctacgtatta gtcatcgcta ttaccatggt    2220
gatgcggttt tggcagtaca tcaatgggcg tggatagcgg tttgactcac ggggatttcc    2280
aagtctccac cccattgacg tcaatgggag tttgttttgg caccaaaatc aacgggactt    2340
tccaaaatgt cgtaacaact ccgccccatt gacgcaaatg ggcggtaggc gtgtacggtg    2400
ggaggtctat ataagcagag ctcgtttagt gaaccgtcag atcgcctgga dacgccatcc    2460
acgctgtttt gacctccata agacaccg ggaccgatcc agcctccgcg gccgggaacg     2520
gtgcattgga acgcggattc cccgtgccaa gagtgacgta agtaccgcct atagagtcta    2580
taggcccacc cccttggctt cttatgcatg ctatactgtt tttggcttgg ggtctataca    2640
cccccgcttc ctcatgttat aggtgatggt atagcttagc ctataggtgt gggttattga    2700
ccattattga ccactcccct attggtgacg atacttttcca ttactaatcc ataacatggc    2760
tctttgccac aactctcttt attggctata tgccaataca ctgtccttca gagactgaca    2820
cggactctgt atttttacag gatggggtct catttattat ttacaaattc acatatacaa    2880
caccaccgtc cccagtgccc gcagttttta ttaaacataa cgtgggatct ccacgcgaat    2940
ctcgggtacg tgttccggac atgggctctt ctccggtagc ggcggagctt ctacatccga    3000
gccctgctcc catgcctcca gcgactcatg gtcgctcggc agctccttgc tcctaacagt    3060
ggaggccaga cttaggcaca gcacgatgcc caccaccacc agtgtgccgc acaaggccgt    3120
ggcggtaggg tatgtgtctg aaaatgagct cggggagcgg gcttgcaccg ctgacgcatt    3180
tggaagactt aaggcagcgg cagaagaaga tgcaggcagc tgagttgttg tgttctgata    3240
agagtcagag gtaactcccg ttgcggtgct gttaacggtg gagggcagtg tagtctgagc    3300
agtactcgtt gctgccgcgc gcgccaccag acataatagc tgacagacta acagactgtt    3360
cctttccatg ggtctttcct gcagtcaccc ggggatcta tggccttggt tcaagctcac    3420
cgggcccgtc gtcttcacgc agaggcgcca gattcaggag atcaaccgcc gcgtcgtcgc    3480
gttcgccagc aacctacgcg cgcagcacca gctcctgccc gcgcgcggcg ccgacgtgcc    3540 cctgcccct ctcccggcgg gtccggagcc cccctacct ccggggctc gcccgcgtca       3600
```

```
ccgcttttag atgcatcatc caaggacacc cccgcggccc accgcccgcc gcgcggtacc    3660
gtagtcgcgc cgcggggatg cggcctcttg caagccatcg acgccgccac caaccagccc    3720
ctggaaatta ggtatcacct ggatctagcc cgcgccctga cccgtctatg cgaggtaaac    3780
ctgcaggagc tcccgcctga cctgacgccg cgggagctcc agaccatgga cagctcccat    3840
ctgcgcgatg ttgtcatcaa gctccgaccg ccgcgcgcgg acatctggac tttgggctcg    3900
cgcggcgtgg tggtccgatc caccgtaact ccccctcgagc agccagacgg tcaaggacaa    3960
gcagccgaag tagaagacca ccagccaaac ccgccaggcg aggggctcaa attcccactc    4020
tgcttccttg tgcgcggtcg tcaggtcaac ctcgtgcagg atgtacagcc cgtgcaccgc    4080
tgccagtact gcgcacgttt ttacaaaagc cagcacgagt gttcggcccg tcgcagggac    4140
ttctactttc accacatcaa cagccactcc tccaactggt ggcgggagat ccagttcttc    4200
ccgatcggct cgcatcctcg caccgagcgt ctctttgtca cctacgatgt agagacctat    4260
acttggatgg gggcctttgg gaagcagctc gtgcccttca tgctggttat gaagttcggc    4320
ggagatgagc ctctggtgac cgccgcgcga gacctagccg tggaccttgg atgggaccgc    4380
tgggaacaag acccgcttac cttctactgc atcaccccag aaaaaatggc cataggtcgc    4440
cagtttagga cctttcgcga ccacctgcaa atgctaatgg cccgtgacct gtggagctca    4500
ttcgtcgctt ccaaccctca tcttgcagac tgggccctgt cagaacacgg gctcagctcc    4560
cctgaggagc tcacctacga ggaacttaaa aaattgccct ccatcaaggg caccccgcgc    4620
ttcttggaac tttacatcgt gggccacaac atcaacggct cgacgagat cgtgctcgcc    4680
gcccaggtaa ttaacaaccg ttccgaggtg ccgggaccct tccgcatcac acgcaacttt    4740
atgcctcgcg cgggaaagat acttttcaac gatgtcacct tcgccctgcc aaacccgcgt    4800
tccaaaaagc gcacggactt tttgctctgg gagcagggcg gatgcgacga cactgacttc    4860
aaataccagt acctcaaagt catggttagg acaccctttg cgctcaccca cacctcgctc    4920
cggaaggccg cgcaggcata cgcgctaccc gtagaaaagg gatgctgcgc ctaccaggcc    4980
gtcaaccagt tctacatgct aggctcttac cgttcggagg ccgacgggtt tccgatccaa    5040
gagtactgga aagaccgcga agagtttgtc ctcaaccgcg agctgtggaa aaaaagggga    5100
caggataagt atgacatcat caaggaaacc ctggactact gcgccctaga cgtgcaggtc    5160
accgccgagc tggtcaacaa gctgcgcgac tcctacgcct ccttcgtgcg tgacgcggta    5220
ggtctcacag acgccagctt caacgtcttc cagcgtccaa ccatatcatc caactcacat    5280
gccatcttca ggcagatagt cttccgagca gagcagcccg cccgtagcaa cctcggtccc    5340
gacctcctcg ctccctcgca cgaactatac gattacgtgc gcgccagcat ccgcggtgga    5400
agatgctacc ctacatatct tggaatactc agagagcccc tctacgttta cgacatttgc    5460
ggcatgtacg cctccgcgct cacccacccc atgccatggg gtcccccact caacccatac    5520
gagcgcgcgc ttgccgcccg cgcatggcag caggcgctag acttgcaagg atgcaagata    5580
gactacttcg acgcgcgcct gctgcccggg gtctttaccg tggacgcaga ccccccggac    5640
gagacgcagc tagaccccact accgccattc tgttcgcgca agggcggccg cctctgctgg    5700
accaacgagc gcctacgcgg agaggtagcc accagcgttg accttgtcac cctgcacaac    5760
cgcggttggc gcgtgcacct ggtgcccgac gagcgcacca ccgtctttcc cgaatggcgg    5820
tgcgttgcgc gcgaatacgt gcagctaaac atcgcggcca aggagcgcgc cgatcgcgac    5880
aaaaaccaaa ccctgcgctc catcgccaag ttgctgtcca acgccctcta cgggtcgttt    5940
gccaccaagc ttgacaacaa aaagattgtc ttttctgacc agatggacgc ggccaccctc    6000
```

```
aaaggcatca ccgcgggcca ggtgaatatc aaatcctcct cgttttttgga aactgacaat   6060
cttagcgcag aagtcatgcc cgcttttgag agggagtact caccccaaca gctggccctc   6120
gcagacagcg atgcggaaga gagtgaggac gaacgcgccc ccaccccctt ttatagcccc   6180
ccttcaggaa cacccggtca cgtggcctac acctataaac caatcacctt ccttgatgcc   6240
gaagagggca catgtgtct tcacaccctg gagcgagtgg accccctagt ggacaacgac   6300
cgctacccct cccacttagc ctccttcgtg ctggcctgga cgcgagcctt cgtctcagag   6360
tggtccgagt ttctatacga ggaggaccgc ggaacaccgc tcgaggacag gcctctcaag   6420
tctgtatacg gggacacgga cagccttttc gtcaccgagc gtggacaccg gctcatggaa   6480
accagaggta agaaacgcat caaaaagcat gggggaaacc tggttttttga ccccgaacgg   6540
ccagagctca cctggctcgt ggaatgcgag accgtctgcg gggcctgcgg cgcggatgcc   6600
tactccccgg aatcggtatt tctcgcgccc aagctctacg cccttaaaag tctgcactgc   6660
ccctcgtgcg gcgcctcctc caagggcaag ctgcgcgcca agggccacgc cgcggagggg   6720
ctggactatg acaccatggt caaatgctac ctggccgacg cgcagggcga agaccggcag   6780
cgcttcagca ccagcaggac cagcctcaag cgcaccctgg ccagcgcgca gcccggagcg   6840
caccccttca ccgtgaccca gactacgctg acgaggaccc tgcgcccgtg gaaagacatg   6900
accctggccc gtctggacga gcaccgacta ctgccgtaca gcgaaagccg ccccaacccg   6960
cgaaacgagg agatatgctg gatcgagatg ccgtagagca cgtgaccgag ctgtgggacc   7020
gcctggaact gcttggtcaa acgctcaaaa gatcggatcc ttcgaacgta gctctagatt   7080
gagtcgacgt tactggccga agccgcttgg aataaggccg gtgtgcgttt gtctatatgt   7140
tatttttccac catattgccg tcttttggca atgtgagggc ccggaaacct ggccctgtct   7200
tcttgacgag cattcctagg ggtctttccc ctctcgccaa aggaatgcaa ggtctgttga   7260
atgtcgtgaa ggaagcagtt cctctggaag cttcttgaag acaaacaacg tctgtagcga   7320
cccttttgcag gcagcggaac ccccacctg gcgacaggtg cctctgcggc aaaagccac    7380
gtgtataaga tacacctgca aaggcggcac aaccccagtg ccacgttgtg agttggatag   7440
ttgtggaaag agtcaaatgg ctctcctcaa gcgtattcaa caaggggctg aaggatgccc   7500
agaaggtacc ccattgtatg ggatctgatc tgggcctcg gtgcacatgc tttcatgtg     7560
tttagtcgag gttaaaaaaa cgtctaggcc ccccgaacca cggggacgtg gttttccttt   7620
gaaaaacacg ataataccat gggtaagtga tatctactag ttgtgaccgg cgcctagtgt   7680
tgacaattaa tcatcggcat agtatatcgg catagtataa tacgactcac tataggaggg   7740
ccaccatgtc gactactaac cttcttctct ttcctacagc tgagatcacc ggtaggaggg   7800
ccatcatgaa aaagcctgaa ctcaccgcga cgtctgtcgc gaagtttctg atcgaaaagt   7860
tcgacagcgt ctccgacctg atgcagctct cggagggcga agaatctcgt gctttcagct   7920
tcgatgtagg agggcgtgga tatgtcctgc gggtaaatag ctgcgccgat ggtttctaca   7980
aagatcgtta tgtttatcgg cactttgcat cggccgcgct cccgattccg gaagtgcttg   8040
acattgggga attcagcgag agcctgacct attgcatctc ccgccgtgca cagggtgtca   8100
cgttgcaaga cctgcctgaa accgaactgc ccgctgttct gcaacccgtc gcggagctca   8160
tggatgcgat cgctgcggcc gatcttagcc agacgagcgg gttcggccca ttcggaccgc   8220
aaggaatcgg tcaatacact acatggcgtg atttcatatg cgcgattgct gatccccatg   8280
tgtatcactg gcaaactgtg atggacgaca ccgtcagtgc gtccgtcgcg caggctctcg   8340
```

```
atgagctgat gctttgggcc gaggactgcc ccgaagtccg gcacctcgtg cacgcggatt    8400
tcggctccaa caatgtcctg acggacaatg ccgcataac agcggtcatt gactggagcg    8460
aggcgatgtt cggggattcc caatacgagg tcgccaacat cttcttctgg aggccgtggt    8520
tggcttgtat ggagcagcag acgcgctact tcgagcggag gcatccggag cttgcaggat    8580
cgccgcggct ccgggcgtat atgctccgca ttggtcttga ccaactctat cagagcttgg    8640
ttgacggcaa tttcgatgat gcagcttggg cgcagggtcg atgcgacgca atcgtccgat    8700
ccggagccgg gactgtcggg cgtacacaaa tcgcccgcag aagcgcggcc gtctggaccg    8760
atggctgtgt agaagtactc gccgatagtg aaaccgacg ccccagcact cgtccgaggg    8820
caaaggaatg agtcgagaat tcgctagagg gccctattct atagtgtcac ctaaatgcta    8880
gagctcgctg atcagcctcg actgtgcctt ctagttgcca gccatctgtt gtttgcccct    8940 ccccgtgcc ttccttgacc ctggaaggtg ccactccac tgtcctttcc taataaaatg      9000
aggaaattgc atcgcattgt ctgagtaggg gtcattctat tctgggggt ggggtggggc    9060 aggacagcaa gggggaggat tgggaagaca atagcaggca tgcgcagggc ccaattgctc    9120
gagcggccgc aataaaatat ctttattttc attacatctg tgtgttggtt ttttgtgtga    9180
atcgtaacta acatacgctc tccatcaaaa caaaacgaaa caaacaaac tagcaaaata    9240 ggctgtcccc agtgcaagtg caggtgccag aacatttctc tatcgaa              9287

<210> SEQ ID NO 21
<211> LENGTH: 529
<212> TYPE: DNA
<213> ORGANISM: Artificial Sequence
<220> FEATURE:
<223> OTHER INFORMATION: nucleotide sequence of human Ad type 5,
      E1b-19kd, coding region

<400> SEQUENCE: 21
atggaggctt gggagtgttt ggaagatttt tctgctgtgc gtaacttgct ggaacagagc      60
tctaacagta cctcttggtt ttggaggttt ctgtggggct catcccaggc aaagttagtc    120
tgcagaatta aggaggatta caagtgggaa tttgaagagc ttttgaaatc ctgtggtgag    180
ctgtttgatt ctttgaatct gggtcaccag gcgcttttcc aagagaaggt catcaagact    240
ttggattttt ccacaccggg gcgcgctgcg gctgctgttg cttttttgag ttttataaag    300
gataaatgga gcgaagaaac ccatctgagc gggggtacc tgctggattt tctggccatg    360
catctgtgga gagcggttgt gagacacaag aatcgcctgc tactgttgtc ttccgtccgc    420
ccggcgataa taccgacgga ggagcagcag cagcagcagg aggaagccag gcggcggcgg    480
caggagcaga gcccatggaa cccgagagcc ggcctggacc ctcgggaat             529

<210> SEQ ID NO 22
<211> LENGTH: 176
<212> TYPE: PRT
<213> ORGANISM: Artificial Sequence
<220> FEATURE:
<223> OTHER INFORMATION: amino acid sequence of human Ad type 5, E1b
      19K, protein

<400> SEQUENCE: 22

Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
```

35                  40                  45
Trp Glu Phe Glu Glu Leu Leu Lys Ser Cys Gly Glu Leu Phe Asp Ser
 50                  55                  60

Leu Asn Leu Gly His Gln Ala Leu Phe Gln Glu Lys Val Ile Lys Thr
 65                  70                  75                  80

Leu Asp Phe Ser Thr Pro Gly Arg Ala Ala Ala Val Ala Phe Leu
                 85                  90                  95

Ser Phe Ile Lys Asp Lys Trp Ser Glu Thr His Leu Ser Gly Gly
                100                 105                 110

Tyr Leu Leu Asp Phe Leu Ala Met His Leu Trp Arg Ala Val Val Arg
                115                 120                 125

His Lys Asn Arg Leu Leu Leu Leu Ser Ser Val Arg Pro Ala Ile Ile
                130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
                165                 170                 175

<210> SEQ ID NO 23
<211> LENGTH: 3597
<212> TYPE: DNA
<213> ORGANISM: Artificial Sequence
<220> FEATURE:
<223> OTHER INFORMATION: Nucleotide sequence of human Ad type 5, E2b
      polymerase coding region

<400> SEQUENCE: 23
atggccttgg ttcaagctca ccgggcccgt cgtcttcacg cagaggcgcc agattcagga      60
gatcaaccgc cgcgtcgtcg cgttcgccag caacctacgc gcgcagcacc agctcctgcc     120
cgcgcgcggc gccgacgtgc ccctgccccc tctcccggcg ggtccggagc cccccctacc     180
tccgggggct cgcccgcgtc accgctttta gatgcatcat ccaaggacac ccccgcggcc     240
caccgcccgc cgcgcggtac cgtagtcgcg ccgcggggat gcggcctctt gcaagccatc     300
gacgccgcca ccaaccagcc cctggaaatt aggtatcacc tggatctagc ccgcgccctg     360
acccgtctat gcgaggtaaa cctgcaggag ctcccgcctg acctgacgcc gcgggagctc     420
cagaccatgg acagctccca tctgcgcgat gttgtcatca gctccgaccg ccgcgcgcg     480
gacatctgga ctttgggctc gcgcggcgtg gtggtccgat ccaccgtaac tcccctcgag     540
cagccagacg tcaaggaca  agcagccgaa gtagaagacc accagccaaa cccgccaggc     600
gagggctca  aattcccact ctgcttcctt gtgcgcggtc gtcaggtcaa cctcgtgcag     660
gatgtacagc ccgtgcaccg ctgccagtac tgcgcacgtt tttacaaaag ccagcacgag     720
tgttcggccc gtcgcaggga cttctacttt caccacatca cagccactc  ctccaactgg     780
tggcgggaga tccagttctt cccgatcggc tcgcatcctc gcaccgagcg tctctttgtc     840
acctacgatg tagagaccta tacttggatg ggggcctttg ggaagcagct cgtgcccttc     900
atgctggtta tgaagttcgg cggagatgag cctctggtga ccgccgcgcg agacctagcc     960
gtggaccttg atgggaccg ctgggaacaa gacccgctta ccttctactg catcacccca    1020
gaaaaaatgg ccataggtcg ccagtttagg acctttcgcg accacctgca atgctaatg    1080
gcccgtgacc tgtggagctc attcgtcgct tccaaccctc atcttgcaga ctgggccctg    1140
tcagaacacg gctcagctc  ccctgaggag ctcacctacg aggaacttaa aaaattgccc    1200
tccatcaagg gcaccccgcg cttcttggaa ctttacatcg tgggcacaa  catcaacggc    1260

```
ttcgacgaga tcgtgctcgc cgcccaggta attaacaacc gttccgaggt gccgggaccc   1320
ttccgcatca cacgcaactt tatgcctcgc gcgggaaaga tacttttcaa cgatgtcacc   1380
ttcgccctgc caaacccgcg ttccaaaaag cgcacggact ttttgctctg ggagcagggc   1440
ggatgcgacg acactgactt caaataccag tacctcaaag tcatggttag ggacaccttt   1500
gcgctcaccc acacctcgct ccggaaggcc gcgcaggcat acgcgctacc cgtagaaaag   1560
ggatgctgcg cctaccaggc cgtcaaccag ttctacatgc taggctctta ccgttcggag   1620
gccgacgggt ttccgatcca agagtactgg aaagaccgcg aagagtttgt cctcaaccgc   1680
gagctgtgga aaaaaaggg acaggataag tatgacatca tcaaggaaac cctggactac   1740
tgcgccctag acgtgcaggt caccgccgag ctggtcaaca agctgcgcga ctcctacgcc   1800
tccttcgtgc gtgacgcggt aggtctcaca gacgccagct caacgtcctt ccagcgtcca   1860
accatatcat ccaactcaca tgccatcttc aggcagatag tcttccgagc agagcagccc   1920
gcccgtagca acctcggtcc cgacctcctc gctccctcgc acgaactata cgattacgtg   1980
cgcgccagca tccgcggtgg aagatgctac cctacatatc ttggaatact cagagagccc   2040
ctctacgttt acgacatttg cggcatgtac gcctccgcgc tcacccaccc catgccatgg   2100
ggtcccccac tcaacccata cgagcgcgcg cttgccgccc gcgcatggca gcaggcgcta   2160
gacttgcaag gatgcaagat agactacttc gacgcgcgcc tgctgcccgg ggtctttacc   2220
gtggacgcag acccccgga cgagacgcag ctagacccac taccgccatt ctgttcgcgc   2280
aagggcggcc gcctctgctg gaccaacgag cgcctacgcg gagaggtagc caccagcgtt   2340
gaccttgtca ccctgcacaa ccgcggttgg cgcgtgcacc tggtgcccga cgagcgcacc   2400
accgtctttc ccgaatggcg gtgcgttgcg cgcgaatacg tgcagctaaa catcgcggcc   2460
aaggagcgcg ccgatcgcga caaaaaccaa accctgcgct ccatcgccaa gttgctgtcc   2520
aacgccctct acgggtcgtt tgccaccaag cttgacaaca aaaagattgt cttttctgac   2580
cagatggacg cggccaccct caaaggcatc accgcgggcc aggtgaatat caaatcctcc   2640 tcgttttttgg aaactgacaa tcttagcgca gaagtcatgc ccgcttttga gagggagtac   2700
tcaccccaac agctggccct cgcagacagc gatgcggaag agagtgagga cgaacgcgcc   2760 cccacccct tttatagccc ccccttcagga acacccggtc acgtggccta cacctataaa   2820
ccaatcacct tccttgatgc cgaagagggc gacatgtgtc ttcacaccct ggagcgagtg   2880 gacccccctag tggacaacga ccgctacccc tcccacttag cctccttcgt gctggcctgg   2940
acgcgagcct tcgtctcaga gtggtccgag tttctatacg aggaggaccg cggaacaccg   3000
ctcgaggaca ggcctctcaa gtctgtatac ggggacacgg acagccttttt cgtcaccgag   3060 cgtggacacc ggctcatgga aaccagaggt aagaaacgca tcaaaaagca tgggggaaac   3120 ctggttttttg accccgaacg gccagagctc acctggctcg tggaatgcga accgtctgc    3180 ggggcctgcg gcgcggatgc ctactccccg gaatcggtat ttctcgcgcc caagctctac   3240
gcccttaaaa gtctgcactg cccctcgtgc ggcgcctcct ccaagggcaa gctgcgcgcc   3300
aagggccacg ccgcggaggg gctggactat gacaccatgg tcaaatgcta cctggccgac   3360
gcgcagggcg aagaccggca gcgcttcagc accagcagga ccagcctcaa gcgcaccctg   3420
gccagcgcgc agcccggagc gcaccccttc accgtgaccc agactacgct gacgaggacc   3480
ctgcgcccgt ggaaagacat gaccctggcc cgtctggacg agcaccgact actgccgtac   3540
agcgaaagcc gccccaaccc gcgaaacgag gagatatgct ggatcgagat gccgtag     3597
```

<210> SEQ ID NO 24
<211> LENGTH: 1198
<212> TYPE: PRT
<213> ORGANISM: Artificial Sequence
<220> FEATURE:
<223> OTHER INFORMATION: Amino acid sequence of human Ad type 5, E2b polymerase protein

<400> SEQUENCE: 24

```
Met Ala Leu Val Gln Ala His Arg Ala Arg Arg Leu His Ala Glu Ala
1               5                   10                  15

Pro Asp Ser Gly Asp Gln Pro Pro Arg Arg Val Arg Gln Gln Pro
            20                  25                  30

Thr Arg Ala Ala Pro Ala Pro Ala Arg Ala Arg Arg Arg Ala Pro
            35                  40                  45

Ala Pro Ser Pro Gly Gly Ser Gly Ala Pro Pro Ser Gly Gly Ser
50                  55                  60

Pro Ala Ser Pro Leu Leu Asp Ala Ser Ser Lys Asp Thr Pro Ala Ala
65                  70                  75                  80

His Arg Pro Pro Arg Gly Thr Val Val Ala Pro Arg Gly Cys Gly Leu
                85                  90                  95

Leu Gln Ala Ile Asp Ala Ala Thr Asn Gln Pro Leu Glu Ile Arg Tyr
                100                 105                 110

His Leu Asp Leu Ala Arg Ala Leu Thr Arg Leu Cys Glu Val Asn Leu
                115                 120                 125

Gln Glu Leu Pro Pro Asp Leu Thr Pro Arg Glu Leu Gln Thr Met Asp
        130                 135                 140

Ser Ser His Leu Arg Asp Val Val Ile Lys Leu Arg Pro Pro Arg Ala
145                 150                 155                 160

Asp Ile Trp Thr Leu Gly Ser Arg Gly Val Val Arg Ser Thr Val
                165                 170                 175

Thr Pro Leu Glu Gln Pro Asp Gly Gln Gly Gln Ala Ala Glu Val Glu
                180                 185                 190

Asp His Gln Pro Asn Pro Pro Gly Glu Gly Leu Lys Phe Pro Leu Cys
        195                 200                 205

Phe Leu Val Arg Gly Arg Gln Val Asn Leu Val Gln Asp Val Gln Pro
210                 215                 220

Val His Arg Cys Gln Tyr Cys Ala Arg Phe Tyr Lys Ser Gln His Glu
225                 230                 235                 240

Cys Ser Ala Arg Arg Arg Asp Phe Tyr Phe His His Ile Asn Ser His
                245                 250                 255

Ser Ser Asn Trp Trp Arg Glu Ile Gln Phe Phe Pro Ile Gly Ser His
                260                 265                 270

Pro Arg Thr Glu Arg Leu Phe Val Thr Tyr Asp Val Glu Thr Tyr Thr
        275                 280                 285

Trp Met Gly Ala Phe Gly Lys Gln Leu Val Pro Phe Met Leu Val Met
        290                 295                 300

Lys Phe Gly Gly Asp Glu Pro Leu Val Thr Ala Ala Arg Asp Leu Ala
305                 310                 315                 320

Val Asp Leu Gly Trp Asp Arg Trp Glu Gln Asp Pro Leu Thr Phe Tyr
                325                 330                 335

Cys Ile Thr Pro Glu Lys Met Ala Ile Gly Arg Gln Phe Arg Thr Phe
                340                 345                 350

Arg Asp His Leu Gln Met Leu Met Ala Arg Asp Leu Trp Ser Ser Phe
        355                 360                 365
```

-continued

```
Val Ala Ser Asn Pro His Leu Ala Asp Trp Ala Leu Ser Glu His Gly
    370                 375                 380

Leu Ser Ser Pro Glu Glu Leu Thr Tyr Glu Glu Leu Lys Lys Leu Pro
385                 390                 395                 400

Ser Ile Lys Gly Thr Pro Arg Phe Leu Glu Leu Tyr Ile Val Gly His
                405                 410                 415

Asn Ile Asn Gly Phe Asp Glu Ile Val Leu Ala Ala Gln Val Ile Asn
                420                 425                 430

Asn Arg Ser Glu Val Pro Gly Pro Phe Arg Ile Thr Arg Asn Phe Met
            435                 440                 445

Pro Arg Ala Gly Lys Ile Leu Phe Asn Asp Val Thr Phe Ala Leu Pro
    450                 455                 460

Asn Pro Arg Ser Lys Lys Arg Thr Asp Phe Leu Leu Trp Glu Gln Gly
465                 470                 475                 480

Gly Cys Asp Asp Thr Asp Phe Lys Tyr Gln Tyr Leu Lys Val Met Val
                485                 490                 495

Arg Asp Thr Phe Ala Leu Thr His Thr Ser Leu Arg Lys Ala Ala Gln
                500                 505                 510

Ala Tyr Ala Leu Pro Val Glu Lys Gly Cys Cys Ala Tyr Gln Ala Val
            515                 520                 525

Asn Gln Phe Tyr Met Leu Gly Ser Tyr Arg Ser Glu Ala Asp Gly Phe
            530                 535                 540

Pro Ile Gln Glu Tyr Trp Lys Asp Arg Glu Glu Phe Val Leu Asn Arg
545                 550                 555                 560

Glu Leu Trp Lys Lys Gly Gln Asp Lys Tyr Asp Ile Ile Lys Glu
                565                 570                 575

Thr Leu Asp Tyr Cys Ala Leu Asp Val Gln Val Thr Ala Glu Leu Val
                580                 585                 590

Asn Lys Leu Arg Asp Ser Tyr Ala Ser Phe Val Arg Asp Ala Val Gly
            595                 600                 605

Leu Thr Asp Ala Ser Phe Asn Val Phe Gln Arg Pro Thr Ile Ser Ser
    610                 615                 620

Asn Ser His Ala Ile Phe Arg Gln Ile Val Phe Arg Ala Glu Gln Pro
625                 630                 635                 640

Ala Arg Ser Asn Leu Gly Pro Asp Leu Leu Ala Pro Ser His Glu Leu
                645                 650                 655

Tyr Asp Tyr Val Arg Ala Ser Ile Arg Gly Gly Arg Cys Tyr Pro Thr
                660                 665                 670

Tyr Leu Gly Ile Leu Arg Glu Pro Leu Tyr Val Tyr Asp Ile Cys Gly
            675                 680                 685

Met Tyr Ala Ser Ala Leu Thr His Pro Met Pro Trp Gly Pro Pro Leu
    690                 695                 700

Asn Pro Tyr Glu Arg Ala Leu Ala Ala Arg Ala Trp Gln Gln Ala Leu
705                 710                 715                 720

Asp Leu Gln Gly Cys Lys Ile Asp Tyr Phe Asp Ala Arg Leu Leu Pro
                725                 730                 735

Gly Val Phe Thr Val Asp Ala Asp Pro Asp Glu Thr Gln Leu Asp
                740                 745                 750

Pro Leu Pro Pro Phe Cys Ser Arg Lys Gly Gly Arg Leu Cys Trp Thr
            755                 760                 765

Asn Glu Arg Leu Arg Gly Glu Val Ala Thr Ser Val Asp Leu Val Thr
770                 775                 780

Leu His Asn Arg Gly Trp Arg Val His Leu Val Pro Asp Glu Arg Thr
```

-continued

```
                785                 790                 795                 800
Thr Val Phe Pro Glu Trp Arg Cys Val Ala Arg Glu Tyr Val Gln Leu
                    805                 810                 815
Asn Ile Ala Ala Lys Glu Arg Ala Asp Arg Asp Lys Asn Gln Thr Leu
                    820                 825                 830
Arg Ser Ile Ala Lys Leu Leu Ser Asn Ala Leu Tyr Gly Ser Phe Ala
                    835                 840                 845
Thr Lys Leu Asp Asn Lys Lys Ile Val Phe Ser Asp Gln Met Asp Ala
                    850                 855                 860
Ala Thr Leu Lys Gly Ile Thr Ala Gly Gln Val Asn Ile Lys Ser Ser
865                 870                 875                 880
Ser Phe Leu Glu Thr Asp Asn Leu Ser Ala Glu Val Met Pro Ala Phe
                    885                 890                 895
Glu Arg Glu Tyr Ser Pro Gln Gln Leu Ala Leu Ala Asp Ser Asp Ala
                    900                 905                 910
Glu Glu Ser Glu Asp Glu Arg Ala Pro Thr Pro Phe Tyr Ser Pro Pro
                    915                 920                 925
Ser Gly Thr Pro Gly His Val Ala Tyr Thr Tyr Lys Pro Ile Thr Phe
                    930                 935                 940
Leu Asp Ala Glu Glu Gly Asp Met Cys Leu His Thr Leu Glu Arg Val
945                 950                 955                 960
Asp Pro Leu Val Asp Asn Asp Arg Tyr Pro Ser His Leu Ala Ser Phe
                    965                 970                 975
Val Leu Ala Trp Thr Arg Ala Phe Val Ser Glu Trp Ser Glu Phe Leu
                    980                 985                 990
Tyr Glu Glu Asp Arg Gly Thr Pro  Leu Glu Asp Arg Pro  Leu Lys Ser
                    995                 1000                1005
Val Tyr  Gly Asp Thr Asp Ser  Leu Phe Val Thr Glu  Arg Gly His
    1010                1015                1020
Arg Leu  Met Glu Thr Arg Gly  Lys Lys Arg Ile Lys  Lys His Gly
    1025                1030                1035
Gly Asn  Leu Val Phe Asp Pro  Glu Arg Pro Glu Leu  Thr Trp Leu
    1040                1045                1050
Val Glu  Cys Glu Thr Val Cys  Gly Ala Cys Gly Ala  Asp Ala Tyr
    1055                1060                1065
Ser Pro  Glu Ser Val Phe Leu  Ala Pro Lys Leu Tyr  Ala Leu Lys
    1070                1075                1080
Ser Leu  His Cys Pro Ser Cys  Gly Ala Ser Ser Lys  Gly Lys Leu
    1085                1090                1095
Arg Ala  Lys Gly His Ala Ala  Glu Gly Leu Asp Tyr  Asp Thr Met
    1100                1105                1110
Val Lys  Cys Tyr Leu Ala Asp  Ala Gln Gly Glu Asp  Arg Gln Arg
    1115                1120                1125
Phe Ser  Thr Ser Arg Thr Ser  Leu Lys Arg Thr Leu  Ala Ser Ala
    1130                1135                1140
Gln Pro  Gly Ala His Pro Phe  Thr Val Thr Gln Thr  Thr Leu Thr
    1145                1150                1155
Arg Thr  Leu Arg Pro Trp Lys  Asp Met Thr Leu Ala  Arg Leu Asp
    1160                1165                1170
Glu His  Arg Leu Leu Pro Tyr  Ser Glu Ser Arg Pro  Asn Pro Arg
    1175                1180                1185
Asn Glu  Glu Ile Cys Trp Ile  Glu Met Pro
    1190                1195
```

<210> SEQ ID NO 25
<211> LENGTH: 6454
<212> TYPE: DNA
<213> ORGANISM: Artificial
<220> FEATURE:
<223> OTHER INFORMATION: Nucleotide sequence of E2B coding region (PTP,POL,IVA2)

<400> SEQUENCE: 25

```
atggagcact ttttgccgct gcgcaacatc tggaaccgcg tccgcgactt ccgcgcgcc      60
tccaccaccg ccgccggcat cacctggatg tccaggtaca tctacggata tcatcgcctt    120
atgttggaag atctcgcccc cggagccccg gccaccctac gctggcccct ctaccgccag    180
ccgccgccgc acttttggt gggataccag tacctggtgc ggacttgcaa cgactacgta     240
tttgactcga gggcttactc gcgtctcagg tacaccgagc tctcgcagcc gggtcaccag    300
accgttaact ggtccgttat ggccaactgc acttacacca tcaacacggg cgcataccac    360
cgctttgtgg acatggatga cttccagtct accctcacgc aggtgcagca ggccatatta    420
gccgagcgcg ttgtcgccga cctagccctg cttcagccga tgaggggctt cggggtcaca    480
cgcatgggag gaagagggcg ccacctacgg ccaaactccg ccgccgccgc agcgatagat    540
gcaagagatg caggacaaga ggaaggagaa gaagaagtgc cggtagaaag gctcatgcaa    600
gactactaca agacctgccg ccgatgtcaa aacgaagcct ggggcatggc cgaccgcctg    660
cgcattcagc aggccggacc caaggacatg gtgcttctgt cgaccatccg ccgtctcaag    720
accgcctact ttaattacat catcagcagc acctccgcca gaaacaaccc cgaccgccgc    780
ccgctgccgc cgccacggt gctcagccta ccttgcgact gtgactggtt agacgccttt    840
ctcgagaggt tttccgatcc ggtcgatgcg gactcgctca ggtccctcgg cggcggagta    900
cctacacaac aattgttgag atgcatcgtt agcgccgtat ccctgccgca tggcagcccc    960
ccgccaaccc ataaccggga catgacgggc ggcgtcttcc aactgcgccc ccgcgagaac   1020
ggccgcgccg tcaccgagac catgcgccgt cgccgcgggg agatgatcga gcgctttgtc   1080
gaccgcctcc cggtgcgccg tcgtcgccgc cgtgtccccc ctcccccacc gccgccagaa   1140
gaagaagaag gggaggccct tatggaagag gagattgaag aagaagaaga ggcccctgta   1200
gcctttgagc gcgaggtgcg cgacactgtc gccgagctca tccgtcttct ggaggaggag   1260
ttaaccgtgt cggcgcgcaa ctcccagttt ttcaacttcg ccgtggactt ctacgaggcc   1320
atggagcgcc ttgaggcctt ggggatatc aacgaatcca cgttgcgacg ctgggttatg   1380
tacttcttcg tggcagaaca caccgccacc ccctcaact acctctttca gcgcctgcga   1440
aactacgccg tcttcgcccg gcacgtggag ctcaatctcg cgcaggtggt catgcgcgcc   1500
cgcgatgccg aagggggcgt ggtctacagc gcgtctgga acgagggagg cctcaacgcc   1560
ttctcgcagc tcatgcccg catttccaac gacctcgccg ccaccgtgga gcgagccgga   1620
cgcggagatc tccaggagga agagatcgag cagttcatgg ccgagatcgc ctatcaagac   1680
aactcaggag acgtgcagga gattttgcgc caggccgccg tcaacgacac cgaaattgat   1740
tctgtcgaac tctctttcag gctcaagctc accgggcccg tcgtcttcac gcagaggcgc   1800
cagattcagg agatcaaccg ccgcgtcgtc gcgttcgcca gcaacctacg cgcgcagcac   1860
cagctcctgc ccgcgcgcgg gccgacgtg cccctgcccc ctctcccggc gggtccggag   1920
ccccccctac ctccggggc tcgccccgcg caccgctttt agatgcatca tccaaggaca   1980
ccccgcggc caccgcccg ccgcgcggta ccgtagtcgc gccgcgggga tgcggcctct   2040
```

```
tgcaagccat cgacgccgcc accaaccagc ccctggaaat taggtatcac ctggatctag   2100
cccgcgccct gacccgtcta tgcgaggtaa acctgcagga gctcccgcct gacctgacgc   2160
cgcgggagct ccagaccatg gacagctccc atctgcgcga tgttgtcatc aagctccgac   2220
cgccgcgcgc ggacatctgg actttgggct cgcgcggcgt ggtggtccga tccaccgtaa   2280
ctcccctcga gcagccagac ggtcaaggac aagcagccga agtagaagac caccagccaa   2340
acccgccagg cgagggcgctc aaattcccac tctgcttcct tgtgcgcggt cgtcaggtca   2400
acctcgtgca ggatgtacag cccgtgcacc gctgccagta ctgcgcacgt ttttacaaaa   2460
gccagcacga gtgttcggcc cgtcgcaggg acttctactt tcaccacatc aatagccact   2520
cctccaattg gtggcgggag atccagttct tcccgatcgg ctcgcatcct cgcaccgagc   2580
gtctctttgt cacctacgat gtagagacct atacttggat gggggccttt gggaagcagc   2640
tcgtgccctt catgctggtc atgaagttcg gcggagatga gcctctagtg actgccgcgc   2700
gagacctagc cgcgaacctt ggatgggacc gctgggaaca agacccgctt accttctact   2760
gcatcacccc agaaaaaatg gccataggtc gccagtttag gaccttttcgc gaccaccctgc   2820 aaatgctaat ggcccgtgac ctgtggagct cattcgtcgc ttccaaccct catcttgcag   2880
actgggcccc ttcagagcac gggctcagct cccctgaaga gctcacctac gaggaactta   2940
aaaaattgcc ttccatcaag ggcatcccgc gcttcttgga actttacatt gtgggccaca   3000
acatcaacgg ctttgacgag atcgtgctcg ccgcccaggt aattaacaac cgttccgagg   3060
tgccgggacc cttccgcatc acacgcaact ttatgcctcg cgcgggaaag atactcttca   3120
acgatgtcac cttcgccctg ccaaatccgc gttccaaaaa gcgcacggac ttttttgctct   3180 gggagcaggg cggatgcgac gacactgact tcaaatacca gtacctcaaa gtcatggtca   3240
gggacacctt tgcgctcacc cacacctcgc tccggaaggc cgcgcaggca tacgcgctac   3300
ccgtagaaaa gggatgctgc gcctaccagg ccgtcaacca gttctacatg ctaggctctt   3360
accgttcgga ggccgacggg tttccgatcc aagagtactg gaaagaccgc gaagagtttg   3420
tcctcaaccg cgagctgtgg aaaaaaaagg gacaggataa gtatgacatc atcaaggaaa   3480
ccctggacta ctgcgcccta gacgtgcagg tcaccgccga gctggtcaac aagctgcgcg   3540
actcctacgc ctccttcgtg cgtgacgcgg taggtctcac agacgccagc ttcaacgtct   3600
tccagcgtcc aaccatatca tccaactcac atgccatctt caggcagata gtcttccgag   3660
cagagcagcc cgcccgtagc aacctcggtc ccgacctcct cgctccctcg cacgaactat   3720
acgattacgt gcgcgccagc atccgcggtg gaagatgcta ccctacatat cttggaatac   3780
tcagagagcc cctctacgtt tacgacattt gcggcatgta cgcctccgcg ctcacccacc   3840
ccatgccatg gggtcccccca ctcaacccat acgagcgcgc gcttgccgcc cgcgcatggc   3900
agcaggcgct agacttgcaa ggatgcaaga tagactactt cgacgcgcgc ctgctgcccg   3960
gggtctttac cgtggacgca gaccccccgg acgagacgca gctagacccc ctaccgccat   4020
tctgctcgcg caagggcggc cgcctctgct ggaccaacga gcgcctacgc ggagaggtag   4080
ccaccagcgt tgaccttgtc accctgcaca accgcggttg gcgcgtgcac ctggtgcccg   4140
acgagcgcac caccgtcttt ccgaatggcg gtgcgttgc gcgcgaatac gtgcagctaa   4200
acatcgcggc caaggagcgc gccgatcgcg acaaaaacca aaccctgcgc tccatcgcca   4260
agttgctgtc caacgccctc tacgggtcgt ttgccaccaa gcttgacaac aaaaagattg   4320 tctttttctga ccagatggat gcggccaccc tcaaaggcat caccgcgggc caggtgaata   4380
```

```
tcaaatcctc ctcgttttg gaaactgaca atcttagcgc agaagtcatg cccgcttttc    4440
agagggagta ctcaccccaa cagctggccc tcgcagacag cgatgcggaa gagagtgagg    4500
acgaacgcgc ccccaccccc ttttatagcc ccccttcagg aacacccggt cacgtggcct    4560
acacctacaa accaatcacc ttccttgatg ccgaagaggg cgacatgtgt cttcacaccc    4620
tggagcgagt ggaccccta gtggacaacg accgctaccc ctcccactta gcctccttcg     4680
tgctggcctg gacgcgagcc tttgtctcag agtggtccga gtttctatac gaggaggacc    4740
gcggaacacc gctcgaggac aggcctctca agtctgtata cggggacacg gacagccttt    4800
tcgtcaccga gcgtggacac cggctcatgg aaaccagagg taagaaacgc atcaaaaagc    4860
atggggggaaa cctggttttt gaccccgaac ggccagagct cacctggctc gtggaatgcg    4920
agaccgtctg cggggcctgc ggcgcggatg cctactcccc ggaatcggta tttctcgcgc    4980
ccaagctcta cgccctcaaa agtctgcact gccctcgtg cggcgcctcc tccaagggca     5040
agctgcgcgc caaggccac gccgcggagg ggctggacta tgacaccatg gtcaaatgct     5100
acctggccga cgcgcagggc gaagaccggc agcgcttcag caccagcagg accagcctca    5160
agcgcaccct ggccagcgcg cagcccggag cgcaccccctt caccgtgacc cagactacgc    5220
tgacgaggac cctgcgcccg tggaaagaca tgaccctggc ccgtctggac gagcaccgac    5280
tactgccgta cagcgaaagc cgccccaacc cgcgaaacga ggagatatgc tggatcgaga    5340
tgccgtagag caggtgaccg agctgtggga ccgcctggaa ctgcttggtc aaacgctcaa    5400
aagcatgcct acgcggacg gtctcaaacc gttgaaaaac tttgcttcct tgcaagaact    5460
gctatcgctg ggcggcgagc gccttctggc ggatttggtc agggaaaaca tgcgagtcag    5520
ggacatgctt aacgaagtgg ccccctgct cagggatgac ggcagctgca gctctcttaa    5580
ctaccagttg caccccggtaa taggtgtgat ttacggcccc accggctgcg gtaagtcgca    5640
gctgctcagg aacctgcttt cttcccagct gatctcccct accccggaaa ccgttttctt    5700
catcgccccg caggtagaca tgatccccc atctgaactc aaagcgtggg aaatgcaaat    5760
ctgtgagggt aactacgccc ctgggccgga tggaaccatt ataccgcagt ctggcacccct    5820
ccgcccgcgc tttgtaaaaa tggcctatga cgatctcatc ctggaacaca actatgacgt    5880
tagtgatccc agaaatatct tcgcccaggc cgccgcccgt gggcccattg ccatcattat    5940
ggacgaatgc atggaaaatc ttggaggtca aagggcgtc tccaagttct ccacgcatt    6000
tccttctaag ctacatgaca aatttcccaa gtgcaccgga tacactgtgc tggtggttct    6060
gcacaacatg aatccccgga gggatatggc tgggaacata gccaacctaa aaatacagtc    6120
caagatgcat ctcatatccc cacgtatgca cccatcccag cttaaccgct ttgtaaacac    6180
ttacaccaag ggcctgcccc tgcaatcag cttgctactg aaagacattt ttaggcacca    6240
cgcccagcgc tcctgctacg actggatcat ctacaacacc cccccgcagc atgaagctct    6300
gcagtggtgc tacctccacc ccagagacgg gcttatgccc atgtatctga acatccagag    6360
tcacctttac cacgtcctgg aaaaaataca caggaccctc aacgaccgag accgctggtc    6420
ccggggcctac cgcgcgcgca aaacccctaa ataa                              6454
```

<210> SEQ ID NO 26
<211> LENGTH: 765
<212> TYPE: DNA
<213> ORGANISM: Artificial
<220> FEATURE:
<223> OTHER INFORMATION: Nucleotide sequence of human adenovirus type 5,
    E1A-dl01/07, coding region

<400> SEQUENCE: 26

```
atgagacatg aggtactggc tgataatctt ccacctccta gccatttgga accacctacc      60
cttcacgaac tgtatgattt agacgtgacg gcccccgaag atcccaacga ggaggcggtt     120
tcgcagattt ttcccgactc tgtaatgttg gcggtgcagg aagggattga cttactcact     180
tttccgccgg cgcccggttc tccggagccg cctcaccttt cccggcagcc cgagcagccg     240
gagcagagag ccttgggtcc ggtttgccac gaggctggct ttccacccag tgacgacgag     300
gatgaagagg gtgaggagtt tgtgttagat tatgtggagc accccgggca cggttgcagg     360
tcttgtcatt atcaccggag gaatacgggg gacccagata ttatgtgttc gctttgctat     420
atgaggacct gtggcatgtt tgtctacagt cctgtgtctg aacctgagcc tgagcccgag     480
ccagaaccgg agcctgcaag acctacccgc cgtcctaaaa tggcgcctgc tatcctgaga     540
cgccccgacat cacctgtgtc tagagaatgc aatagtagta cggatagctg tgactccggt     600
ccttctaaca cacctcctga gatacacccg gtggtcccgc tgtgccccat taaaccagtt     660
gccgtgagag ttggtgggcg tcgccaggct gtggaatgta tcgaggactt gcttaacgag     720
cctgggcaac ctttggactt gagctgtaaa cgccccaggc cataa                     765
```

<210> SEQ ID NO 27
<211> LENGTH: 254
<212> TYPE: PRT
<213> ORGANISM: Artificial
<220> FEATURE:
<223> OTHER INFORMATION: Amino acid residues of human adenovirus type 5, E1A-dl01/07, protein

<400> SEQUENCE: 27

```
Met Arg His Glu Val Leu Ala Asp Asn Leu Pro Pro Pro Ser His Phe
1               5                   10                  15

Glu Pro Pro Thr Leu His Glu Leu Tyr Asp Leu Asp Val Thr Ala Pro
            20                  25                  30

Glu Asp Pro Asn Glu Glu Ala Val Ser Gln Ile Phe Pro Asp Ser Val
        35                  40                  45

Met Leu Ala Val Gln Glu Gly Ile Asp Leu Leu Thr Phe Pro Pro Ala
    50                  55                  60

Pro Gly Ser Pro Glu Pro Pro His Leu Ser Arg Gln Pro Glu Gln Pro
65                  70                  75                  80

Glu Gln Arg Ala Leu Gly Pro Val Cys His Glu Ala Gly Phe Pro Pro
                85                  90                  95

Ser Asp Asp Glu Asp Glu Gly Glu Glu Phe Val Leu Asp Tyr Val
            100                 105                 110

Glu His Pro Gly His Gly Cys Arg Ser Cys His Tyr His Arg Arg Asn
        115                 120                 125

Thr Gly Asp Pro Asp Ile Met Cys Ser Leu Cys Tyr Met Arg Thr Cys
    130                 135                 140

Gly Met Phe Val Tyr Ser Pro Val Ser Glu Pro Glu Pro Glu Pro Glu
145                 150                 155                 160

Pro Glu Pro Glu Pro Ala Arg Pro Thr Arg Arg Pro Lys Met Ala Pro
                165                 170                 175

Ala Ile Leu Arg Arg Pro Thr Ser Pro Val Ser Arg Glu Cys Asn Ser
            180                 185                 190

Ser Thr Asp Ser Cys Asp Ser Gly Pro Ser Asn Thr Pro Pro Glu Ile
        195                 200                 205

His Pro Val Val Pro Leu Cys Pro Ile Lys Pro Val Ala Val Arg Val
```

-continued

```
        210                 215                 220
Gly Gly Arg Arg Gln Ala Val Glu Cys Ile Glu Asp Leu Leu Asn Glu
225                 230                 235                 240

Pro Gly Gln Pro Leu Asp Leu Ser Cys Lys Arg Pro Arg Pro
                245                 250
```